US009375471B2

(12) United States Patent
Baudner et al.

(10) Patent No.: US 9,375,471 B2
(45) Date of Patent: Jun. 28, 2016

(54) ADJUVANTED FORMULATIONS OF BOOSTER VACCINES

(71) Applicant: Novartis AG, Basel (CH)

(72) Inventors: Barbara Baudner, Siena (IT); Derek O'Hagan, Winchester, MA (US); Manmohan Singh, Cary, NC (US); Simone Bufali, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 13/790,948

(22) Filed: Mar. 8, 2013

(65) Prior Publication Data

US 2013/0236492 A1    Sep. 12, 2013

Related U.S. Application Data

(60) Provisional application No. 61/608,398, filed on Mar. 8, 2012, provisional application No. 61/697,730, filed on Sep. 6, 2012.

(51) Int. Cl.
| | | |
|---|---|---|
| *A61K 39/02* | (2006.01) | |
| *A61K 39/00* | (2006.01) | |
| *A61K 39/38* | (2006.01) | |
| *A61K 39/39* | (2006.01) | |

(52) U.S. Cl.
CPC .............. *A61K 39/39* (2013.01); *A61K 39/0018* (2013.01); *A61K 2039/55505* (2013.01); *A61K 2039/55511* (2013.01); *A61K 2039/55566* (2013.01); *A61K 2039/55572* (2013.01)

(58) Field of Classification Search
CPC ....... A61K 39/00; A61K 39/02; A61K 39/05; A61K 39/08; A61K 39/12; A61K 39/13
USPC .......... 424/184.1, 204.1, 217.1, 234.1, 236.1, 424/238.1, 239.1, 240.1, 245.1, 247.1, 424/278.1
See application file for complete search history.

(56) References Cited

U.S. PATENT DOCUMENTS

| | | | |
|---|---|---|---|
| 4,666,886 A | 5/1987 | Baschang et al. | |
| 5,059,258 A | 10/1991 | Wefers et al. | |
| 5,936,076 A | 8/1999 | Higa et al. | |
| 6,699,474 B1 | 3/2004 | Cerny | |
| 7,115,592 B2 | 10/2006 | Balzarini et al. | |
| 7,220,545 B2 | 5/2007 | Binz et al. | |
| 7,309,494 B2 | 12/2007 | Corvaia et al. | |
| 7,488,490 B2 | 2/2009 | Davis et al. | |
| 7,691,877 B2 | 4/2010 | Jones et al. | |
| 7,771,726 B2 | 8/2010 | Tsuji et al. | |
| 8,222,257 B2 | 7/2012 | Hostetler et al. | |
| 8,275,711 B2 | 9/2012 | Jackowski et al. | |
| 8,367,670 B2 | 2/2013 | Desai et al. | |
| 8,466,167 B2 | 6/2013 | Wu et al. | |
| 9,045,470 B2 | 6/2015 | Wu et al. | |
| 2004/0202668 A1* | 10/2004 | Boutriau et al. | ........... 424/184.1 |
| 2008/0008682 A1 | 1/2008 | Chong et al. | |
| 2009/0099216 A1 | 4/2009 | Millichip et al. | |
| 2009/0105212 A1 | 4/2009 | Isobe et al. | |
| 2009/0118263 A1 | 5/2009 | Hashimoto et al. | |
| 2009/0143400 A1 | 6/2009 | McInally et al. | |
| 2009/0192153 A1 | 7/2009 | Hashimoto et al. | |
| 2009/0221631 A1 | 9/2009 | Jones et al. | |
| 2009/0232844 A1* | 9/2009 | Sutton et al. | ............... 424/209.1 |
| 2010/0056031 A1 | 3/2010 | Chiu et al. | |
| 2011/0028715 A1 | 2/2011 | Isobe et al. | |
| 2011/0180430 A1 | 7/2011 | Rappuoli et al. | |
| 2012/0177681 A1 | 7/2012 | Singh et al. | |
| 2012/0237546 A1 | 9/2012 | Singh et al. | |
| 2013/0122042 A1 | 5/2013 | Otten et al. | |
| 2013/0274465 A1 | 10/2013 | Singh et al. | |
| 2013/0330840 A1 | 12/2013 | Skibinski et al. | |
| 2014/0112950 A1 | 4/2014 | Singh et al. | |
| 2014/0363461 A1 | 12/2014 | Bagnoli et al. | |
| 2015/0030630 A1 | 1/2015 | Jain et al. | |
| 2015/0125475 A1 | 5/2015 | Dodd et al. | |
| 2015/0132339 A1 | 5/2015 | Bufali et al. | |
| 2015/0190493 A1 | 7/2015 | Baudner et al. | |
| 2015/0258190 A1 | 9/2015 | Grandi | |

FOREIGN PATENT DOCUMENTS

| | | |
|---|---|---|
| CN | 1130226 C | 12/2003 |
| CN | 101522217 A | 9/2009 |
| WO | WO-9318150 A1 | 9/1993 |
| WO | WO-9527787 A1 | 10/1995 |
| WO | WO-9601272 A1 | 1/1996 |
| WO | WO-9601273 A1 | 1/1996 |
| WO | WO-9616046 A2 | 5/1996 |
| WO | WO-9725429 A1 | 7/1997 |
| WO | WO-98/19702 A1 | 5/1998 |

(Continued)

OTHER PUBLICATIONS

Munoz, F.M. Pertussis in infants, children, and adolescents: Diagnosis, treatment, and Prevention. Seminars in Pediatric Infectious Diseases, vol. 17, No. 1, pp. 14-19, 2006.*
Vergara, R. et al. Reduced-antigen-content-diphtheria-tetanus-acellular-pertussis and inactivated polio vaccine as a booster for adolescents 10-14 years of age. European Journal of Pediatrics. vol. 164, No. 6, pp. 377-382, Jun. 2005.*
Banus et al. (2008). "The role of Toll-like receptor-4 in pertussis vaccine-induced immunity." BMC Immunol. 9:21:1471-2172.
Garcon et al (2006). "Development and evaluation of AS04, a novel and improved adjuvant system containing MPL and aluminum salt," Immunopotentiators in Modern Vaccines, p. 161-177.
Geurtsen et al. (2007). "Lipopolysaccharide analogs improve efficacy of acellular pertussis vaccine and reduce type I hypersensitivity in mice." Clin Vaccine Immunol. 14(7):821-9.
Gröndahl-Yli-Hannuksela et al. (2012). "Gene polymorphism in toll-like receptor 4: effect on antibody production and persistence after acellular pertussis vaccination during adolescence," J Infect Dis. 205(8):1214-9.

(Continued)

*Primary Examiner* — Rodney P Swartz
(74) *Attorney, Agent, or Firm* — Morrison & Foerster LLP

(57) ABSTRACT

The invention improves TdaP vaccines by including a TLR agonist in them. This agonist can provide stronger protection, longer-lasting protection, and/or can reduce the amount of antigen which is required to achieve a particular immune response.

19 Claims, 1 Drawing Sheet

(56) References Cited

FOREIGN PATENT DOCUMENTS

| | | |
|---|---|---|
| WO | WO-9819702 | 5/1998 |
| WO | WO-0037494 A2 | 6/2000 |
| WO | WO-0202606 A2 | 1/2002 |
| WO | WO-03010317 A1 | 2/2003 |
| WO | WO-03049762 A2 | 6/2003 |
| WO | WO-03097091 A2 | 11/2003 |
| WO | WO-03105769 A2 | 12/2003 |
| WO | WO-2004032958 A1 | 4/2004 |
| WO | WO-2004111064 A1 | 12/2004 |
| WO | WO-2005002619 A2 | 1/2005 |
| WO | WO-2005/089794 A2 | 9/2005 |
| WO | WO-2005084306 A2 | 9/2005 |
| WO | WO-2005102049 A1 | 11/2005 |
| WO | WO-2006089264 A2 | 8/2006 |
| WO | WO-2006091517 A2 | 8/2006 |
| WO | WO-2006138004 A2 | 12/2006 |
| WO | WO-2007/000322 A1 | 1/2007 |
| WO | WO-2007034173 A1 | 3/2007 |
| WO | WO-2007034917 A1 | 3/2007 |
| WO | WO-2007040840 A2 | 4/2007 |
| WO | WO-2007060548 A2 | 5/2007 |
| WO | WO-2007093901 A1 | 8/2007 |
| WO | WO-2007109813 | 9/2007 |
| WO | WO-2007110700 A2 | 10/2007 |
| WO | WO-2008004948 A1 | 1/2008 |
| WO | WO-2008005555 A1 | 1/2008 |
| WO | WO-2008/020328 A2 | 2/2008 |
| WO | WO-2008020328 | 2/2008 |
| WO | WO-2008020330 A2 | 2/2008 |
| WO | WO-2008/028957 A2 | 3/2008 |
| WO | WO-2008047174 A1 | 4/2008 |
| WO | WO-2008047249 A2 | 4/2008 |
| WO | WO-2008101867 A1 | 8/2008 |
| WO | WO-2008114817 A1 | 9/2008 |
| WO | WO-2008135791 A1 | 11/2008 |
| WO | WO-2009019553 A2 | 2/2009 |
| WO | WO-2009050586 A1 | 4/2009 |
| WO | WO-2009067081 A1 | 5/2009 |
| WO | WO-2009081172 A1 | 7/2009 |
| WO | WO-2009111337 | 9/2009 |
| WO | WO-2009118296 A2 | 10/2009 |
| WO | WO-2010003009 A2 | 1/2010 |
| WO | WO-2010014913 A1 | 2/2010 |
| WO | WO-2010067201 | 6/2010 |
| WO | WO-2010077613 A1 | 7/2010 |
| WO | WO-2010/094663 A1 | 8/2010 |
| WO | WO-2010119343 A2 | 10/2010 |
| WO | WO-2010140119 A1 | 12/2010 |
| WO | WO-2010144734 | 12/2010 |
| WO | WO-2011/027222 A2 | 3/2011 |
| WO | WO-2011024072 A2 | 3/2011 |
| WO | WO-2011/057267 A1 | 5/2011 |
| WO | WO-2011119759 A1 | 9/2011 |
| WO | WO-2012031140 A1 | 3/2012 |
| WO | WO-2012117377 | 9/2012 |

OTHER PUBLICATIONS

Mansour et al. (2007). "Improved Efficacy of a Licensed Acellular Pertussis Vaccine, Reformulated in an Adjuvant Emulsion of Liposomes in Oil, in a Murine Model," Clin Vaccine Immunol. 14(10): 1381-1383.

Racke et al. (2005). "PTX cruiser: driving autoimmunity via TLR4," Trend Immunol. 26(6):289-91.

S.L. Hem & H. Hogenesch. (2007). "Relationship between physical and chemical properties of aluminum-containing adjuvants and immunopotentiation," Expert Review Vaccines, 6(5): 685-698.

S.L. Hem & J.L. White. (1995). "Structure and Properties of Aluminum-Containing Adjuvants," Vaccine Design: The subunit 1 and adjuvant approach, ed. M.F. Powell and M.J. Newman (Plenum Press, New York), vol. 6, Chapter 9, pp. 249-276.

Steinhagen et al. (2011). "TLR-based immune adjuvants," Vaccine, 29(17):3341-55.

Sugai et al. (2005). "A CpG-containing oligodeoxynucleotide as an efficient adjuvant counterbalancing the Th1/Th2 immune response in diptheria-tetanus-pertussis vaccine." Vaccine. 23(46-47):5450-6.

van Duin D (2006). "Triggering TLR signaling in vaccination," Trends Immunol. Jan. 2006; 27(1):49-55.

International Search Report mailed Oct. 2, 2014, for International Application No. PCT/EP2013/054672, filed Mar. 8, 2013. 9 pages.

Written Opinion for International Application No. PCT/EP2013/054672, filed Mar. 8, 2013. 13 pages.

International Search Report for International Application No. PCT/IB2010/002386, mailed Feb. 18, 2011, 5 pages.

Response to United States Advisory Action, mailed on Jan. 8, 2015, for U.S. Appl. No. 13/394,036, filed May 30, 2012.

Response to United States Final Office Action, mailed on Dec. 4, 2014, for U.S. Appl. No. 13/394,036, filed May 30, 2012.

United Stated Advisory Action mailed on Dec. 11, 2014, for U.S. Appl. No. 13/394,036, filed May 30, 2012.

United States Final Office Action mailed on Sep. 8, 2014, for U.S. Appl. No. 13/394,036, filed May 30, 2012.

Wack et al. (2008). "Combination adjuvants for the induction of potent, long-lasting antibody and T-cell responses to influenza vaccine in mice," Vaccine, 26(4):552-61.

Written Opinion for International Application No. PCT/IB2010/002386, mailed Mar. 2, 2013, 6 pages.

Wu et al. (2014). "Rational design of small molecules as vaccine adjuvants," Sci Transl Med, 6(263):263ra160.

Abarca (2003). "Reduced-Antigen Combined Diphtheria-Tetanus-Acellular Pertussis Vaccine (Boostrix) a Viewpoint by Katia Abarca," Drugs, Adis International Ltd, NZ, 63(13): 1415.

Billaudelle et al. (1962). "[Triple vaccine without aluminium-carrier]," Nord Med, 68:1339-40.

Brewer (2006). "(How) do aluminium adjuvants work?" Immunol Lett, 102(1):10-5.

Hem et al. (2007). "Relationship between physical and chemical properties of aluminum-containing adjuvants and immunopotentiation," Expert Review Vaccines, 6(5): 685-698.

International Search Report, mailed Aug. 14, 2012, for International Application No. PCT/IB2012/050989, filed Mar. 2, 2012.

Scheifele et al. (1995). "Can reductions in diphtheria toxoid or aluminum content reduce the reactogenicity of booster doses of DPT vaccine?" Immunology and Infectious Diseases (Oxford, GB), 5(1):73-77.

Singh et al. (2006). "A preliminary evaluation of alternative adjuvants to alum using a range of established and new generation vaccine antigens," Vaccine, 24(10):1680-6.

United States Office Action mailed on Sep. 16, 2015, for U.S. Appl. No. 14/002,700, filed Jan. 10, 2014.

Vecchi et al. (2012). "Aluminum adjuvant dose guidelines in vaccine formulation for preclinical evaluations," J Pharm Sci, 101(1):17-20.

Wendorf et al. (2008). "A comparison of anionic nanoparticles and microparticles as vaccine delivery systems," Hum Vaccin, 4(1):44-9.

Barnett et al. (2001). "The ability of an oligomeric human immunodeficiency virus type 1 (HIV-1) envelope antigen to elicit neutralizing antibodies against primary HIV-1 isolates is improved following partial deletion of the second hypervariable region," J Virol, 75(12):5526-40.

Bortolatto, J. et al. (2008). "Toll-like receptor 4 agonists adsorbed to aluminium hydroxide adjuvant attenuate ovalbumin-specific allergic airway disease: role of MyD88 adaptor molecule and interleukin-12/interferon-gamma axis," Clin. Exper. Aller., 38(10): 1668-1679.

Burrell et al., (1999). "Stability of aluminium-containing adjuvants to autoclaving," Vaccine, 17(20-21):2599-603.

Cassone & Torosantucci, (2006). "Opportunistic fungi and fungal infections: the challenge of a single, general antifungal vaccine," Expert Rev Vaccines, 5(6):859-67.

CDC, (1998). "Notice to readers availability of new rabies vaccine for human use," MMWR Morb Mortal Weekly Report, 47(1):12, 19. 3 pages.

Chang et al., (2001). "Degree of antigen adsorption in the vaccine or interstitial fluid and its effect on the antibody response in rabbits," Vaccine, 19(20-22):2884-9.

Clausi et al., (2008). "Influence of particle size and antigen binding on effectiveness of aluminum salt adjuvants in a model lysozyme vaccine," J Pharm Sci, 97(12):5252-62.

(56) References Cited

OTHER PUBLICATIONS

Cooper, C. L. et al., "Cpg 7909, an Immunostimulatory TLR9 Agonist Oligodeoxynucleotide, as Adjuvant to Engerix-B (R) HBV Vaccine in Healthy Adults: A Double-Blind Phase I/II Study," J. Clin. Immun., 24(6): 693-701 (2004).
Covacci & Rappuoli, (2000). "Tyrosine-phosphorylated bacterial proteins: Trojan horses for the host cell," J. Exp. Med. 191(4):587-592.
Covacci et al., (1993). "Molecular characterization of the 128-kDa immunodominant antigen of Helicobacter pylori associated with cytotoxicity and duodenal ulcer," Proc. Natl. Acad. Sci. USA, 90(12):5791-5795.
Dasarai et al., (2011). "Recombinant glycoprotein B vaccine formulation with Toll-like receptor 9 agonist and immune-stimulating complex induces specific immunity against multiple strains of cytomegalovirus," J Gen Virol, 92:1021-31.
Davis et al. (1998). "CpG DNA is a potent enhancer of specific immunity in mice immunized with recombinant hepatitis B surface antigen," J Immunol, 160(2):870-6.
De Libero et al, (2005). "Recognition of lipid antigens by T cells," Nature Reviews Immunology, 5:485-496.
Earl et al., (2001). "Immunogenicity and protective efficacy of oligomeric human immunodeficiency virus type 1 gp140," J Virol, 75(2):645-53.
Evans et al., (1995). "Identification of four new prokaryotic bacterioferritins, from Helicobacter pylori, Anabaena variabilis, Bacillus subtilis and Treponema pallidum, by analysis of gene sequences," Gene, 153:123-127.
Gennaro, (2000). "Table of Contents," Remington: The Science and Practice of Pharmacy, 20th edition, ISBN: 0683306472. 4 pages.
Giuliani et al., (2006). "A universal vaccine for serogroup B meningococcus," Proc Natl Acad Sci USA, 103(29):10834-9.
Goff et al, (2004). "Effects of lipid chain lengths in alpha-galactosylceramides on cytokine release by natural killer T cells," J. Am. Chem. Soc., 126(42):13602-13603.
Hancock, G. E. et al. (2003). "Adjuvants recognized by toll-like receptors inhibit the induction of polarized type 2 T cell responses by natural attachment (G) protein of respiratory syncytial virus," Vaccines 21 (27-30): 4348-4358.
Harper et al., (2004). "Efficacy of a bivalent L1 virus-like particle vaccine in prevention of infection with human papillomavirus types 16 and 18 in young women: a randomised controlled trial," Lancet, 364(9447): 1757-65.
Hashiro et al. (2009). "Rapid and Efficient Induction of an Endogenous Cell Signaling Event by Subcellular Targeting of a Synthetic Ligand" JAGS, 131(38):13568-13569.
Hockova et al., (2003), "5-Substituted-2,4-diamino-6[2-(phosphonomethoxy)ethoxy]pyrimidines-acyclic nucleoside phosphonate analogues with antiviral activity," J. Med. Chem., 46:5064-5073.
Iyer et al., (2004). "Mechanism of adsorption of hepatitis B surface antigen by aluminum hydroxide adjuvant," Vaccine, 22:1475-9.
Keitel et al., (1996). "Increasing doses of purified influenza virus hemagglutinin and subvirion vaccines enhance antibody responses in the elderly," Clin Diagn Lab Immunol, 3(5):507-10.
Leroux-Roels, G. (2010). "Unmet needs in Modern Vaccinology Adjuvants to Improve the Immune Response," Vaccine, 28(3): C25-C36.
Levesque & de Alwis, (2005). "Mechanism of adsorption of three recombinant Streptococcus pneumoniae (Sp) vaccine antigens by an aluminum adjuvant," Human Vaccines, 1(2):70-3.
Marchetti et al., (1998), "Protection against Helicobacter pylori infection in mice by intragastric vaccination with H. pylori antigens is achieved using a non-toxic mutant of *E. coli* heat-labile enterotoxin (LT) as adjuvant," Vaccine, 16(1):33-37.
Mendez et al., (2007). "Potentiation of the immune response to non-adsorbed antigens by aluminum-containing adjuvants,"Vaccine, 25(5):825-33.
Morefield et al., (2005). "Effect of phosphorylation of ovalbumin on adsorption by aluminum-containing adjuvants and elution upon exposure to interstitial fluid," Vaccine 23(13): 1502-6.
Nencioni et al., (1991), "Properties of pertussis toxin mutant PT-9K/129G after formaldehyde treatment," Infect Immun, 59(2): 625-30.
Oki et al., (2004). "The clinical implication and molecular mechanism of preferential IL-4 production by modified glycolipid-stimulated NKT cells," J. Clin. Investig, 113(11):1631-1640.
Powell & Newman, (1995). "Table of Contents," Pharmaceutical Biotechnology, vol. 6. Vaccine Design: The Subunit and Adjuvant Approach. ISBN: 030644867X. 23 pages.
Rappuoli et al., (1991). "Towards third-generation whooping cough vaccines," TIBTECH 9:232-238.
Response to Final Office Action mailed Dec. 4, 2014, for U.S. Appl. No. 13/394,036, 22 pages.
Response to Office Action mailed Jul. 24, 2015, for U.S. Appl. No. 13/223,793, 54 pages.
Response to Office Action mailed Sep. 15, 2015, for U.S. Appl. No. 13/820,370, 16 pages.
Rosenberg et al., (2010). "TLR reporter cell lines for screening TLR agonists and antagonists," J Immunol 184: 136.20. Meeting Abstract. 2 pages.
Shi et al., (2002), "Change in the degree of adsorption of proteins by aluminum-containing adjuvants following exposure to interstitial fluid: freshly prepared and aged model vaccines," Vaccine 20:80-5.
Telford et al., (1994). "Gene structure of the Helicobacter pylori cytotoxin and evidence of its key role in gastric disease," J. Exp. Med., 179:1653-1658.
Treanor et al., (1996). "Evaluation of a recombinant hemagglutinin expressed in insect cells as an influenza vaccine in young and elderly adults," J Infect Dis, 173:1467-70.
Tummuru et al., (1993). "Cloning and expression of a high-molecular-mass major antigen of Helicobacter pylori: evidence of linkage to cytotoxin production," Infect. Immun., 61(5):1799-1809.
United States Final Office Action mailed Oct. 5, 2015, for U.S. Appl. No. 13/223,793, 16 pages.
United States Notice of Allowance mailed Sep. 29, 2015, for U.S. Appl. No. 13/820,370, 7 pages.
United States Office Action mailed Aug. 14, 2015, for U.S. Appl. No. 13/394,036, 10 pages.
Yang et al., (2004). "The C-glycoside analogue of the immunostimulant alpha-galactosylceramide (KRN7000): synthesis and striking enhancement of activity," Angew Chem Int Ed, 43: 3818-3822.
Zhang et al., (2001), "Expression, purification, and characterization of recombinant HIV gp140. The gp41 ectodomain of HIV or simian immunodeficiency virus is sufficient to maintain the retroviral envelope glycoprotein as a trimer," J. Biol. Chem. 276(43):39577-85.

* cited by examiner

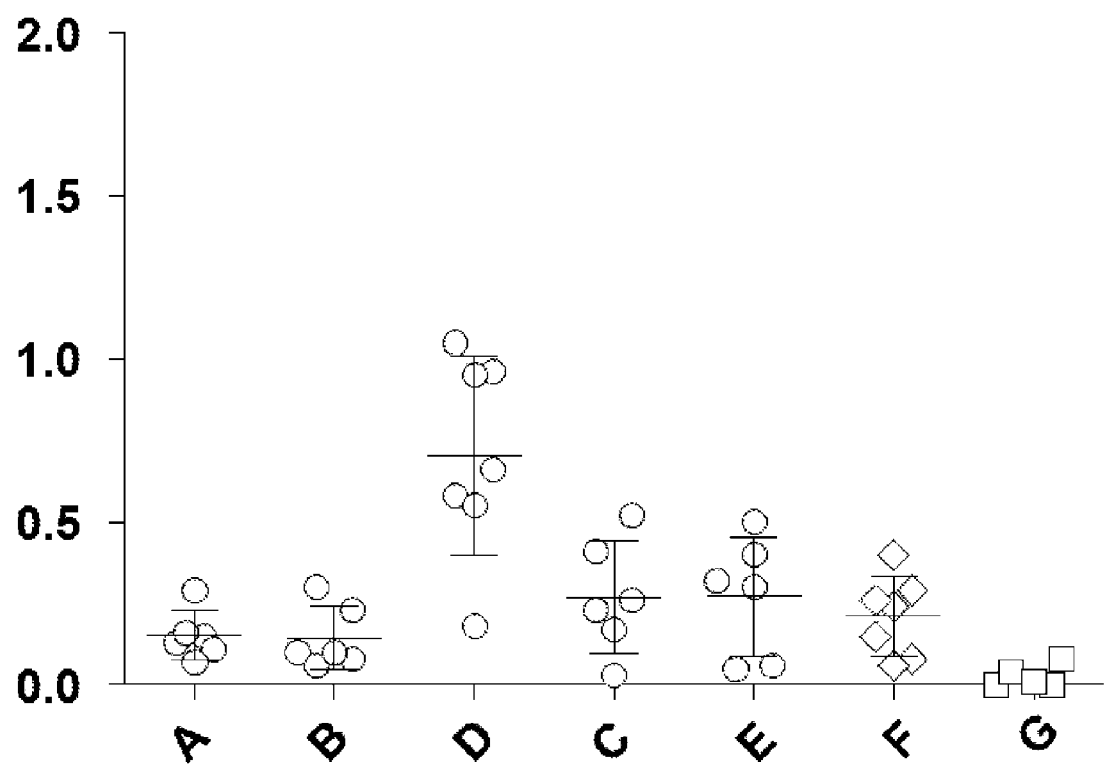

ADJUVANTED FORMULATIONS OF BOOSTER VACCINES

CROSS REFERENCE TO RELATED APPLICATIONS

This application claims the benefit of U.S. provisional applications 61/608,398 (filed Mar. 8, 2012) and 61/697,730 (filed Sep. 6, 2012), the complete contents of both of which are hereby incorporated herein by reference for all purposes.

FIELD OF THE INVENTION

The invention is in the field of booster vaccines for diphtheria, tetanus and pertussis.

BACKGROUND

Two adolescent DTP booster vaccines are currently available—BOOSTRIX™ & ADACEL™ [1]. Both vaccines contain diphtheria toxoid, tetanus toxoid and acellular pertussis antigens. They are also available in combination with inactivated poliovirus (BOOSTRIX POLIO™ and ADACEL POLIO™). All of these vaccines include an aluminium salt adjuvant.

In general these vaccines are known as TdaP vaccines, in contrast to pediatric DTaP vaccines. A common feature is that, relative to their pediatric counterparts, they have lower antigen doses e.g. the diphtheria toxoid content of BOOSTRIX™ is 10-fold lower than in the INFANRIX™ products, and in ADACEL™ it is 7.5-fold lower than in DAPTACEL™. Moreover, the ratio of antigenic components is also altered. In particular, the ratio of diphtheria and tetanus toxoids is 2.5:1 in the INFANRIX™ products but is 1:2 in the BOOSTRIX™ product, and is 3:1 in the DAPTACEL™ product but is 1:2.5 in the ADACEL™ product. Thus these booster vaccines show a large reduction in the dose of diphtheria toxoid, both in absolute amounts and also relative to the tetanus toxoid content. Some of the pertussis components also differ from the levels seen in the pediatric counterparts, but the levels of the poliovirus antigens are the same in both the pediatric and adolescent vaccines. Based on public information the compositions are as follows:

|  | D | T | Pa[1] | IPV[3] | Volume | Al$^{+++}$ |
|---|---|---|---|---|---|---|
| Boostrix™ | 2.5 Lf | 5 Lf | 8/8/2.5 | — | 0.5 ml | ≤0.39 mg |
| Boostrix Polio™ | 2.5 Lf | 5 Lf | 8/8/2.5 | 40/8/32 | 0.5 ml | 0.5 mg |
| Adacel™ | 2 Lf | 5 Lf | 2.5/5/3[2] | — | 0.5 ml | 0.33 mg |
| Adacel Polio™ | 2 Lf | 5 Lf | 2.5/5/3[2] | 40/8/32 | 0.5 ml | 0.33 mg |

Notes:
[1]Pa dose shows amounts of pertussis toxoid, then FHA, then pertactin (µg).
[2]Adacel's Pa components also contain 5 µg fimbriae types 2 and 3.
[3]IPV dose shows amounts of type 1, then type 2, then type 3 (measured in DU).

It is an object of the invention to provide further and improved TdaP vaccines suitable for human use as a booster in adults, adolescents and children aged four years and older who have previously received childhood immunisation.

SUMMARY OF THE INVENTION

In a first aspect, the invention improves current TdaP vaccines by including a TLR agonist in them. This agonist can provide stronger protection, longer-lasting protection, and/or can reduce the amount of antigen which is required to achieve a particular immune response.

In a second aspect, the invention improves current TdaP vaccines by adjuvanting them with an oil-in-water emulsion. This emulsion can again improve protection relative to known TdaP vaccines.

For the first aspect the invention therefore provides an immunogenic composition comprising a diphtheria toxoid, a tetanus toxoid, a pertussis toxoid, an aluminium salt adjuvant, and a TLR agonist, wherein the composition includes an excess of tetanus toxoid relative to diphtheria toxoid (in Lf units).

The TLR agonist is ideally a TLR4 agonist or a TLR7 agonist. Preferably, the TLR agonist and/or at least one of the toxoids is/are adsorbed to the aluminium salt adjuvant.

By including a TLR agonist it is possible for the compositions to have a lower amount of antigen and/or lower amount of aluminium relative to known vaccines, while nevertheless having comparable immunogenicity.

Ideally the composition has one or more of the following properties:
 an Al$^{+++}$ concentration of ≤0.5 mg/ml;
 a diphtheria toxoid concentration of ≤4 Lf/ml;
 a tetanus toxoid concentration of ≤9 Lf/ml; and/or
 a pertussis toxoid concentration of ≤4 µg/ml.

For instance, where the immunogenic composition is in a unit dose form for administration to a patient (e.g. in a 0.5 ml volume), it can have one or more of the following properties:
 an Al$^{+++}$ content of ≤0.255 mg;
 a diphtheria toxoid content of <2 Lf;
 a tetanus toxoid content of ≤4.5 Lf; and/or
 a pertussis toxoid content of ≤2 µg.

For the second aspect the invention provides an immunogenic composition comprising a diphtheria toxoid, a tetanus toxoid, a pertussis toxoid, and an oil-in-water emulsion adjuvant, wherein the composition includes an excess of tetanus toxoid relative to diphtheria toxoid (in Lf units).

Ideally the composition has one or more of the following properties:
 a diphtheria toxoid concentration of ≤4 Lf/ml;
 a tetanus toxoid concentration of ≤9 Lf/ml; and/or
 a pertussis toxoid concentration of ≤4 µg/ml.

For instance, where the immunogenic composition is in a unit dose form for administration to a patient (e.g. in a 0.5 ml volume), it can have one or more of the following properties:
 a diphtheria toxoid content of ≤2 Lf;
 a tetanus toxoid content of ≤4.5 Lf; and/or
 a pertussis toxoid content of ≤2 µg.

For both aspects, compositions of the invention can include antigens in addition to diphtheria toxoid, tetanus toxoid, and pertussis toxoid e.g. they can include an inactivated poliovirus (IPV) component.

Aluminium Salts

TLR agonists can adsorb to insoluble aluminium salts to form an adsorbed complex for adjuvanting TdaP immunogens. Such aluminium salts have a long history of use in vaccines.

Useful aluminium salts include, but are not limited to, aluminium hydroxide and aluminium phosphate adjuvants. Such salts are described e.g. in chapters 8 & 9 of reference 2, and chapter 4 of reference 3. Aluminium salts which include hydroxide ions are preferred for use with the present invention as these hydroxide ions can readily undergo ligand exchange. Thus preferred salts for adsorption of TLR agonists are aluminium hydroxide and/or aluminium hydroxyphosphate. These have surface hydroxyl moieties which can readily undergo ligand exchange with phosphorus-containing groups (e.g. phosphates, phosphonates) to provide stable adsorption. An aluminium hydroxide adjuvant is most preferred.

The adjuvants commonly known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 $cm^{-1}$ and a strong shoulder at 3090-3100 $cm^{-1}$ (chapter 9 of ref. 2). The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants e.g. with needle-like particles with diameters about 2 nm. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

The adjuvants commonly known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a $PO_4/Al$ molar ratio between 0.3 and 1.2. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls (chapter 9 of reference 2).

The $PO_4/Al^{+++}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $Al^{+++}/ml$. The aluminium phosphate will generally be particulate (e.g. plate-like morphology as seen in transmission electron micrographs, with primary particles in the range of 50 nm). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

In solution both aluminium phosphate and hydroxide adjuvants tend to form stable porous aggregates 1-10 μm in diameter [4].

A composition including a TLR agonist adsorbed to an aluminium salt can also include a buffer (e.g. a phosphate or a histidine or a Tris buffer). When such a composition includes a phosphate buffer, however, it is preferred that the concentration of phosphate ions in the buffer should be less than 50 mM e.g. <40 mM, <30 mM, <20 mM, <10 mM, or <5 mM, or between 1-15 mM. A histidine buffer is preferred e.g. between 1-50 mM, between 5-25 mM, or about 10 mM.

Because of the insolubility of adsorptive aluminium salts which are useful with the invention, compositions containing adsorbed TLR agonists will generally be suspensions having a cloudy appearance. This can mask contaminating bacterial growth and so a composition of the invention may include a preservative such as thiomersal or 2-phenoxyethanol. It is preferred that a composition should be substantially free from (e.g. <10 μg/ml) mercurial material e.g. thiomersal-free. Compositions containing no mercury are more preferred. Preservative-free compositions are also possible A composition can include a mixture of both an aluminium hydroxide and an aluminium phosphate, and a TLR agonist may be adsorbed to one or both of these salts.

The concentration of $Al^{+++}$ in a composition for administration to a patient is preferably less than 0.5 mg/ml e.g. ≤0.4 mg/ml, ≤0.3 mg/ml, ≤0.2 mg/ml, ≤0.1 mg/ml, etc. Because the inclusion of a TLR agonist can improve the adjuvant effect of aluminium salts then the invention advantageously permits lower amounts of $Al^{+++}$ per dose, and so a composition of the invention can usefully include between 10 and 250 μg of $Al^{+++}$ per unit dose. Current TdaP vaccines include at least 330 μg $Al^{+++}$ per dose. In concentration terms, a composition of the invention may have an $Al^{+++}$ concentration between 10 and 500 μg/ml e.g. between 10-300 μg/ml, between 10-200 μg/ml, or between 10-100 μg/ml.

In general, the weight ratio of TLR agonist to $Al^{+++}$ will be less than 5:1 e.g. less than 4:1, less than 3:1, less than 2:1, or less than 1:1. Thus, for example, with an $Al^{+++}$ concentration of 0.5 mg/ml the maximum concentration of TLR agonist would be 2.5 mg/ml. But higher or lower levels can be used. A lower mass of TLR agonist than of $Al^{+++}$ can be most typical e.g. per dose, 100 μg of TLR agonist with 0.2 mg $Al^{+++}$ etc. For instance, the Fendrix product includes 50 μg of 3d-MPL and 0.5 mg $Al^{+++}$ per dose.

It is preferred that at least 50% (by mass) of TLR agonist(s) in the composition is adsorbed to the aluminium salt e.g. ≥60%, ≥70%, ≥80%, ≥85%, ≥90%, ≥92%, ≥94%, ≥95%, ≥96%, ≥97%, ≥98%, ≥99%, or even 100%.

TLR Agonists

In its first aspect, compositions of the invention include a TLR agonist i.e. a compound which can agonise a Toll-like receptor. Most preferably, a TLR agonist is an agonist of a human TLR. The TLR agonist can activate any of TLR1, TLR2, TLR3, TLR4, TLR5, TLR6, TLR7, TLR8, TLR9 or TLR11; preferably it can activate human TLR4 or human TLR7.

Agonist activity of a compound against any particular Toll-like receptor can be determined by standard assays. Companies such as Imgenex and Invivogen supply cell lines which are stably co-transfected with human TLR genes and NFκB, plus suitable reporter genes, for measuring TLR activation pathways. They are designed for sensitivity, broad working range dynamics and can be used for high-throughput screening. Constitutive expression of one or two specific TLRs is typical in such cell lines. See also reference 5. Many TLR agonists are known in the art e.g. reference 6 describes certain lipopeptide molecules that are TLR2 agonists, references 7 to 10 each describe classes of small molecule agonists of TLR7, and references 11 & 12 describe TLR7 and TLR8 agonists for treatment of diseases.

A TLR agonist used with the invention ideally includes at least one adsorptive moiety. The inclusion of such moieties in TLR agonists allows them to adsorb to insoluble aluminium salts (e.g. by ligand exchange or any other suitable mechanism) and improves their immunological behaviour [13]. Phosphorus-containing adsorptive moieties are particularly useful, and so an adsorptive moiety may comprise a phosphate, a phosphonate, a phosphinate, a phosphonite, a phosphinite, etc.

Preferably the TLR agonist includes at least one phosphonate group.

Thus, in preferred embodiments, a composition of the invention includes a TLR agonist (more preferably a TLR7 agonist) which includes a phosphonate group. This phosphonate group can allow adsorption of the agonist to an insoluble aluminium salt [13].

TLR agonists useful with the invention may include a single adsorptive moiety, or may include more than one e.g. between 2 and 15 adsorptive moieties. Typically a compound will include 1, 2 or 3 adsorptive moieties.

Phosphorus-containing TLR agonists useful with the invention can be represented by formula (A1):

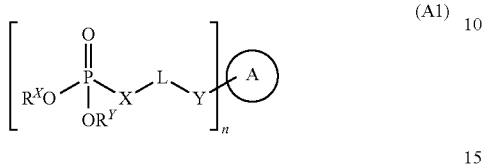

wherein:
R$^X$ and R$^Y$ are independently selected from H and $C_1$-$C_6$ alkyl;
X is selected from a covalent bond, O and NH;
Y is selected from a covalent bond, O, C(O), S and NH;
L is a linker e.g. selected from, $C_1$-$C_6$alkylene, $C_1$-$C_6$alkenylene, arylene, heteroarylene, $C_1$-$C_6$alkyleneoxy and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$;
each p is independently selected from 1, 2, 3, 4, 5 and 6;
q is selected from 1, 2, 3 and 4;
n is selected from 1, 2 and 3; and
A is a TLR agonist moiety.

In one embodiment, the TLR agonist according to formula (A1) is as follows: R$^X$ and R$^Y$ are H; X is O; L is selected from $C_1$-$C_6$ alkylene and —$((CH_2)_pO)_q(CH_2)_p$— each optionally substituted with 1 to 2 halogen atoms; p is selected from 1, 2 and 3; q is selected from 1 and 2; and n is 1. Thus in these embodiments the adsorptive moiety comprises a phosphate group.

In other embodiments, the TLR agonist according to formula (A1) is as follows: R$^X$ and R$^Y$ are H; X is a covalent bond; L is selected from $C_1$-$C_6$ alkylene and —$((CH_2)_pO)_q(CH_2)_p$— each optionally substituted with 1 to 2 halogen atoms; p is selected from 1, 2 or 3; q is selected from 1 or 2; and n is 1. Thus in these embodiments the adsorptive moiety comprises a phosphonate group.

Useful 'A' moieties for formula (A1) include, but are not limited to, radicals of any of the following compounds, defined herein or as disclosed in references 4-13 and 14-48:

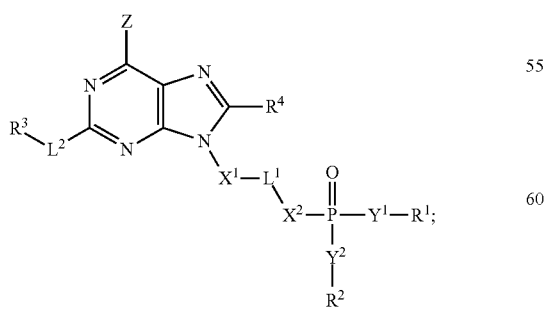

as defined on pages 2-7 of reference 8

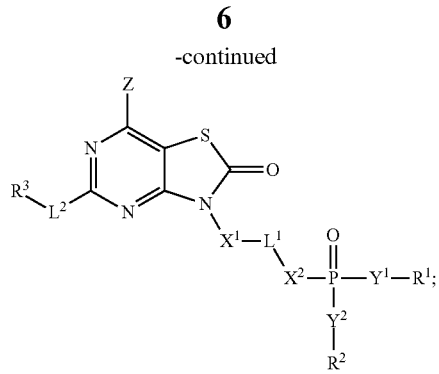

as defined on pages 2-5 & 7-8 of ref. 8

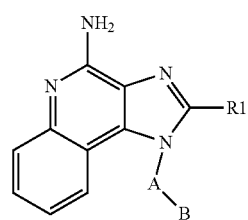

as defined on pages 6 and 7 of refernce 7;

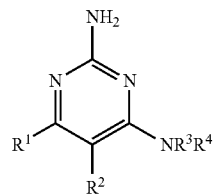

as defined on pages 2 to 5 of reference 10;

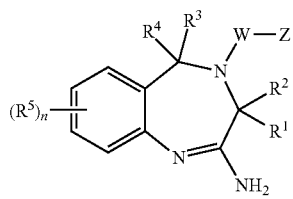

as defined on pages 5 to 6 of reference 11;

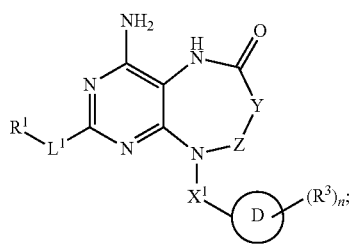

as defined on pages 2 to 3 of reference 48

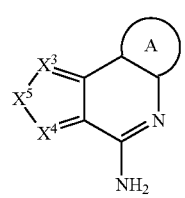

as defined on pages 2-4 of reference 9

-continued

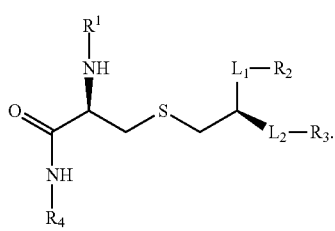

as defined in reference 14

In some embodiments, the TLR agonist moiety 'A' has a molecular weight of less than 1000 Da. In some embodiments, the TLR agonist of formula (A1) has a molecular weight of less than 1000 Da.

Preferred TLR agonists are water-soluble. Thus they can form a homogenous solution when mixed in an aqueous buffer with water at pH 7 at 25° C. and 1 atmosphere pressure to give a solution which has a concentration of at least 50 µg/ml. The term "water-soluble" thus excludes substances that are only sparingly soluble under these conditions.

Useful TLR agonists include those having formula (C), (D), (E), (F), (G), (H), (I), (II), (J) or (K) as described in more detail below. Other useful TLR agonists are compounds 1 to 102 as defined in reference 13. Preferred TLR7 agonists have formula (K), such as compound K2 identified below. These can be used as salts e.g. the arginine salt of K2.

Preferred TLR4 agonists are analogs of monophosphoryl lipid A (MPL), as described in more detail below. For instance, a useful TLR4 agonist is a 3d-MPL.

A composition of the invention can include more than one TLR agonist. These two agonists are different from each other and they can target the same TLR or different TLRs. Both agonists can be adsorbed to an aluminium salt.

Formulae (C), (D), (E) and (H)—TLR7 Agonists

The TLR agonist can be a compound according to any of formulae (C), (D), (E), and (H):

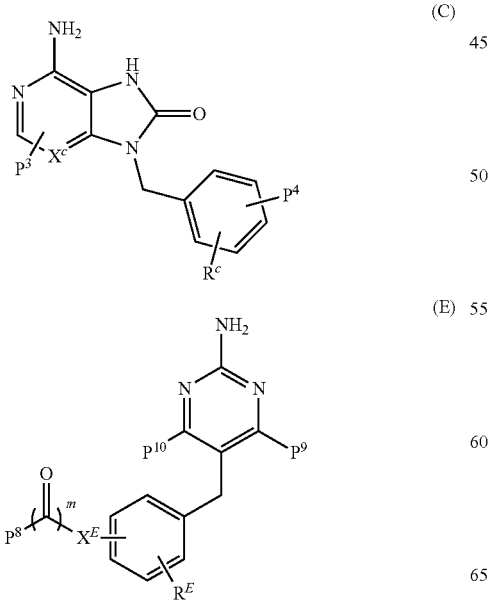

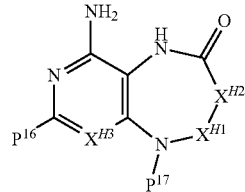

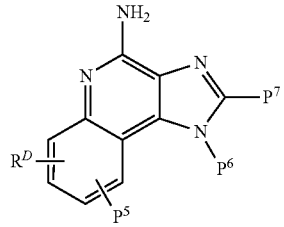

wherein:
(a) $P^3$ is selected from H, $C_1$-$C_6$alkyl, $CF_3$, and —$((CH_2)_pO)_q(CH_2)_pO_s$— and —Y-L-X—P(O)(OR$^X$)(OR$^Y$); and $P^4$ is selected from H, $C_1$-$C_6$alkyl, —$C_1$-$C_6$alkylaryl and —Y-L-X—P(O)(OR$^X$)(OR$^Y$); with the proviso that at least one of $P^3$ and $P^4$ is —Y-L-X—P(O)(OR$^X$)(OR$^Y$), (b) $P^5$ is selected from H, $C_1$-$C_6$alkyl, and —Y-L-X—P(O)(OR$^X$)(OR$^Y$); $P^6$ is selected from H, $C_1$-$C_6$alkyl each optionally substituted with 1 to 3 substituents selected from $C_1$-$C_4$alkyl and OH, and —Y-L-X—P(O)(OR$^X$)(OR$^Y$); and $P^7$ is selected from H, $C_1$-$C_6$alkyl, —$((CH_2)_pO)_q(CH_2)_pO_s$—, —NH$C_1$-$C_6$alkyl and —Y-L-X—P(O)(OR$^X$)(OR$^Y$); with the proviso that at least one of $P^5$, $P^6$ and $P^7$ is —Y-L-X—P(O)(OR$^X$)(OR$^Y$);

(c) $P^8$ is selected from H, $C_1$-$C_6$alkyl, $C_1$-$C_6$alkoxy, —NH$C_1$-$C_6$alkyl each optionally substituted with OH, and —Y-L-X—P(O)(OR$^X$)(OR$^Y$); and $P^9$ and $P^{10}$ are each independently selected from H, $C_1$-$C_6$alkyl, $C_1$-$C_6$alkoxy, —NH$C_1$-$C_6$alkyl each optionally substituted with OH and $C_1$-$C_6$alkyl, and —Y-L-X—P(O)(OR$^X$)(OR$^Y$); with the proviso that at least one of $P^8$, $P^9$ or $P^{10}$ is —Y-L-X—P(O)(OR$^X$)(OR$^Y$);

(d) $P^{16}$ and each $P^{18}$ are each independently selected from H, $C_1$-$C_6$alkyl, and —Y-L-X—P(O)(OR$^X$)(OR$^Y$); $P^{17}$ is selected from H, $C_1$-$C_6$alkyl, aryl, heteroaryl, $C_1$-$C_6$alkylaryl, $C_1$-$C_6$alkyl heteroaryl, $C_1$-$C_6$alkylaryl-Y-L-X—P(O)(OR$^X$)(OR$^Y$) and —Y-L-X—P(O)(OR$^X$)(OR$^Y$), each optionally substituted with 1 to 2 substituents selected from $C_1$-$C_6$alkyl or heterocyclyl with the proviso that at least one of $P^{16}$, $P^{17}$ or a $P^{18}$ contains a —Y-L-X—P(O)(OR$^X$)(OR$^Y$) moiety;

$R^X$ and $R^Y$ are independently selected from H and $C_1$-$C_6$alkyl;

$R^C$, $R^D$ and $R^H$ are each independently selected from H and $C_1$-$C_6$alkyl;

$X^C$ is selected from CH and N;

$R^E$ is selected from H, $C_1$-$C_6$alkyl, $C_1$-$C_6$alkoxy, C(O)$C_1$-$C_6$alkyl, halogen and —$((CH_2)_pO)_q(CH_2)_p$—;

$X^E$ is selected from a covalent bond, CR$^{E2}$R$^{E3}$ and NR$^{E4}$;

$R^{E2}$, $R^{E3}$ and $R^{E4}$ are independently selected from H and $C_1$-$C_6$alkyl;

$X^{H1}$—$X^{H2}$ is selected from —CR$^{H2}$R$^{H3}$—, —CR$^{H2}$R$^{H3}$—CR$^{H2}$R$^{H3}$—, —C(O)CR$^{H2}$R$^{H3}$—, —C(O)CR$^{H2}$R$^{H3}$—CR$^{H2}$R$^{H3}$C(O)—, —NR$^{H4}$C(O)—, —C(O)NR$^{H4}$—, CR$^{H2}$R$^{H3}$S(O)$_2$ and —CR$^{H2}$=CR$^{H2}$—;

$R^{H2}$, $R^{H3}$ and $R^{H4}$ are each independently selected from H, $C_1$-$C_6$alkyl and $P^{18}$;

$X^{H3}$ is selected from N and CN;

X is selected from a covalent bond, O and NH;

Y is selected from a covalent bond, O, C(O), S and NH;
L is selected from, a covalent bond C$_1$-C$_6$alkylene, C$_1$-C$_6$alkenylene, arylene, heteroarylene, C$_1$-C$_6$alkyleneoxy and —((CH$_2$)$_p$O)$_q$(CH$_2$)$_p$— each optionally substituted with 1 to 4 substituents independently selected from halo, OH, C$_1$-C$_4$alkyl, —OP(O)(OH)$_2$ and —P(O)(OH)$_2$;
m is selected from 0 or 1;
each p is independently selected from 1, 2, 3, 4, 5 and 6;
q is selected from 1, 2, 3 and 4; and
s is selected from 0 and 1.

Formula (G)—TLR8 Agonist

The TLR agonist can be a compound according to formula (G):

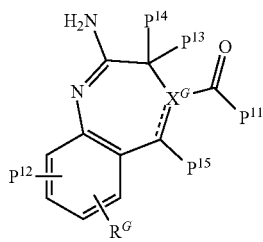

(G)

wherein:
P$^{11}$ is selected from H, C$_1$-C$_6$alkyl, C$_1$-C$_6$ alkoxy, NR$^V$R$^W$ and —Y-L-X—P(O)(OR$^X$)(OR$^Y$);
P$^{12}$ is selected from H, C$_1$-C$_6$alkyl, aryl optionally substituted by —C(O)NR$^V$R$^W$, and —Y-L-X—P(O)(OR$^X$)(OR$^Y$);
P$^{13}$, P$^{14}$ and P$^{15}$ are independently selected from H, C$_1$-C$_6$alkyl, C$_1$-C$_6$ alkoxy and —Y-L-X—P(O)(OR$^X$)(OR$^Y$);
with the proviso that at least one of P$^{11}$, P$^{12}$, P$^{13}$, P$^{14}$ or P$^{15}$ is —Y-L-X—P(O)(OR$^X$)(OR$^Y$);
R$^V$ and R$^W$ are independently selected from H, C$_1$-C$_6$alkyl or together with the nitrogen atom to which they are attached form a 4 to 7 remembered heterocyclic ring;
X$^G$ is selected from C, CH and N; -----
----- represents an optional double bond, wherein X$^G$ is C if ----- is a double bond; and
R$^G$ is selected from H and C$_1$-C$_6$alkyl;
X is selected from a covalent bond, O and NH;
Y is selected from a covalent bond, O, C(O), S and NH;
L is selected from, a covalent bond C$_1$-C$_6$alkylene, C$_1$-C$_6$alkenylene, arylene, heteroarylene, C$_1$-C$_6$alkyleneoxy and —((CH$_2$)$_p$O)$_q$(CH$_2$)$_p$— each optionally substituted with 1 to 4 substituents independently selected from halo, OH, C$_1$-C$_4$alkyl, —OP(O)(OH)$_2$ and —P(O)(OH)$_2$;
each p is independently selected from 1, 2, 3, 4, 5 and 6 and
q is selected from 1, 2, 3 and 4.

Formulae (I) and (II)—TLR7 Agonists [8]

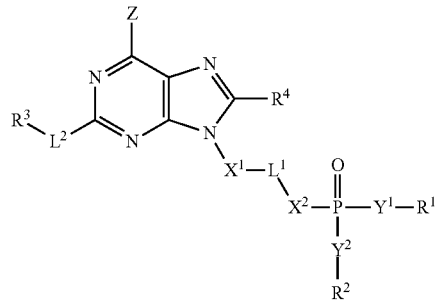

I

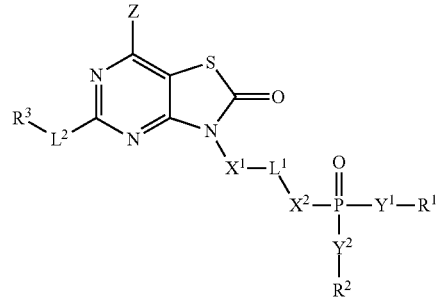

II

The TLR agonist can be a compound according to formula (I) or formula (II):
wherein:
Z is —NH$_2$ or —OH;
X$^1$ is alkylene, substituted alkylene, alkenylene, substituted alkenylene, alkynylene, substituted alkynylene, carbocyclylene, substituted carbocyclylene, heterocyclylene, or substituted heterocyclylene;
L$^1$ is a covalent bond, arylene, substituted arylene, heterocyclylene, substituted heterocyclylene, carbocyclylene, substituted carbocyclylene, —S—, —S(O)—, S(O)$_2$, —NR$^5$—, or —O—
X$^2$ is a covalent bond, alkylene, or substituted alkylene;
L$^2$ is NR$^5$—, —N(R$^5$)C(O)—, —O—, —S—, —S(O)—, S(O)$_2$, or a covalent bond;
R$^3$ is H, alkyl, substituted alkyl, heteroalkyl, substituted heteroalkyl, alkenyl, substituted alkenyl, aryl, substituted aryl, arylalkyl, substituted arylalkyl, heterocyclyl, substituted heterocyclyl, heterocyclylalkyl, or substituted heterocyclylalkyl;
Y$^1$ and Y$^2$ are each independently a covalent bond, —O— or —NR$^5$—; or —Y$^1$—R$^1$ and —Y$^2$—R$^2$ are each independently —O—N=C(R$^6$R$^7$);
R$^1$ and R$^2$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—R$^5$, -(substituted alkylene)-C(O)—O—R$^5$, -alkylene-O—C(O)—R$^5$, -(substituted alkylene)-O—C(O)—R$^5$, -alkylene-O—C(O)—O—R$^5$, or -(substituted alkylene)-O—C(O)—O—R$^5$
R$^4$ is H, halogen, —OH, —O-alkyl, —O-alkylene-O—C(O)—O—R$^5$, —O—C(O)—O—R$^5$, —SH, or —NH(R$^5$);
each R$^5$, R$^6$, and R$^7$ are independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl.

Formula (J)—TLR2 Agonists [14]

The TLR agonist can be a compound according to formula (J):

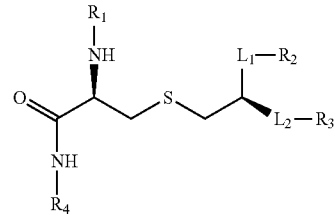

(J)

wherein:
$R^1$ is H, —C(O)—$C_7$-$C_{18}$alkyl or —C(O)—$C_1$-$C_6$alkyl;
$R^2$ is $C_7$-$C_{18}$alkyl;
$R^3$ is $C_7$-$C_{18}$alkyl;
$L_1$ is —$CH_2$OC(O)—, —$CH_2$O—, —$CH_2$NR$^7$C(O)— or —$CH_2$OC(O)NR$^7$—;
$L_2$ is —OC(O)—, —O—, —NR$^7$C(O)— or —OC(O)NR$^7$—;
$R^4$ is -$L_3R^5$ or -$L_4R^5$;
$R^5$ is —N($R^7$)$_2$, —OR$^7$, —P(O)(OR$^7$)$_2$, —C(O)OR$^7$, —NR$^7$C(O)$L_3R^8$, —NR$^7$C(O)$L_4R^8$, —O$L_3R^6$, —C(O)NR$^7L_3R^8$, —C(O)NR$^7L_4R^8$, —S(O)$_2$OR$^7$, —OS(O)$_2$OR$^7$, $C_1$-$C_6$alkyl, a $C_6$aryl, a $C_{10}$aryl, a $C_{14}$aryl, 5 to 14 ring membered heteroaryl containing 1 to 3 heteroatoms selected from O, S and N, $C_3$-$C_8$cycloalkyl or a 5 to 6 ring membered heterocycloalkyl containing 1 to 3 heteroatoms selected from O, S and N, wherein the aryl, heteroaryl, cycloalkyl and heterocycloalkyl of $R^5$ are each unsubstituted or the aryl, heteroaryl, cycloalkyl and heterocycloalkyl of $R^5$ are each substituted with 1 to 3 substituents independently selected from —OR$^9$, —O$L_3R^6$, —O$L_4R^6$, —OR$^7$, and —C(O)OR$^7$;
$L_3$ is a $C_1$-$C_{10}$alkylene, wherein the $C_1$-$C_{10}$alkylene of $L_3$ is unsubstituted, or the $C_1$-$C_{10}$alkylene of $L_3$ is substituted with 1 to 4 $R^6$ groups, or the $C_1$-$C_{10}$alkylene of $L_3$ is substituted with 2 $C_1$-$C_6$alkyl groups on the same carbon atom which together, along with the carbon atom they are attached to, form a $C_3$-$C_8$cycloalkyl;
$L_4$ is —(($CR^7R^7$)$_p$O)$_q$($CR^{10}R^{10}$)$_p$— or —($CR^{11}R^{11}$)(($CR^7R^7$)$_p$O)$_q$($CR^{10}R^{10}$)$_p$—, wherein each $R^{11}$ is a $C_1$-$C_6$alkyl groups which together, along with the carbon atom they are attached to, form a $C_3$-$C_8$cycloakyl;
each $R^6$ is independently selected from halo, $C_1$-$C_6$alkyl, $C_1$-$C_6$alkyl substituted with 1-2 hydroxyl groups, —OR$^7$, —N($R^7$)$_2$, —C(O)OH, —C(O)N($R^7$)$_2$, —P(O)(OR$^7$)$_2$, a $C_6$aryl, a $C_{10}$aryl and a $C_{14}$aryl;
each $R^7$ is independently selected from H and $C_1$-$C_6$alkyl;
$R^8$ is selected from —SR$^7$, —C(O)OH, —P(O)(OR$^7$)$_2$, and a 5 to 6 ring membered heterocycloalkyl containing 1 to 3 heteroatoms selected from O and N;
$R^9$ is phenyl;
each $R^{10}$ is independently selected from H and halo;
each p is independently selected from 1, 2, 3, 4, 5 and 6, and q is 1, 2, 3 or 4.
Preferably $R^5$ is P(O)(OR$^7$)$_2$, —NR$^7$C(O)$L_3$-P(O)(OR$^7$)$_2$, —NR$^7$C(O)$L_4$-P(O)(OR$^7$)$_2$, —O$L_3$-P(O)(OR$^7$)$_2$, —C(O)NR$^7L_3$-P(O)(OR$^7$)$_2$, or —C(O)NR$^7L_4$-P(O)(OR$^7$)$_2$.
In some embodiments of (J), $R_1$ is H. In other embodiments of (J), $R_1$ is —C(O)—$C_{15}$alkyl;
In some embodiments of (J): (i) $L_1$ is —$CH_2$OC(O)— and $L_2$ is —OC(O)—, —O—, —NR$^7$C(O)— or —OC(O)NR$^7$—; or (ii) or $L_1$ is —$CH_2$O— and $L_2$ is —OC(O)—, —O—, —NR$^7$C(O)— or —OC(O)NR$^7$—; or (iii) $L_1$ is —$CH_2$NR$^7$C(O)— and $L_2$ is —OC(O)—, —O—, —NR$^7$C(O)— or —OC(O)NR$^7$—; or (iv) $L_1$ is —$CH_2$OC(O)NR$^7$— and $L_2$ is —OC(O)—, —O—, NR$^7$C(O)— or —OC(O)NR$^7$—.
In some embodiments of (J): (i) $L_1$ is —$CH_2$OC(O)— and $L_2$ is —OC(O)—; or (ii) $L_1$ is —$CH_2$O— and $L_2$ is —O—; or (iii) $L_1$ is —$CH_2$O— and $L_2$ is —NHC(O)—; or (iv) $L_1$ is —$CH_2$OC(O)NH— and $L_2$ is —OC(O)NH—.
In some embodiments of (J), (i) $R^2$ is —$C_{11}$alkyl and $R^3$ is —$C_{11}$alkyl; or (ii) $R^2$ is —$C_{16}$alkyl and $R^3$ is —$C_{16}$alkyl; or (iii) $R^2$ is —$C_{16}$alkyl and $R^3$ is —$C_{11}$alkyl; or (iv) $R^2$ is —$C_{12}$alkyl and $R^3$ is —$C_{12}$alkyl; or (v) $R^2$ is —$C_7$alkyl and $R^3$ is —$C_7$alkyl; or (vi) $R^2$ is —$C_9$alkyl and $R^3$ is —$C_9$alkyl; or (vii) $R^2$ is —$C_8$alkyl and $R^3$ is —$C_8$alkyl; or (viii) $R^2$ is —$C_{13}$alkyl and $R^3$ is —$C_{13}$alkyl; or (ix) $R^2$ is —$C_{12}$alkyl and $R^3$ is —$C_{11}$alkyl; or (x) $R^2$ is —$C_{12}$alkyl and $R^3$ is —$C_{12}$alkyl; or (xi) $R^2$ is —$C_{10}$alkyl and $R^3$ is —$C_{10}$alkyl; or (xii) $R^2$ is —$C_{15}$alkyl and $R^3$ is —$C_{15}$alkyl.
In some embodiments of (J), $R^2$ is —$C_{11}$alkyl and $R^3$ is —$C_{11}$alkyl.

In some embodiments of (J), $L_3$ is a $C_1$-$C_{10}$alkylene, wherein the $C_1$-$C_{10}$alkylene of $L_3$ is unsubstituted or is substituted with 1 to 4 $R^6$ groups.
In some embodiments of (J): $L_4$ is —(($CR^7R^7$)$_p$O)$_q$($CR^{10}R^{10}$)$_p$—; each $R^{10}$ is independently selected from H and F; and each p is independently selected from 2, 3, and 4.
In some embodiments of (J), each $R^6$ is independently selected from methyl, ethyl, i-propyl, i-butyl, —$CH_2$OH, —OH, —F, —$NH_2$, —C(O)OH, —C(O)$NH_2$, —P(O)(OH)$_2$ and phenyl.
In some embodiments of (J), each $R^7$ is independently selected from H, methyl and ethyl.

TLR4 Agonists

Compositions of the invention can include a TLR4 agonist, and most preferably an agonist of human TLR4. TLR4 is expressed by cells of the innate immune system, including conventional dendritic cells and macrophages [15]. Triggering via TLR4 induces a signalling cascade that utilizes both the MyD88- and TRIF-dependent pathways, leading to NF-κB and IRF3/7 activation, respectively. TLR4 activation typically induces robust IL-12p70 production and strongly enhances Th1-type cellular and humoral immune responses.

Various useful TLR4 agonists are known in the art, many of which are analogs of endotoxin or lipopolysaccharide (LPS). For instance, the TLR4 agonist can be:
(i) 3d-MPL (i.e. 3-O-deacylated monophosphoryl lipid A; also known as 3-de-O-acylated monophosphoryl lipid A or 3-O-desacyl-4'-monophosphoryl lipid A). This derivative of the monophosphoryl lipid A portion of endotoxin has a de-acylated position 3 of the reducing end of glucosamine. It has been prepared from a heptoseless mutant of *Salmonella minnesota*, and is chemically similar to lipid A but lacks an acid-labile phosphoryl group and a base-labile acyl group. Preparation of 3d-MPL was originally described in ref. 16, and the product has been manufactured and sold by Corixa Corporation. It is present in GSK's 'AS04' adjuvant. Further details can be found in references 17 to 20.
(ii) glucopyranosyl lipid A (GLA) [21] or its ammonium salt:

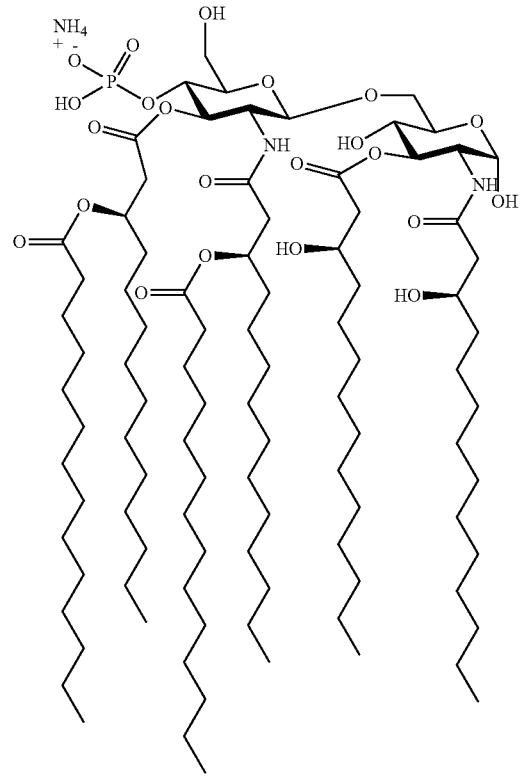

(iii) an aminoalkyl glucosaminide phosphate, such as RC/529 or CRX-524 [22-24]. RC-529 and CRX-524 have the following structure, differing by their $R_2$ groups:

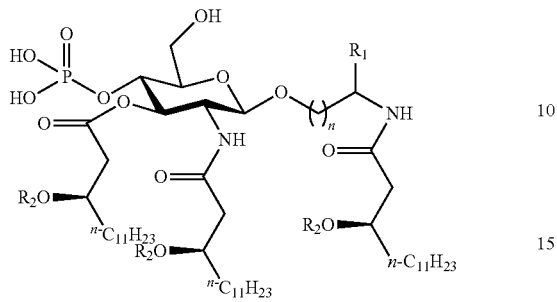

$R_1 = H, R_2 = n\text{-}C_{13}H_{27}CO, n = 1$ (RC-529)
$R_1 = H, R_2 = n\text{-}C_9H_{19}CO, n = 1$ (CRX-524)

(iv) compounds containing lipids linked to a phosphate-containing acyclic backbone, such as the TLR4 antagonist E5564 [25,26]:

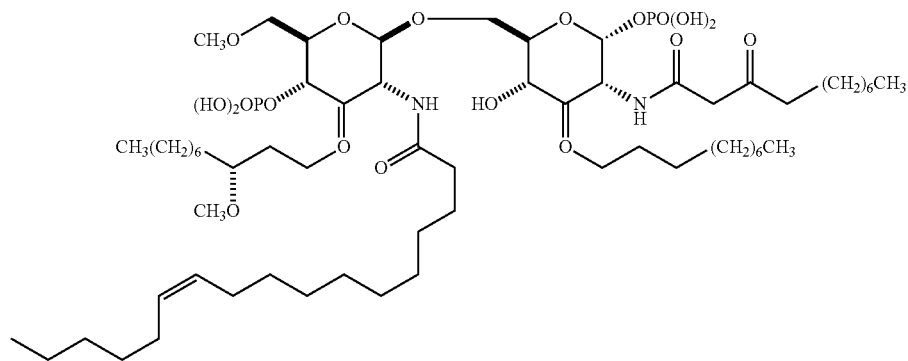

(v) A compound of formula I, II or III as defined in reference 27, or a salt thereof, such as compounds 'ER 803058', 'ER 803732', 'ER 804053', 'ER 804058', 'ER 804059', 'ER 804442', 'ER 804680', 'ER 803022', 'ER 804764' or 'ER 804057'. ER 804057 is also known as E6020 and it has the following structure:

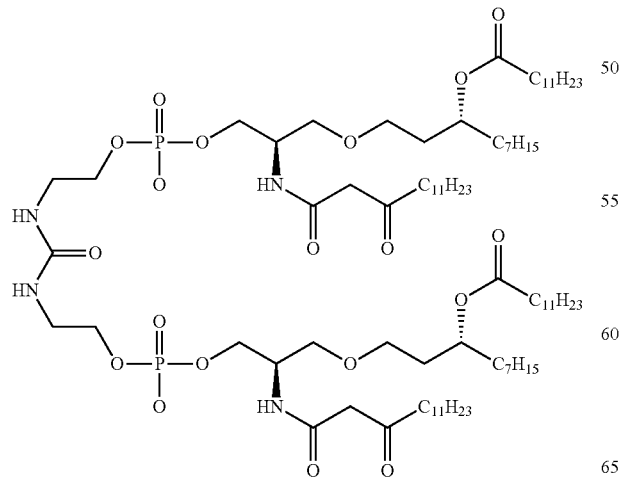

whereas ER 803022 has the following structure:

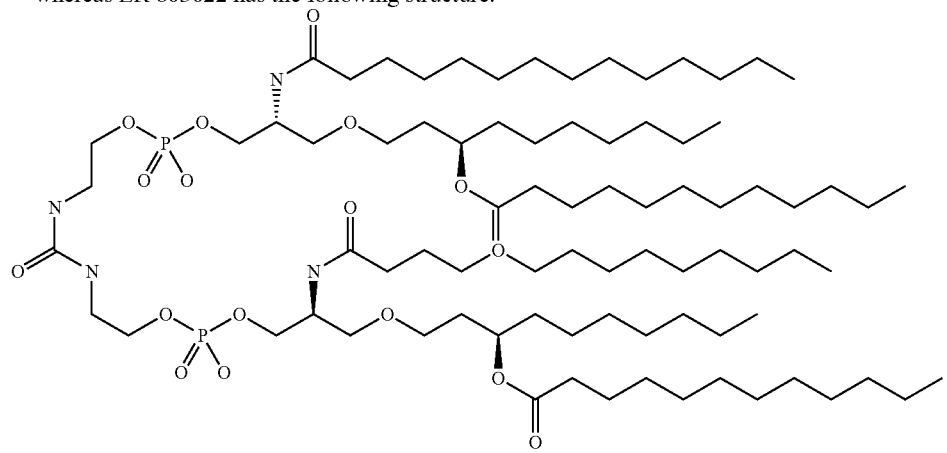

(vi) One of the polypeptide ligands disclosed in reference 28.

Any of these TLR4 agonists can be used with the invention.

A composition of the invention can include an aluminium salt to which the TLR4 agonist is adsorbed. TLR4 agonists with adsorptive properties typically include a phosphorus-containing moiety which can undergo ligand exchange with surface groups on an aluminium salt, and particularly with a salt having surface hydroxide groups. Thus a useful TLR4 agonist may include a phosphate, a phosphonate, a phosphinate, a phosphonite, a phosphinite, a phosphate, etc. Preferred TLR4 agonists include at least one phosphate group [13] e.g. the agonists (i) to (v) listed above.

The preferred TLR4 agonist for use with the invention is 3d-MPL. This can be adsorbed to an aluminium phosphate adjuvant, to an aluminium hydroxide adjuvant, or to a mixture of both [29].

3d-MPL can take the form of a mixture of related molecules, varying by their acylation (e.g. having 3, 4, 5 or 6 acyl chains, which may be of different lengths). The two glucosamine (also known as 2-deoxy-2-amino-glucose) monosaccharides are N-acylated at their 2-position carbons (i.e. at positions 2 and 2'), and there is also O-acylation at the 3' position. The group attached to carbon 2 has formula —NH—CO—CH$_2$—CR$^1$R$^{1'}$. The group attached to carbon 2' has formula —NH—CO—CH$_2$—CR$^2$R$^{2'}$. The group attached to carbon 3' has formula —O—CO—CH$_2$—CR$^3$R$^{3'}$. A representative structure is:

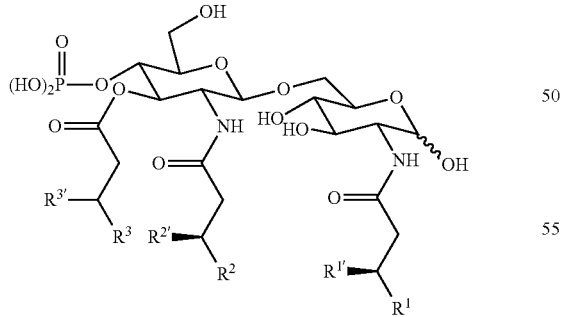

Groups R$^1$, R$^2$ and R$^3$ are each independently —(CH$_2$)$_n$—CH$_3$. The value of n is preferably between 8 and 16, more preferably between 9 and 12, and is most preferably 10.

Groups R$^{1'}$, R$^{2'}$ and R$^{3'}$ can each independently be: (a) —H; (b) —OH; or (c) —O—CO—R$^4$, where R$^4$ is either —H or —(CH$_2$)$_m$—CH$_3$, wherein the value of m is preferably between 8 and 16, and is more preferably 10, 12 or 14. At the 2 position, m is preferably 14. At the 2' position, m is preferably 10. At the 3' position, m is preferably 12. Groups R$^{1'}$, R$^{2'}$ and R$^{3'}$ are thus preferably —O-acyl groups from dodecanoic acid, tetradecanoic acid or hexadecanoic acid.

When all of R$^{1'}$, R$^{2'}$ and R$^{3'}$ are —H then the 3d-MPL has only 3 acyl chains (one on each of positions 2, 2' and 3'). When only two of R$^{1'}$, R$^{2'}$ and R$^{3'}$ are —H then the 3d-MPL can have 4 acyl chains. When only one of R$^{1'}$, R$^{2'}$ and R$^{3'}$ is —H then the 3d-MPL can have 5 acyl chains. When none of R$^{1'}$, R$^{2'}$ and R$^{3'}$ is —H then the 3d-MPL can have 6 acyl chains. The 3d-MPL used according to the invention can be a mixture of these forms, with from 3 to 6 acyl chains, but it is preferred to include 3d-MPL with 6 acyl chains in the mixture, and in particular to ensure that the 6 acyl chain form makes up at least 10% by weight of the total 3d-MPL e.g. ≥20%, ≥30%, ≥40%, ≥50% or more. 3d-MPL with 6 acyl chains has been found to be the most adjuvant-active form.

Thus the most preferred form of 3d-MPL for use with the invention is:

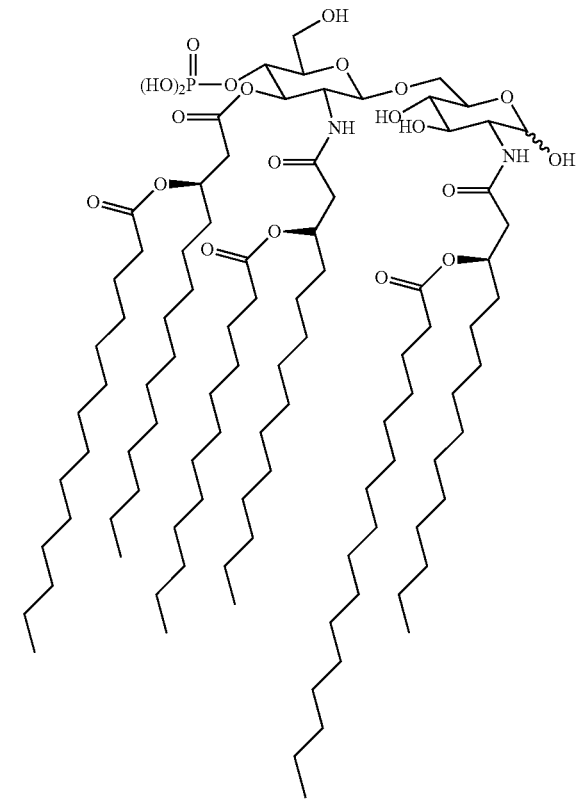

Where 3d-MPL is used in the form of a mixture then references to amounts or concentrations of 3d-MPL in compositions of the invention refer to the combined 3d-MPL species in the mixture.

Typical compositions include 3d-MPL at a concentration of between 25 µg/ml and 200 µg/ml e.g. in the range 50-150 µg/ml, 75-125 µg/ml, 90-110 µg/ml, or about 100 µg/ml. It is usual to administer between 25-75 µg of 3d-MPL per dose e.g. between 45-55 µg, or about 50 µg 3d-MPL per dose.

In aqueous conditions, 3d-MPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3d-MPL) are preferred for use according to the invention because of their superior activity [30]. Preferred particles have a mean diameter less than 150 nm, more preferably less than 120 nm, and can even have a mean diameter less than 100 nm. In most cases, however, the mean diameter will not be lower than 50 nm. Where 3d-MPL is adsorbed to an aluminum salt then it may not be possible to measure the 3D-MPL particle size directly, but particle size can be measured before adsorption takes place. Particle diameter can be assessed by the routine technique of dynamic light scattering, which reveals a mean particle diameter. Where a particle is said to have a diameter of x nm, there will generally be a distribution of particles about this mean, but at least 50% by number (e.g. ≥60%, ≥70%, ≥80%, ≥90%, or more) of the particles will have a diameter within the range x±25%.

Formula (K) [31]

The TLR agonist can be a compound according to formula (K):

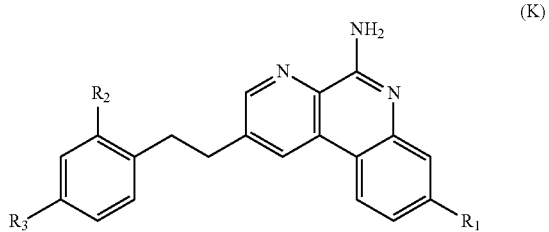

wherein:
$R^1$ is H, $C_1$-$C_6$alkyl, —$C(R^5)_2$OH, -$L^1R^5$, -$L^1R^6$, -$L^2R^5$, -$L^2R^6$, —$OL^2R^5$, or —$OL^2R^6$;
$L^1$ is —C(O)— or —O—;
$L^2$ is $C_1$-$C_6$alkylene, $C_2$-$C_6$alkenylene, arylene, heteroarylene or —$((CR^4R^4)_pO)_q(CH_2)_p$-, wherein the $C_1$-$C_6$alkylene and $C_2$-$C_6$alkenylene of $L^2$ are optionally substituted with 1 to 4 fluoro groups;
each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;
$L^4$ is arylene or heteroarylene;
$R^2$ is H or $C_1$-$C_6$alkyl;
$R^3$ is selected from $C_1$-$C_4$alkyl, -$L^3R^5$, -$L^1R^5$, -$L^3R^7$, -$L^3L^4L^3R^7$, -$L^3L^4R^5$, -$L^3L^4L^3R^5$, -$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2$OH;
each $R^4$ is independently selected from H and fluoro;
$R^5$ is —$P(O)(OR^9)_2$;
$R^6$ is —$CF_2P(O)(OR^9)_2$ or —$C(O)OR^{10}$;
$R^7$ is —$CF_2P(O)(OR^9)_2$ or —$C(O)OR^{10}$;
$R^8$ is H or $C_1$-$C_4$alkyl;
each $R^9$ is independently selected from H and $C_1$-$C_6$alkyl;
$R^{10}$ is H or $C_1$-$C_4$alkyl;
each p is independently selected from 1, 2, 3, 4, 5 and 6, and q is 1, 2, 3 or 4.

The compound of formula (K) is preferably of formula (K'):

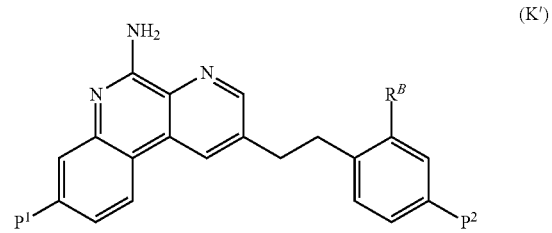

wherein:
$P^1$ is selected from H, $C_1$-$C_6$alkyl optionally substituted with COOH and —Y-L-X—$P(O)(OR^X)(OR^Y)$;
$P^2$ is selected from H, $C_1$-$C_6$alkyl, $C_1$-$C_6$alkoxy and —Y-L-X—$P(O)(OR^X)(OR^Y)$;
with the proviso that at least one of $P^1$ and $P^2$ is —Y-L-X—$P(O)(OR^X)(OR^Y)$;
$R^B$ is selected from H and $C_1$-$C_6$alkyl;
$R^X$ and $R^Y$ are independently selected from H and $C_1$-$C_6$alkyl;
X is selected from a covalent bond, O and NH;
Y is selected from a covalent bond, O, C(O), S and NH;
L is selected from, a covalent bond $C_1$-$C_6$alkylene, $C_1$-$C_6$alkenylene, arylene, heteroarylene, $C_1$-$C_6$alkyleneoxy and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$;
each p is independently selected from 1, 2, 3, 4, 5 and 6; and q is selected from 1, 2, 3 and 4.

In some embodiments of formula (K'): $P^1$ is selected from $C_1$-$C_6$alkyl optionally substituted with COOH and —Y-L-X—$P(O)(OR^X)(OR^Y)$; $P^2$ is selected from $C_1$-$C_6$alkoxy and —Y-L-X—$P(O)(OR^X)(OR^Y)$; $R^B$ is $C_1$-$C_6$alkyl; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; q is selected from 1 and 2.

Formula (F)—TLR7 Agonists [9]

The TLR agonist can be a compound according to formula (F):

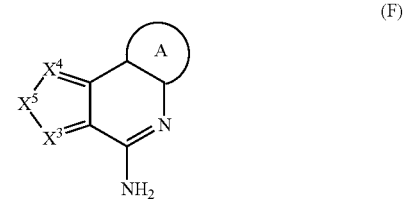

wherein:
$X^3$ is N;
$X^4$ is N or $CR^3$
$X^5$ is —$CR^4$=$CR^5$—;
$R^1$ and $R^2$ are H;
$R^3$ is H;
$R^4$ and $R^5$ are each independently selected from H, halogen, —C(O)O$R^7$, C(O)$R^7$, —C(O)N($R^{11}R^{12}$), —N($R^{11}R^{12}$), —N($R^9$)$_2$, —NHN($R^9$)$_2$, —S$R^7$, —(CH$_2$)$_n$O$R^7$, —(CH$_2$)$_n$$R^7$, -L$R^8$, -L$R^{10}$, —OL$R^8$, —OL$R^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ and $R^5$ are each optionally substituted with 1 to 3 substituents independently selected from halogen, —CN, —NO$_2$, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)R$^8$, —S(O)$_2$N(R$^9$)$_2$, and —NR$^9$S(O)$_2$R$^8$;

or, $R^3$ and $R^4$, or $R^4$ and $R^5$, or $R^5$ and $R^6$, when present on adjacent ring atoms, can optionally be linked together to form a 5-6 membered ring, wherein the 5-6 membered ring is optionally substituted with $R^7$;

each L is independently selected from a bond, —O(CH$_2$)$_m$)$_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups, and each $R^{13}$ is independently selected from halogen, —CN, -LR$^9$, -LOR$^9$, —OLR$^9$, -LR$^{10}$, -LOR$^{10}$, —OLR$^{10}$, -LR$^8$, -LOR$^8$, —OLR$^8$, -LSR$^8$, -LSR$^{10}$, —OLR$^{10}$, -LC(O)R$^8$, —OLC(O)R$^8$, -LC(O)R$^8$, -LC(O)R$^{10}$, -LOC(O)OR$^8$, -LC(O)NR$^9$R$^{11}$, -LC(O)NR$^9$R$^8$, -LN(R$^9$)$_2$, -LNR$^9$R$^8$, -LNR$^9$R$^{10}$, -LC(O)N(R$^9$)$_2$, -LS(O)$_2$R$^8$, -LS(O)R$^8$, -LC(O)NR$^8$OH, -LNR$^9$C(O)R$^8$, -LNR$^9$C(O)OR$^8$, -LS(O)$_2$N(R$^9$)$_2$, OLS(O)$_2$N(R$^9$)$_2$, -LNR$^9$S(O)$_2$R$^8$, -LC(O)NR$^9$LN(R$^9$)$_2$, -LP(O)(OR$^8$)$_2$, -LOP(O)(OR$^8$)$_2$, LP(O)(OR$^{10}$)$_2$ and —OLP(O)(OR$^{10}$)$_2$;

each $R^8$ is independently selected from H, —CH(R$^{10}$)$_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, R$^{11}$, —OR$^{11}$, —SR$^{11}$, C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each $R^9$ is independently selected from H, —C(O)R$^8$, —C(O)OR$^8$, —C(O)R$^{10}$, —C(O)OR$^{10}$, —S(O)$_2$R$^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, R$^{11}$, —OR$^{11}$, —SR$^{11}$, —C(O)R$^{11}$, OC(O)R$^{11}$, —C(O)OR$^{11}$, —NR$^{11}$R$^{12}$, —C(O)NR$^{11}$R$^{12}$, C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$ and —OP(O)(OR$^{11}$)$_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —R$^8$, —OR$^8$, -LR$^9$, -LOR$^9$, N(R$^9$)$_2$, —NR$^9$C(O)R$^8$, —NR$^9$CO$_2$R$^8$, —CO$_2$R$^8$, —C(O)R$^8$ and —C(O)N(R$^9$)$_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, R$^8$, —OR$^8$, C(O)R$^8$, OC(O)R$^8$, —C(O)OR$^8$, —N(R$^9$)$_2$, —NR$^8$C(O)R$^8$, —NR$^8$C(O)OR$^8$, —C(O)N(R$^9$)$_2$, $C_3$-$C_8$heterocycloalkyl, —S(O)$_2$R$^8$, —S(O)$_2$N(R$^9$)$_2$, —NR$^9$S(O)$_2$R$^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

ring A is an aryl or a heteroaryl, wherein the aryl and heteroaryl groups of Ring A are optionally substituted with 1 to 3 $R^4$ groups, wherein each $R^4$ is independently selected from —R$^8$, —R$^7$, —OR$^7$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH=CHCO$_2$R$^8$, —C(=NH)—N(R$^9$)$_2$, and —(CH$_2$)$_n$NHC(O)R$^8$ or two adjacent $R^4$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

Formulae (C), (D), (E), (G) and (H)

As discussed above, the TLR agonist can be of formula (C), (D), (E), (G) or (H).

The 'parent' compounds of formulae (C), (D), (E) and (H) are useful TLR7 agonists (see references 7-10 and 32-48) but are preferably modified herein by attachment of a phosphorus-containing moiety.

In some embodiments of formulae (C), (D) and (E) the compounds have structures according to formulae (C'), (D') and (E'), shown below:

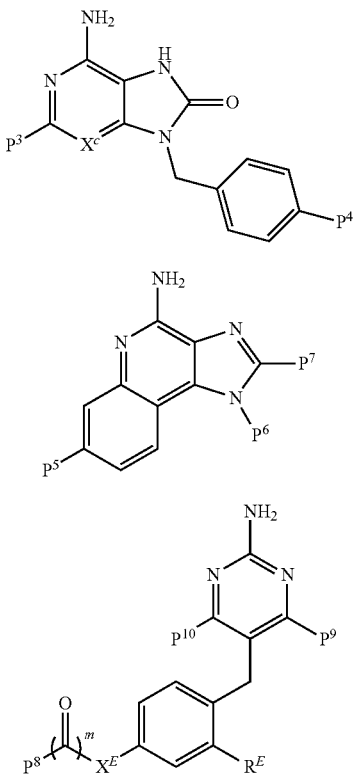

(C')

(D')

(E')

The embodiments of the invention of formulae (C), (D), (E) and (H) also apply to formulae (C'), (D'), (E') and (H').

In some embodiments of formulae (C), (D), (E), and (H): X is O; L is selected from $C_1$-$C_6$alkylene and —$((CH_2)_pO)_q$ $(CH_2)_p$— each optionally substituted with 1 to 4 substituents independently selected from halo, OH, $C_1$-$C_4$alkyl, —OP(O) $(OH)_2$ and —P(O)(OH)$_2$; each p is independently selected from 1, 2 and 3; and q is selected from 1 and 2.

In other embodiments of formula (C): $P^3$ is selected from $C_1$-$C_6$alkyl, $CF_3$, and —$((CH_2)_pO)_q(CH_2)_pO_s$— and —Y-L-X—P(O)(OR$^X$)(OR$^Y$); $P^4$ is selected from —$C_1$-$C_6$alkylaryl and —Y-L-X—P(O)(OR$^X$)(OR$^Y$); $X^C$ is CH; X is a covalent bond; L is selected from $C_1$-$C_6$alkylene and —$((CH_2)_pO)_q$ $(CH_2)_p$— each optionally substituted with 1 to 4 substituents independently selected from halo, OH, $C_1$-$C_4$alkyl, —OP(O) $(OH)_2$ and —P(O)(OH)$_2$; each p is independently selected from 1, 2 and 3; q is 1 or 2.

In other embodiments of formulae (C), (D), (E), and (H): X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (C): $P^3$ is selected from $C_1$-$C_6$alkyl, $CF_3$, and —$((CH_2)_pO)_q(CH_2)_pO_s$— and —Y-L-X—P(O)(OR$^X$)(OR$^Y$); $P^4$ is selected from —$C_1$-$C_6$alkylaryl and —Y-L-X—P(O)(OR$^X$)(OR$^Y$); $X^C$ is N; X is a covalent bond; L is selected from $C_1$-$C_6$alkylene and —$((CH_2)_pO)_q$ $(CH_2)_p$— each optionally substituted with 1 to 4 substituents independently selected from halo, OH, $C_1$-$C_4$alkyl, —OP(O) $(OH)_2$ and —P(O)(OH)$_2$; each p is independently selected from 1, 2 and 3; q is selected from 1 and 2.

In other embodiments of formula (D): $P^5$ is selected from $C_1$-$C_6$alkyl, and —Y-L-X—P(O)(OR$^X$)(OR$^Y$).

In other embodiments of formula (D): X is O; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (D): X is a covalent bond; L is selected from $C_1$-$C_6$alkylene and —$((CH_2)_pO)_q$ $(CH_2)_p$— each optionally substituted with 1 to 4 substituents independently selected from halo, OH, $C_1$-$C_4$alkyl, —OP(O) $(OH)_2$ and —P(O)(OH)$_2$; each p is independently selected from 1, 2 and 3; and q is selected from 1 and 2.

In other embodiments of formula (E): X is O; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (E): X is a covalent bond; L is selected from $C_1$-$C_6$alkylene and —$((CH_2)_pO)_q$ $(CH_2)_p$— each optionally substituted with 1 to 4 substituents independently selected from halo, OH, $C_1$-$C_4$alkyl, —OP(O) $(OH)_2$ and —P(O)(OH)$_2$; each p is independently selected from 1, 2 and 3; and q is selected from 1 and 2.

In other embodiments of formula (E): $X^E$ is $CH_2$, $P^8$ is $C_1$-$C_6$alkoxy optionally substituted with —Y-L-X—P(O) (OR$^X$)(OR$^Y$).

In other embodiments of formula (E): $P^9$ is —NHC$_1$-$C_6$alkyl optionally substituted with OH and $C_1$-$C_6$alkyl, and —Y-L-X—P(O)(OR$^X$)(OR$^Y$).

In some embodiments, a compound of formula (C) is not a compound in which $P^4$ is —Y-L-X—P(O)(OR$^X$)(OR$^Y$).

In some embodiments, in a compound of formula (C), $P^4$ is selected from H, $C_1$-$C_6$alkyl, —$C_1$-$C_6$alkylaryl.

In some embodiments of formula (H): $X^{H1}$—$X^{H2}$ is $CR^{H2}R^{H3}$, $R^{H2}$ and $R^{H3}$ are H, $X^{H3}$ is N, X is a covalent bond; L is selected from $C_1$-$C_6$alkylene and —$((CH_2)_pO)_q$ $(CH_2)_p$— each optionally substituted with 1 to 4 substituents independently selected from halo, OH, $C_1$-$C_4$alkyl, —OP(O) $(OH)_2$ and —P(O)(OH)$_2$; each p is independently selected from 1, 2 and 3; and q is selected from 1 and 2.

In some embodiments of formula (H): $X^{H1}$—$X^{H2}$ is $CR^{H2}R^{H3}$, $R^{H2}$ and $R^{H3}$ are H, $X^{H3}$ is N, X is O; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

The 'parent' compounds of formula (G) are useful TLR8 agonists (see references 11 & 12) but are preferably modified herein by attachment of a phosphorus-containing moiety to permit adsorption. In some embodiments of formula (G), the compounds have structures according to formula (G');

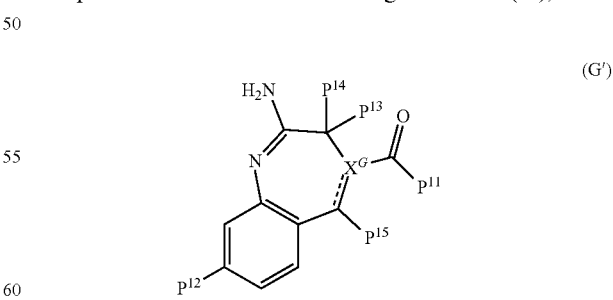

(G')

In some embodiments of formula (G) or (G'): $X^G$ is C and ----- represents a double bond.

In some embodiments of formula (G) or (G'): X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In some embodiments of formula (G) or (G'): X is O; L is selected from $C_1$-$C_6$alkylene and —((CH$_2$)$_p$O)$_q$(CH$_2$)$_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

Oil-in-Water Emulsion Adjuvants

According to the invention's second aspect a vaccine is adjuvanted with an oil-in-water emulsion. Various such emulsions are known e.g. MF59 and AS03 are both authorised in Europe.

Useful emulsion adjuvants they typically include at least one oil and at least one surfactant, with the oil(s) and surfactant(s) being biodegradable (metabolisable) and biocompatible. The oil droplets in the emulsion generally have a submicron diameter, and these small sizes can readily be achieved with a microfluidiser to provide stable emulsions, or by alternative methods e.g. phase inversion. Emulsions in which at least 80% (by number) of droplets have a diameter of less than 220 nm are preferred, as they can be subjected to filter sterilization.

The emulsion can include oil(s) from an animal (such as fish) and/or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolisable and may therefore be used with the invention. The procedures for separation, purification, saponification and other means necessary for obtaining pure oils from animal sources are well known in the art.

Most fish contain metabolisable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred for use with the invention (see below). Squalane, the saturated analog to squalene, is also a useful oil. Fish oils, including squalene and squalane, are readily available from commercial sources or may be obtained by methods known in the art. Other preferred oils are the tocopherols (see below). Mixtures of oils can be used.

Preferred amounts of total oil (% by volume) in an adjuvant emulsion are between 1 and 20% e.g. between 2-10%. A squalene content of 5% by volume is particularly useful.

Surfactants can be classified by their 'HLB' (hydrophile/lipophile balance). Preferred surfactants of the invention have a HLB of at least 10 e.g. about 15. The invention can be used with surfactants including, but not limited to: the polyoxyethylene sorbitan esters surfactants (commonly referred to as the Tweens), especially polysorbate 20 or polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy(oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the Spans), such as sorbitan trioleate (Span 85) or sorbitan monolaurate.

Emulsions used with the invention preferably include nonionic surfactant(s). Preferred surfactants for including in the emulsion are polysorbate 80 (polyoxyethylene sorbitan monooleate; Tween 80), Span 85 (sorbitan trioleate), lecithin or Triton X-100. Mixtures of surfactants can be used e.g. a mixture of polysorbate 80 and sorbitan trioleate. A combination of a polyoxyethylene sorbitan ester such as polysorbate 80 (Tween 80) and an octoxynol such as t-octylphenoxypolyethoxyethanol (Triton X-100) is also useful. Another useful combination comprises laureth 9 plus a polyoxyethylene sorbitan ester and/or an octoxynol. Where a mixture of surfactants is used then the HLB of the mixture is calculated according to their relative weightings (by volume) e.g. the preferred 1:1 mixture by volume of polysorbate 80 and sorbitan trioleate has a HLB of 8.4.

Preferred amounts of total surfactant (% by volume) in an adjuvant emulsion are between 0.1 and 2% e.g. between 0.25-2%. A total content of 1% by volume is particularly useful e.g. 0.5% by volume of polysorbate 80 and 0.5% by volume of sorbitan trioleate.

Useful emulsions can be prepared using known techniques e.g. see references 3 and 49-55.

Specific oil-in-water emulsion adjuvants useful with the invention include, but are not limited to:

- A submicron emulsion of squalene, polysorbate 80, and sorbitan trioleate. The composition of the emulsion by volume can be about 5% squalene, about 0.5% polysorbate 80 and about 0.5% sorbitan trioleate. In weight terms, these ratios become 4.3% squalene, 0.5% polysorbate 80 and 0.48% sorbitan trioleate. This adjuvant is known as 'MF59' [56-58], as described in more detail in Chapter 10 of ref. 2 and chapter 12 of ref. 3. The MF59 emulsion advantageously includes citrate ions e.g. 10 mM sodium citrate buffer.
- An emulsion of squalene, a tocopherol, and polysorbate 80. The emulsion may include phosphate buffered saline. These emulsions may have from 2 to 10% squalene, from 2 to 10% tocopherol and from 0.3 to 3% polysorbate 80, and the weight ratio of squalene:tocopherol is preferably ≤1 (e.g. 0.90) as this can provide a more stable emulsion. Squalene and polysorbate 80 may be present volume ratio of about 5:2, or at a weight ratio of about 11:5. Thus the three components (squalene, tocopherol, polysorbate 80) may be present at a weight ratio of 1068:1186:485 or around 55:61:25. This adjuvant is known as 'AS03'. Another useful emulsion of this type may comprise, per human dose, 0.5-10 mg squalene, 0.5-11 mg tocopherol, and 0.1-4 mg polysorbate 80 [59] e.g. in the ratios discussed above.
- An emulsion in which a saponin (e.g. QuilA or QS21) and a sterol (e.g. a cholesterol) are associated as helical micelles [60].
- An emulsion having from 0.5-50% of an oil, 0.1-10% of a phospholipid, and 0.05-5% of a non-ionic surfactant. As described in reference 61, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.
- An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/ or has at least 90% of the oil droplets (by volume) with a size less than 200 nm [62]. The emulsion may also include one or more of: alditol; a cryoprotective agent (e.g. a sugar, such as dodecylmaltoside and/or sucrose); and/or an alkylpolyglycoside. It may also include a TLR4 agonist, such as one whose chemical structure does not include a sugar ring [63]. Such emulsions may be lyophilized. The 'AF03' product is one such emulsion.

Preferred oil-in-water emulsions used with the invention comprise squalene and polysorbate 80.

The emulsions may be mixed with TdaP antigens during vaccine manufacture, or they may be mixed extemporaneously at the time of delivery. Thus, in some embodiments, the adjuvant and antigens may be kept separately in a packaged or distributed vaccine, ready for final formulation at the time of use. At the time of mixing (whether during bulk manufacture, or at the point of use) the antigen will generally be in an aqueous form, such that the final vaccine is prepared by mixing two liquids. The volume ratio of the two liquids for mixing can vary (e.g. between 5:1 and 1:5) but is generally about 1:1. If emulsion and antigen are stored separately in a kit then the product may be presented as a vial containing emulsion and a vial containing aqueous antigen, for mixing to give adjuvanted liquid vaccine (monodose or multidose).

Preferred emulsions of the invention include squalene oil. This is usually prepared from shark oil but alternative sources are known e.g. see references 64 (yeast) and 65 (olive oil). Squalene which contains less than 661 picograms of PCBs per gram of squalene (TEQ) is preferred for use with the invention, as disclosed in reference 66. The emulsions are preferably made from squalene of high purity e.g. prepared by double-distillation as disclosed in reference 67.

Where a composition includes a tocopherol, any of the α, β, γ, δ, ε or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols have antioxidant properties that may help to stabilize the emulsions [68]. A preferred α-tocopherol is DL-α-tocopherol, and a preferred salt of this tocopherol is the succinate.

Diphtheria Toxoid

Diphtheria is caused by *Corynebacterium diphtheriae*, a Gram-positive non-sporing aerobic bacterium. This organism expresses a prophage-encoded ADP-ribosylating exotoxin ('diphtheria toxin'), which can be treated (e.g. using formaldehyde) to give a toxoid that is no longer toxic but that remains antigenic and is able to stimulate the production of specific anti-toxin antibodies after injection. Diphtheria toxoids are disclosed in more detail in chapter 13 of reference 69. Preferred diphtheria toxoids are those prepared by formaldehyde treatment. The diphtheria toxoid can be obtained by growing *C. diphtheriae* in growth medium (e.g. Fenton medium, or Linggoud & Fenton medium), which may be supplemented with bovine extract, followed by formaldehyde treatment, ultrafiltration and precipitation. The toxoided material may then be treated by a process comprising sterile filtration and/or dialysis.

Quantities of diphtheria toxoid can be expressed in international units (IU). For example, the NIBSC [70] supplies the 'Diphtheria Toxoid Adsorbed Third International Standard 1999' [71,72], which contains 160 IU per ampoule. As an alternative to the IU system, the 'Lf' unit ("flocculating units", the "limes flocculating dose", or the "limit of flocculation") is defined as the amount of toxoid which, when mixed with one International Unit of antitoxin, produces an optimally flocculating mixture [73]. For example, the NIBSC supplies 'Diphtheria Toxoid, Plain' [74], which contains 300 Lf per ampoule and 'The 1st International Reference Reagent For Diphtheria Toxoid For Flocculation Test' [75] which contains 900 Lf per ampoule. The concentration of diphtheria toxin in a composition can readily be determined using a flocculation assay by comparison with a reference material calibrated against such reference reagents. The conversion between IU and Lf systems depends on the particular toxoid preparation.

The concentration of diphtheria toxoid in a composition of the invention is typically in the range of 2-8 Lf/ml (e.g. 4 Lf/ml or 5 Lf/ml), but is ideally ≤4 Lf/ml. In a typical 0.5 ml unit dose volume, therefore, the amount of diphtheria toxoid can be 2 Lf, 2.5 Lf, or less than 2 Lf.

Diphtheria toxoid in the composition is preferably adsorbed (more preferably totally adsorbed) onto an aluminium salt, preferably onto an aluminium hydroxide adjuvant.

Tetanus Toxoid

Tetanus is caused by *Clostridium tetani*, a Gram-positive, spore-forming *bacillus*. This organism expresses an endopeptidase ('tetanus toxin'), which can be treated to give a toxoid that is no longer toxic but that remains antigenic and is able to stimulate the production of specific anti-toxin antibodies after injection. Tetanus toxoids are disclosed in more detail in chapter 27 of reference 69. Preferred tetanus toxoids are those prepared by formaldehyde treatment. The tetanus toxoid can be obtained by growing *C. tetani* in growth medium (e.g. a Latham medium derived from bovine casein), followed by formaldehyde treatment, ultrafiltration and precipitation. The material may then be treated by a process comprising sterile filtration and/or dialysis.

Quantities of tetanus toxoid can be expressed in international units (IU). For example, NIBSC supplies the 'Tetanus Toxoid Adsorbed Third International Standard 2000' [76,77], which contains 469 IU per ampoule. As with diphtheria toxoid, the 'Lf' unit is an alternative to the IU system. NIBSC supplies 'The 1st International Reference Reagent for Tetanus Toxoid For Flocculation Test' [78] which contains 1000 LF per ampoule. The concentration of diphtheria toxin in a composition can readily be determined using a flocculation assay by comparison with a reference material calibrated against such reference reagents.

The concentration of tetanus toxoid in a composition of the invention is typically in the range of 5-15 Lf/ml (e.g. 10 Lf/ml), but is ideally ≤9 Lf/ml. In a typical 0.5 ml unit dose volume, therefore, the amount of diphtheria toxoid can be 5 Lf, or less than 4.5 Lf.

Tetanus toxoid in the composition is preferably adsorbed (sometimes totally adsorbed) onto that salt, preferably onto an aluminium hydroxide adjuvant.

Pertussis Toxoid

*Bordetella pertussis* causes whooping cough. Pertussis antigens in vaccines are either cellular (whole cell, in the form of inactivated *B. pertussis* cells; 'wP') or acellular ('aP'). Preparation of cellular pertussis antigens is well documented (e.g. see chapter 21 of reference 69) e.g. it may be obtained by heat inactivation of phase I culture of *B. pertussis*. The invention preferably uses acellular antigens, including, one, two or (preferably) three of the following three antigens: (1) detoxified pertussis toxin (pertussis toxoid, or 'PT'); (2) filamentous hemagglutinin ('FHA'); (3) pertactin (also known as the '69 kiloDalton outer membrane protein'). These three antigens can be prepared by isolation from *B. pertussis* culture grown in modified Stainer-Scholte liquid medium. PT and FHA can be isolated from the fermentation broth (e.g. by adsorption on hydroxyapatite gel), whereas pertactin can be extracted from the cells by heat treatment and flocculation (e.g. using barium chloride). The antigens can be purified in successive chromatographic and/or precipitation steps. PT and FHA can be purified by hydrophobic chromatography, affinity chromatography and size exclusion chromatography. Pertactin can be purified by ion exchange chromatography, hydrophobic chromatography and size exclusion chromatography, or by IMAC. FHA and pertactin may be treated with formaldehyde prior to use according to the invention. PT is preferably detoxified by treatment with formaldehyde and/or glutaraldehyde. As an alternative to this chemical detoxification procedure the PT may be a mutant PT in which enzymatic activity has been reduced by mutagenesis [79](e.g. the 9K/129G double mutant [80]).

The invention preferably uses a PT-containing aP antigen. When using an aP antigen a composition of the invention will typically, in addition to the PT, include FHA and, optionally, pertactin. It can also optionally include fimbriae types 2 and 3.

Quantities of acellular pertussis antigens are typically expressed in micrograms. The concentration of pertussis toxoid in a composition of the invention is typically in the range of 2-20 µg/ml (e.g. 5 µg/ml or 16 µg/ml), but is ideally ≤4 µg/ml. In a typical 0.5 ml unit dose volume, therefore, the amount of diphtheria toxoid can be 2.5 µg, 8 µg, or <2 µg.

It is usual that each of pertussis toxoid, FHA and pertactin are present in a composition of the invention. These may be present at various ratios (by mass), such as PT:FHA:p69 ratios of 16:16:5 or 5:10:6. Each of these three antigens will generally be present at <20 µg/ml e.g. in the range of 4-20 µg/ml. A total pertussis antigen concentration of <40 µg/ml is typical. It is usual to have a mass excess of FHA relative to pertactin.

Pertussis toxin in the composition is preferably adsorbed (sometimes totally adsorbed) onto that salt, preferably onto an aluminium hydroxide adjuvant. Any FHA can also be adsorbed to an aluminium hydroxide adjuvant. Any pertactin can be adsorbed to an aluminium phosphate adjuvant.

Inactivated Poliovirus Antigen (IPV)

Poliomyelitis can be caused by one of three types of poliovirus. The three types are similar and cause identical symptoms, but they are antigenically very different and infection by one type does not protect against infection by others. As explained in chapter 24 of reference 69, it is therefore preferred to use three poliovirus antigens with the invention—poliovirus Type 1 (e.g. Mahoney strain), poliovirus Type 2 (e.g. MEF-1 strain), and poliovirus Type 3 (e.g. Saukett strain). As an alternative to these strains ("Salk" strains), Sabin strains of types 1 to 3 can be used e.g. as discussed in references 81 & 82. These strains can be more potent than the normal Salk strains.

Polioviruses may be grown in cell culture. A preferred culture uses a Vero cell line, which is a continuous cell line derived from monkey kidney. Vero cells can conveniently be cultured microcarriers. Culture of the Vero cells before and during viral infection may involve the use of bovine-derived material, such as calf serum, and of lactalbumin hydrolysate (e.g. obtained by enzymatic degradation of lactalbumin). Such bovine-derived material should be obtained from sources which are free from BSE or other TSEs. The final vaccine preferably contains less than 10 ng/ml, preferably ≤1 ng/ml e.g. ≤500 pg/ml or ≤50 pg/ml of Vero cell DNA e.g. less than 10 ng/ml of Vero cell DNA that is ≥50 base pairs long.

After growth, virions may be purified using techniques such as ultrafiltration, diafiltration, and chromatography. Prior to administration to patients, polioviruses must be inactivated, and this can be achieved by treatment with formaldehyde before the viruses are used in the process of the invention.

The viruses are preferably grown, purified and inactivated individually, and are then combined to give a bulk mixture for use with the invention.

Quantities of inactivated poliovirus (IPV) are typically expressed in the 'DU' unit (the "D-antigen unit" [83]). Typically a composition has IPV antigens 1/2/3 at concentrations of 80/16/64 DU/ml (40/8/32 DU per 0.5 ml dose). In some embodiments, however, a composition can include lower amounts of poliovirus antigens, either through including less antigen or by using more potent strains. For a Type 1 poliovirus the concentration of the virus in the composition can be ≤20 DU/ml e.g. <18, <16, <14, <12, <10, etc. For a Type 2 poliovirus the concentration of the virus in the composition can be ≤4 DU/ml e.g. <3, <2, <1, <0.5, etc. For a Type 3 poliovirus the concentration of the virus in the composition can be ≤16 DU/ml e.g. <14, <12, <10, <8, <6, etc. Where all three of Types 1, 2 and 3 poliovirus are present the three antigens can be present at a DU ratio of 5:1:4 respectively, or at any other suitable ratio e.g. a ratio of 15:32:45 when using Sabin strains [81]. A low dose of antigen from Sabin strains is particularly useful, with ≤10 DU type 1, ≤20 DU type 2, and ≤30 DU type 3 (per unit dose).

Polioviruses are preferably not adsorbed to any adjuvant before they are formulated, but after formulation they may become adsorbed onto aluminium salt(s) in the composition.

Combination Vaccines

As well as including D, T, Pa, and/or poliovirus antigens, immunogenic compositions of the invention may include antigens from further pathogens. For example, these antigens may be HBsAg, conjugated Hib capsular saccharide, conjugated *N. meningitidis* capsular saccharide (one or more of serogroups A, C, W135 and/or Y) or conjugated *S. pneumoniae* capsular saccharide. For example, any of the suitable antigen components of PEDIARIX, MENVEO, MENACTRA, NIMENRIX, PREVNAR, or SYNFLORIX can be used.

Preferably, however, the vaccine's only antigenic components are either (i) for diphtheria, tetanus and pertussis or (ii) for diphtheria, tetanus, pertussis and poliovirus.

Immunogenic compositions of the invention include at least a diphtheria toxoid, a tetanus toxoid, and a pertussis toxoid as immunogenic components. The compositions include an excess of tetanus toxoid relative to diphtheria toxoid. This excess is measured in Lf units (but the excess can also be seen via IU e.g. Adacel's content is quoted as 5 Lf of tetanus toxoid and 2 Lf of diphtheria toxoid, or as 20 IU of tetanus toxoid and 2 IU of diphtheria toxoid). The excess is ideally at least 1.5:1 (i.e. at least 1.5 Lf of tetanus toxoid for every 1 Lf of diphtheria toxoid) e.g. 2:1 or 2.5:1. The excess will not usually be more than 5-fold (again, in Lf units).

As an independent embodiment of the disclosure, the invention provides an immunogenic composition comprising an acellular pertussis component in which a pertussis toxoid (e.g. the PT-9K/129G double mutant), filamentous hemagglutinin and pertactin are present at a mass ratio of 1:1:2. For instance, the composition can comprise 4 μg pertussis toxoid, 4 μg FHA and 8 μg pertactin per unit dose. The composition can also include diphtheria toxoid (e.g. 2 Lf per unit dose) and tetanus toxoid (e.g. 5 Lf per dose) to provide a TdaP combination. The composition can also include an adjuvant comprising an aluminium salt (e.g. an aluminium hydroxide) and, optionally, a TLR agonist as described elsewhere herein.

Pharmaceutical Compositions and Products

The invention provides various immunogenic compositions. These are ideally pharmaceutical compositions suitable for use in humans. Pharmaceutical compositions usually include components in addition to the immunogen and the adjuvant components e.g. they typically include one or more pharmaceutical carrier(s) and/or excipient(s). A thorough discussion of such components is available in reference 84.

Pharmaceutical compositions are preferably in aqueous form, particularly at the point of administration, but they can also be presented in non-aqueous liquid forms or in dried forms e.g. as gelatin capsules, or as lyophilisates, etc.

Pharmaceutical compositions may include one or more preservatives, such as thiomersal or 2-phenoxyethanol. Mercury-free compositions are preferred, and preservative-free vaccines can be prepared.

Pharmaceutical compositions can include a physiological salt, such as a sodium salt e.g. to control tonicity. Sodium chloride (NaCl) is typical, which may be present at between 1 and 20 mg/ml e.g. 10±2 mg/ml or 9 mg/ml. Other salts that may be present include potassium chloride, potassium dihydrogen phosphate, disodium phosphate dehydrate, magnesium chloride, calcium chloride, etc.

Pharmaceutical compositions can have an osmolality of between 200 mOsm/kg and 400 mOsm/kg, e.g. between 240-360 mOsm/kg, or between 290-310 mOsm/kg. Compositions may be isotonic with humans.

Pharmaceutical compositions may include compounds (with or without an insoluble aluminium salt) in plain water (e.g. w.f.i.) but will usually include one or more buffers. Typical buffers include: a phosphate buffer (except in the fifteenth aspect); a Tris buffer; a borate buffer; a succinate buffer; a histidine buffer (particularly with an aluminium hydroxide adjuvant); or a citrate buffer. Buffer salt s will typically be included in the 5-20 mM range. If a phosphate buffer is used then the concentration of phosphate ions should, in some embodiments, be <50 mM (see above) e.g. <10 mM.

The pH of a composition of the invention will generally be between 6.0 and 7.5. A manufacturing process may therefore include a step of adjusting the pH of a composition prior to packaging. Aqueous compositions administered to a patient can have a pH of between 5.0 and 7.5, and more typically between 5.0 and 6.0 for optimum stability; where a diphtheria toxoid and/or tetanus toxoid is present, the pH is ideally between 6.0 and 7.0.

Pharmaceutical compositions are preferably sterile.

Pharmaceutical compositions preferably non-pyrogenic e.g. containing <1 EU (endotoxin unit, a standard measure) per dose, and preferably <0.1 EU per dose. 1 EU is equal to 0.2 ng FDA reference standard Endotoxin EC-2 'RSE') per dose.

Pharmaceutical compositions are preferably gluten free.

During manufacture, dilution of components to give desired final concentrations will usually be performed with WFI (water for injection).

Pharmaceutical compositions are suitable for administration to animal (and, in particular, human) patients, and thus include both human and veterinary uses. They may be used in a method of raising an immune response in a patient, comprising the step of administering the composition to the patient.

The invention can provide bulk material which is suitable for packaging into individual doses, which can then be distributed for administration to patients. Concentrations discussed above are typically concentrations in final packaged dose, and so concentrations in bulk vaccine may be higher (e.g. to be reduced to final concentrations by dilution).

Pharmaceutical compositions may be prepared in unit dose form. In some embodiments a unit dose may have a volume of between 0.05-1.5 ml e.g. about 0.5 ml for intramuscular injection. References to 0.5 ml doses will be understood to include normal variance e.g. 0.5 ml±0.05 ml. For multidose situations, multiple dose amounts will be extracted and packaged together in a single container e.g. 5 ml for a 10-dose multidose container (or 5.5 ml with 10% overfill).

The invention also provides a delivery device (e.g. syringe, nebuliser, sprayer, inhaler, dermal patch, etc.) containing a pharmaceutical composition of the invention e.g. containing a unit dose. This device can be used to administer the composition to a vertebrate subject.

The invention also provides a sterile container (e.g. a vial) containing a pharmaceutical composition of the invention e.g. containing a unit dose.

The invention also provides a unit dose of a pharmaceutical composition of the invention.

The invention also provides a hermetically sealed container containing a pharmaceutical composition of the invention. Suitable containers include e.g. a vial.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition), although aqueous compositions are preferred. Suspensions for intramuscular or intradermal or subcutaneous injection are typical.

Compositions of the first aspect comprise an effective amount of a TLR agonist i.e. an amount which, when administered to an individual, either in a single dose or as part of a series, is effective for enhancing the immune response to a its co-administered immunogens. This amount can vary depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors.

The amount of TLR agonist in a unit dose of a composition will fall in a relatively broad range that can be determined through routine trials. An amount of between 1-1000 µg/dose can be used e.g. from 5-100 µg per dose or from 10-100 µg per dose, and ideally ≤300 µg per dose e.g. about 5 µg, 10 µg, 20 µg, 25 µg, 50 µg or 100 µg per dose. Thus the concentration of a TLR agonist in a composition of the invention may be from 2-2000 µg/ml e.g. from 10-200 µg/ml, or about 5, 10, 20, 40, 50, 100 or 200 µg/ml, and ideally ≤600 µg/ml.

Methods of Treatment, and Administration of Immunogenic Compositions

The invention is suitable for raising immune responses in humans, but they may also be useful in non-human animals (in particular mammals) subjects. Compositions prepared according to the invention may be used to treat both children and adults.

The invention provides a method of raising an immune response in a subject, comprising the step of administering to the subject a composition of the invention. The invention also provides a composition of the invention, for use in a method of raising an immune response in a subject. The invention also provides the use of (i) a TLR agonist as defined herein and (ii) an insoluble aluminium salt and (iii) at least diphtheria, tetanus and pertussis toxoids, in the manufacture of a medicament (e.g. a vaccine) for raising an immune response in a subject. The invention also provides the use of (i) an oil-in-water emulsion adjuvant as defined herein and (ii) at least diphtheria, tetanus and pertussis toxoids, in the manufacture of a medicament (e.g. a vaccine) for raising an immune response in a subject.

The immune response stimulated by these methods and uses will generally include an antibody response, preferably a protective antibody response. The immune response can also include a cellular response. Methods for assessing antibody and cellular immune responses after immunisation are well known in the art, particularly for diphtheria, tetanus, pertussis and poliovirus antigens.

Administration of compositions of the invention will generally be by injection, and this may be by the subcutaneous, intradermal of the intramuscular route. Intramuscular injection is preferred.

Immunogenic compositions of the invention will generally be administered to people at least 3 years of age, and preferably at least 4 years of age. For instance, the subject may be 10-64 years old, or a teenager. The compositions are most useful in people who have previously received routine childhood immunisations (including DTP vaccine).

A patient will generally receive the composition as frequently as required. Each course of immunisation will involve a single booster dose.

Chemical Groups

Unless specifically defined elsewhere, the chemical groups discussed herein have the following meaning when used in present specification:

The term "alkyl" includes saturated hydrocarbon residues including:
- linear groups up to 10 atoms ($C_1$-$C_{10}$), or of up to 6 atoms ($C_1$-$C_6$), or of up to 4 atoms ($C_1$-$C_4$). Examples of such alkyl groups include, but are not limited, to $C_1$-methyl, $C_2$-ethyl, $C_3$-propyl and $C_4$-n-butyl.
- branched groups of between 3 and 10 atoms ($C_3$-$C_{10}$), or of up to 7 atoms ($C_3$-$C_7$), or of up to 4 atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.

The term "alkylene" refers to the divalent hydrocarbon radical derived from an alkyl group, and shall be construed in accordance with the definition above.

The term "alkenyl" includes monounsaturated hydrocarbon residues including:
- linear groups of between 2 and 6 atoms ($C_2$-$C_6$). Examples of such alkenyl groups include, but are not limited to, $C_2$-vinyl, $C_3$-1-propenyl, $C_3$-allyl, $C_4$-2-butenyl
- branched groups of between 3 and 8 atoms ($C_3$-$C_8$). Examples of such alkenyl groups include, but are not limited to, $C_4$-2-methyl-2-propenyl and $C_6$-2,3-dimethyl-2-butenyl.

The term alkenylene refers to the divalent hydrocarbon radical derived from an alkenyl group, and shall be construed in accordance with the definition above.

The term "alkoxy" includes O-linked hydrocarbon residues including:
- linear groups of between 1 and 6 atoms ($C_1$-$C_6$), or of between 1 and 4 atoms ($C_1$-$C_4$). Examples of such alkoxy groups include, but are not limited to, $C_1$-methoxy, $C_2$-ethoxy, $C_3$-n-propoxy and $C_4$-n-butoxy.
- branched groups of between 3 and 6 atoms ($C_3$-$C_6$) or of between 3 and 4 atoms ($C_3$-$C_4$). Examples of such alkoxy groups include, but are not limited to, $C_3$-iso-propoxy, and $C_4$-sec-butoxy and tert-butoxy.

Halo is selected from Cl, F, Br and I. Halo is preferably F.

The term "aryl" includes a single or fused aromatic ring system containing 6 or 10 carbon atoms; wherein, unless otherwise stated, each occurrence of aryl may be optionally substituted with up to 5 substituents independently selected from ($C_1$-$C_6$)alkyl, ($C_1$-$C_6$)alkoxy, OH, halo, CN, $COOR^{14}$, $CF_3$ and $NR^{14}R^{15}$; as defined above. Typically, aryl will be optionally substituted with 1, 2 or 3 substituents. Optional substituents are selected from those stated above. Examples of suitable aryl groups include phenyl and naphthyl (each optionally substituted as stated above). Arylene refers the divalent radical derived from an aryl group, and shall be construed in accordance with the definition above.

The term "heteroaryl" includes a 5, 6, 9 or 10 membered mono- or bi-cyclic aromatic ring, containing 1 or 2 N atoms and, optionally, an $NR^{14}$ atom, or one $NR^{14}$ atom and an S or an O atom, or one S atom, or one O atom; wherein, unless otherwise stated, said heteroaryl may be optionally substituted with 1, 2 or 3 substituents independently selected from ($C_1$-$C_6$)alkyl, ($C_1$-$C_6$)alkoxy, OH, halo, CN, $COOR^{14}$, $CF_3$ and $NR^{14}R^{15}$; as defined below. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above). Heteroarylene refers the divalent radical derived from heteroaryl, and shall be construed in accordance with the definition above.

The term "heterocyclyl" is a C-linked or N-linked 3 to 10 membered non-aromatic, mono- or bi-cyclic ring, wherein said heterocycloalkyl ring contains, where possible, 1, 2 or 3 heteroatoms independently selected from N, $NR^{14}$, $S(O)_q$ and O; and said heterocycloalkyl ring optionally contains, where possible, 1 or 2 double bonds, and is optionally substituted on carbon with 1 or 2 substituents independently selected from ($C_1$-$C_6$)alkyl, ($C_1$-$C_6$)alkoxy, OH, CN, $CF_3$, halo, $COOR^{14}$, $NR^{14}R^{15}$ and aryl.

In the above definitions $R^{14}$ and $R^{15}$ are independently selected from H and ($C_1$-$C_6$)alkyl.

When a structural formula is defined with a substituent attached to the core of the molecule by an unspecified, or "floating" bond, for example, as for the group $P^3$ in the case of formula (C), this definition encompasses the cases where the unspecified substituent is attached to any of the atoms on the ring in which the floating bond is located, whilst complying with the allowable valence for that atom.

In the case of compounds of the invention which may exist in tautomeric forms (i.e. in keto or enol forms), for example the compounds of formula (C) or (H), reference to a particular compound optionally includes all such tautomeric forms.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

As animal (and particularly bovine) materials are typically used in the culture of cells, they should be obtained from sources that are free from transmissible spongiform encaphalopathies (TSEs), and in particular free from bovine spongiform encephalopathy (BSE).

Where a compound is administered to the body as part of a composition then that compound may alternatively be replaced by a suitable prodrug.

Phosphorous-containing groups employed with the invention may exist in a number of protonated and deprotonated forms depending on the pH of the surrounding environment, for example the pH of the solvent in which they are dissolved. Therefore, although a particular form may be illustrated it is intended, unless otherwise mentioned, for these illustrations to merely be representative and not limiting to a specific protonated or deprotonated form. For example, in the case of a phosphate group, this has been illustrated as —OP(O)(OH)$_2$ but the definition includes the protonated forms —[OP(O)(OH$_2$)(OH)]$^+$ and —[OP(O)(OH$_2$)$_2$]$^{2+}$ that may exist in acidic conditions and the deprotonated forms —[OP(O)(OH)(O)]$^-$ and [OP(O)(O)$_2$]$^{2-}$ that may exist in basic conditions.

Compounds disclosed herein can exist as pharmaceutically acceptable salts. Thus, the compounds may be used in the form of their pharmaceutically acceptable salts i.e. physiologically or toxicologically tolerable salt (which includes, when appropriate, pharmaceutically acceptable base addition salts and pharmaceutically acceptable acid addition salts).

DESCRIPTION OF THE DRAWINGS

FIG. 1 shows the % of FHA-specific memory B cells for the indicated treatment groups.

MODES FOR CARRYING OUT THE INVENTION

Vaccine Preparation

References 31 and 85 disclose TLR7 agonists having formula (K) as discussed above. One of these compounds, 3-(5-amino-2-(2-methyl-4-(2-(2-(2-phosphonoethoxy)ethoxy)ethoxy)phenethyl)benzo[f]-[1,7]naphthyridin-8-yl)propanoic acid is referred to hereafter as compound "K2":

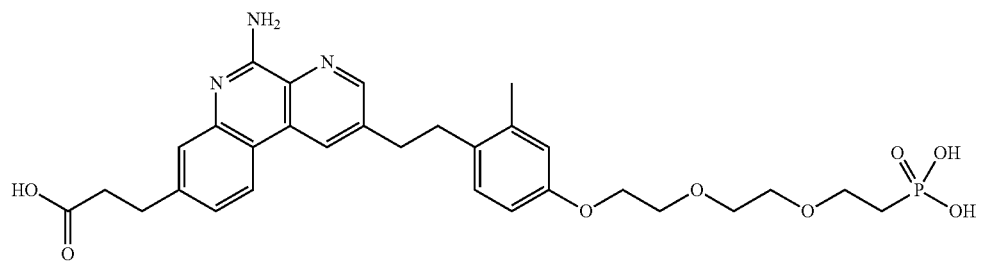

(K2)

Compound K2 is added to water at 4 mg/ml, then 1M NaOH is added to ensure full solubilisation, with stirring for 15 minutes at room temperature. This material is added to a suspension of aluminium hydroxide adjuvant (Al—H) to give the desired final concentration. This mixture is shaken for 2 hours at ambient temperature to ensure full adsorption, and then histidine buffer components are added (10 mM histidine buffer, pH 6.5).

The compound can also be used as an arginine salt monohydrate (obtained by mixing 98 mg of the compound with 1.7 ml of 0.1M arginine in 80/20 methanol/water to give a 57 mg/ml solution, followed by addition of 7 ml ethanol to precipitate the salt) in which case it is seen that the NaOH is not required for solubilisation prior to mixing with the Al—H.

Four different mixtures are prepared, giving a final K2 concentration of 10, 50, 250 or 500 µg/ml (to provide a 1, 5, 25 or 50 µg dose of K2 in a 100 µl dosage volume); the Al—H concentration is always 3 mg/ml. At all strengths >95% of compound K2 is adsorbed to the Al—H. The adsorbed adjuvant is referred to hereafter as "Al—H/K2".

Adjuvant Adsorption to Antigens 3-valent (DTaP) vaccines were adjuvanted with Al—H alone or with Al—H/K2. These formulations showed optimal pH (6.5-6.8±0.1) and osmolarity values (0.300±50 mO). Osmolarity was adjusted with NaCl. Adsorption was detected by separating the adjuvant-antigen complexes from unadsorbed antigens by centrifugation. 0.4% DOC was added to the supernatant containing the unadsorbed antigens. Antigens were precipitated by the addition of 60% TCA and collected by centrifugation. The pellet containing the TCA-precipitated antigens was resuspended in loading buffer and loaded onto an SDS-PAGE gel. The pellet containing the adjuvant-antigen complexes was resuspended in desorption buffer (4× concentration: 0.5 M $Na_2HPO_4$ pH, 8 g SDS, 25 g glycerol, 6.16 g DTT and bromophenol blue), the aluminium hydroxide was removed by centrifugation and the supernatant applied to an SDS-PAGE gel.

Using Al—H alone at a concentration of 2 mg/ml, the adsorption profiles for DT, TT, PT, FHA and 69K detected by Coomassie Blue staining were complete. No bands were detected in the DOC-TCA-treated supernatants. Western Blot analysis confirmed complete Al—H adsorption for DT, TT, PT, FHA and 69K.

Four different K2 concentrations were tested (0.1, 0.025, 0.01, 0.005 mg/ml). The Al—H concentration was constant at 2 mg/ml. Even at 0.1 mg/ml K2 all antigens were completely adsorbed.

Immunogenicity Testing with TLR Agonists

Four vaccines were tested, each containing (per 0.5 ml) 5 Lf tetanus toxoid, 2 Lf of diphtheria toxoid, and 16 µg acellular pertussis antigens (a mixture of purified PT-9K/129G, FHA and p69 pertactin).

The four vaccines were (A) unadjuvanted (B) adjuvanted with 2 mg/ml Al—H(C) adjuvanted with 2 mg/ml Al—H plus 100 µg/ml synthetic monophosphoryl lipid A i.e. a TLR4 agonist, or (D) adjuvanted with 2 mg/ml Al—H plus 1 mg/ml compound 'K2' i.e. a TLR7 agonist. The TLR agonists in vaccines (C) and (D) were adsorbed to the Al—H. All antigens were adsorbed to the Al—H in formulations (B), (C) and (D).

For comparison the BOOSTRIX™ product was also tested. As discussed above it contains (per 0.5 ml) 2.5 Lf of diphtheria toxoid, 5 Lf tetanus toxoid, and 18.5 µg acellular pertussis antigens (a mixture of purified PT, FHA and p69 pertactin), and it is adjuvanted with a mixture of aluminium phosphate and hydroxide salts. A mixture of buffer and Al—H was used as a negative control.

The four vaccines were administered to female Balb/C mice (6 weeks old) at 1001 intramuscular doses on days 0, 21 and 35. Sera were tested 2 weeks after each dose.

Serum total IgG titers were measured against each antigen and were as follows (geometric means):

| Day | Ag | Unadj | Al-H | Al-H + K2 | Al-H + MPL | Boostrix | -ve control |
|---|---|---|---|---|---|---|---|
| 14 | Dt | 0.030 | 0.603 | 8.119 | 1.762 | 1.205 | 0.030 |
|  | Tt | 0.191 | 2.546 | 46.14 | 14.49 | 3.217 | 0.030 |
|  | PT | 14.28 | 10.26 | 26.68 | 16.61 | 4.685 | 1.080 |
|  | FHA | 0.145 | 0.579 | 27.38 | 7.942 | 1.458 | 0.126 |
|  | p69 | 0.566 | 7.046 | 72.47 | 38.49 | 12.39 | 0.129 |
| 35 | Dt | 0.030 | 69.29 | 490.1 | 139.3 | 89.59 | 0.030 |
|  | Tt | 48.98 | 128.6 | 808.9 | 298.0 | 109.8 | 0.030 |
|  | PT | 245.0 | 267.5 | 377.1 | 695.9 | 195.0 | 2.734 |
|  | FHA | 7.847 | 65.25 | 400.6 | 231.0 | 49.49 | 0.030 |
|  | p69 | 32.50 | 222.2 | 1484 | 575.8 | 318.0 | 0.050 |
| 49 | Dt | 0.055 | 79.74 | 452.9 | 149.2 | 88.95 | 0.047 |
|  | Tt | 60.59 | 123.2 | 694.3 | 317.0 | 105.6 | 0.030 |
|  | PT | 200.8 | 387.7 | 329.7 | 642.3 | 300.0 | 2.065 |
|  | FHA | 20.96 | 72.10 | 462.4 | 272.5 | 78.98 | 0.030 |
|  | p69 | 107.6 | 384.9 | 1275 | 794.5 | 302.6 | 0.134 |

Thus in all cases and at all time points (except for PT at day 49) the highest titers in these 6 groups were seen in the mice which had received the antigens adjuvanted with adsorbed TLR agonist, and the addition of a TLR agonist to Al—H improved IgG responses relative to Al—H alone. Importantly, improved responses were seen in all cases when compared to the licensed BOOSTRIX™ vaccine. Moreover, unlike Al—H alone or BOOSTRIX™, the adsorbed TLR agonists were consistently able to improve anti-PT titers relative to the unadjuvanted group.

The use of the TLR agonists also leads to more rapid responses. The second dose showed a clear increase in IgG responses for all antigens, but the improvements after the third dose were not so significant. The mice in these experiments were naive to DTP but in a real-world human situation the target patients will previously have received DTP vaccine as a child and so the rapid response seen after the second dose in these experiments is helpful.

Immunogenicity Testing with Oil-in-Water Emulsion

Vaccines were prepared containing (per 0.5 ml) 5 Lf tetanus toxoid, 2 Lf of diphtheria toxoid, and 16 g acellular pertussis antigens (a mixture of purified PT-9K/129G, FHA and p69 pertactin). These were administered to female Balb/C mice (6 weeks old) at 100l intramuscular doses on days 0, 21 and 35. Sera were tested 2 weeks after each dose. Vaccines were (A) unadjuvanted or (B) adjuvanted with MF59 emulsion, by mixing 50 µl antigen solution with 50 µl MF59. For comparison the BOOSTRIX™ product was also tested, and an antigen-free negative control was also tested.

Serum total IgG titers were measured against each antigen and were as follows (geometric means):

| Day | Ag | Unadj | MF59 | Boostrix | −ve control |
|---|---|---|---|---|---|
| 14 | Dt | 0.030 | 0.038 | 1.308 | 0.030 |
|  | Tt | 0.064 | 3.025 | 2.480 | 0.030 |
|  | PT | 7.255 | 9.448 | 1.629 | 1.517 |
|  | FHA | 0.034 | 0.026 | 0.844 | 0.137 |
|  | p69 | 1.365 | 9.281 | 14.46 | 1.670 |
| 35 | Dt | 0.030 | 115.2 | 85.55 | 0.033 |
|  | Tt | 24.31 | 379.6 | 83.61 | 0.060 |
|  | PT | 247.4 | 391.9 | 112.7 | 3.582 |
|  | FHA | 7.433 | 148.8 | 37.58 | 0.068 |
|  | p69 | 11.44 | 1006 | 398.3 | 3.817 |
| 49 | Dt | 0.5165 | 78.54 | 92.18 | 0.054 |
|  | Tt | 40.21 | 337.5 | 99.09 | 0.030 |
|  | PT | 353.6 | 480.8 | 162.8 | 5.231 |
|  | FHA | 13.32 | 218.1 | 65.34 | 0.119 |
|  | p69 | 36.91 | 1036 | 403.6 | 1.952 |

Thus after two doses in DTP-naive mice the emulsion-adjuvanted vaccine gave much better antibody titers than the approved BOOSTRIX™ product. This superiority was maintained after a third dose, except for the anti-Dt response. Moreover, unlike BOOSTRIX™, the emulsion was able to improve anti-PT titers relative to the unadjuvanted group.

FHA-Specific Memory B Cells

Four-to-five months after the third dose, FHA-specific memory B cells were measured in the immunised mice. The mice were sacrificed and their spleen cells were cultured in the presence of IL-2 and CpG for 5 days in order to expand all memory B cells. Spleen cells were then harvested and seeded in 96-well ELISPOT plates previously coated with either FHA antigen (10 mg/ml) or anti-mouse Ig. After overnight incubation, plates were washed to remove unattached spleen cells and both FHA-specific and total memory B cells were detected by biotinylated anti-mouse Ig and HRP-streptavidin. Colored spots, representing individual memory B cell, were counted with an ELISPOT reader instrument. The percentage of FHA-specific B cells compared to total B cells was then calculated for each sample, and FIG. 1 shows the results for the following groups: (A) unadjuvanted; (B) adjuvanted with Al—H; (C) adjuvanted with Al—H plus MPL-A; (D) adjuvanted with Al—H plus 'K2'; (E) adjuvanted with MF59; (F) BOOSTRIX™; and (G) negative control. The highest response was seen in group (D) i.e. using the adsorbed TLR7 agonist. The next highest responses were seen in groups (C) and (E), with either the adsorbed TLR4 agonist or the emulsion, where responses were essentially the same but were still higher than with the BOOSTRIX™ product.

It will be understood that the invention has been described by way of example only and modifications may be made whilst remaining within the scope and spirit of the invention.

REFERENCES

[1] Broder et al. (2006) MMWR Recomm Rep 55(RR-3):1-34.
[2] Vaccine Design . . . (1995) eds. Powell & Newman. ISBN: 030644867X. Plenum.
[3] Vaccine Adjuvants: Preparation Methods and Research Protocols (Volume 42 of Methods in Molecular Medicine series). ISBN: 1-59259-083-7. Ed. O'Hagan.
[4] Clausi et al. (2008) J Pharm Sci DOI 10.1002/jps.21390.
[5] Rosenberg et al. (2010) J Immunol 184:136.20.
[6] U.S. Pat. No. 4,666,886.
[7] WO2009/118296.
[8] WO2008/005555.
[9] WO2009/111337.
[10] WO2009/067081.
[11] WO2007/040840.
[12] WO2010/014913.
[13] WO2012/031140.
[14] WO2011/119759.
[15] Steinhagen et al. (2011) Vaccine 29:3341-55.
[16] GB-A-2220211.
[17] Myers et al. (1990) pages 145-156 of Cellular and molecular aspects of endotoxin reactions.
[18] Ulrich (2000) Chapter 16 (pages 273-282) of reference 3.
[19] Johnson et al. (1999) J Med Chem 42:4640-9.
[20] Baldrick et al. (2002) Regulatory Toxicol Pharmacol 35:398-413.
[21] Coler et al. (2011) PLoS ONE 6(1):e16333.
[22] Johnson et al. (1999) Bioorg Med Chem Lett 9:2273-2278.
[23] Evans et al. (2003) Expert Rev Vaccines 2:219-229.
[24] Bazin et al. (2006) Tetrahedron Lett 47:2087-92.
[25] Wong et al. (2003) J Clin Pharmacol 43(7):735-42.
[26] US2005/0215517.
[27] WO03/011223.
[28] WO2007/053455.
[29] Garcon et al. (2007) Expert Rev Vaccines 6:723-39.
[30] WO 94/21292.
[31] WO2011/027222.
[32] WO2007/034917.
[33] WO2007/034173.
[34] WO2008/114817.
[35] US2009-0105212.
[36] US2009-0118263.
[37] US2009-0143400.
[38] US2009-0192153.
[39] WO2007/093901.
[40] WO2009/019553.
[41] US2009/0221631.
[42] WO2008/004948.
[43] WO2008/135791.
[44] US2009/0099216.
[45] US2009/0202484.
[46] WO2008/101867.
[47] WO2010/077613.
[48] US2010/0143301.
[49] WO2011/067669.
[50] WO2011/067672.
[51] WO2011/067673.
[52] WO2008/056263.
[53] WO2011/154442.
[54] WO2011/154443.
[55] WO2011/154444.

[56] WO90/14837.
[57] Podda & Del Giudice (2003) *Expert Rev Vaccines* 2:197-203.
[58] Podda (2001) *Vaccine* 19: 2673-2680.
[59] WO2008/043774.
[60] WO2005/097181.
[61] WO95/11700.
[62] US-2007/014805.
[63] WO2007/080308.
[64] WO2010/023551
[65] Brito et al. (2011) *Vaccine* 29:6262-6268.
[66] U.S. Pat. No. 8,092,813.
[67] WO2011/141819.
[68] U.S. Pat. No. 6,630,161.
[69] *Vaccines*. (eds. Plotkin & Orenstein). 4th edition, 2004, ISBN: 0-7216-9688-0.
[70] *National Institute for Biological Standards and Control*; Potters Bar, UK. www.nibsc.ac.uk
[71] Sesardic et al. (2001) *Biologicals* 29:107-22.
[72] NIBSC code: 98/560.
[73] Module 1 of WHO's *The immunological basis for immunization series* (Galazka).
[74] NIBSC code: 69/017.
[75] NIBSC code: DIFT.
[76] Sesardic et al. (2002) *Biologicals* 30:49-68.
[77] NIBSC code: 98/552.
[78] NIBSC code: TEFT.
[79] Rappuoli et al. (1991) *TIBTECH* 9:232-238.
[80] Nencioni et al. (1991) *Infect Immun.* 59(2): 625-30.
[81] Liao et al. (2012) *J Infect Dis.* 205:237-43.
[82] Verdijk et al. (2011) *Expert Rev Vaccines.* 10:635-44.
[83] Module 6 of WHO's *The immunological basis for immunization series* (Robertson)
[84] *Remington: The Science and Practice of Pharmacy* (Gennaro, 2000; 20th edition, ISBN: 0683306472)
[85] WO2011/049677.

The invention claimed is:

1. An immunogenic composition comprising a diphtheria toxoid, a tetanus toxoid, a pertussis toxoid, an aluminium salt adjuvant, and a toll-like receptor (TLR) agonist, wherein the TLR agonist includes at least one adsorptive moiety, at least 50% (by mass) of TLR agonist is adsorbed to the aluminium salt adjuvant, and the composition includes an excess (measured in Lf units) of tetanus toxoid relative to diphtheria toxoid.

2. The composition of claim 1, wherein the TLR agonist is a TLR4 agonist or a TLR7 agonist.

3. The composition of claim 1, wherein at least 99% of the TLR agonist is adsorbed to the aluminium salt adjuvant.

4. The composition of claim 1, with an $Al^{+++}$ concentration $\leq 0.5$ mg/ml.

5. The composition of claim 1, wherein the aluminium salt is an aluminium hydroxide.

6. The composition of claim 1, wherein the TLR agonist is a compound of formula 'K'

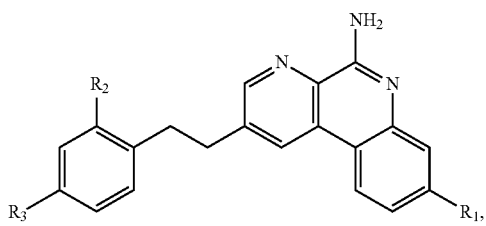

wherein: R1 is H, $C_1$-$C_6$alkyl, —$C(R^5)_2OH$, -$L^1R^5$, -$L^1R^6$, -$L^2R^5$, -$L^2R^6$, —$OL^2R^5$, or -$OL^2R^6$;
$L^1$ is —C(O)— or —O—;
$L^2$ is $C_1$-$C_6$alkylene, $C_2$-$C_6$alkenylene, arylene, heteroarylene or —$((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;
each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;
$L^4$ is arylene or heteroarylene;
$R^2$ is H or $C_1$-$C_6$alkyl;
$R^3$ is selected from $C_1$-$C_4$alkyl, -$L^3R^5$, -eR5, -L3R7, -L3L4L3R7, -L3L4R5, -L3L4eR5, OL3R5, —OL3R7, —OL3L4R7, —OL3L4eR7, —OR8, —OL3L4R5, —OL3L4eR5 and —C(R5) 20H;
each $R^4$ is independently selected from H and fluoro;
$R^5$ is —$P(O)(OR^9)_2$;
$R^6$ is —$CF_2P(O)(OR^9)_2$ or —$C(O)OR^{10}$;
$R^7$ is —$CF_2P(O)(OR^9)_2$ or —$C(O)OR^{10}$;
$R^8$ is H or $C_1$-$C_4$alkyl;
each $R^9$ is independently selected from H and $C_1$-$C_6$alkyl;
$R^{19}$ is H or $C^1$-$C^4$alkyl;
each p is independently selected from 1, 2, 3, 4, 5 and 6; and q is 1, 2, 3 or 4,
or a pharmaceutically acceptable salt thereof.

7. The composition of claim 1, wherein the TLR agonist is compound K2

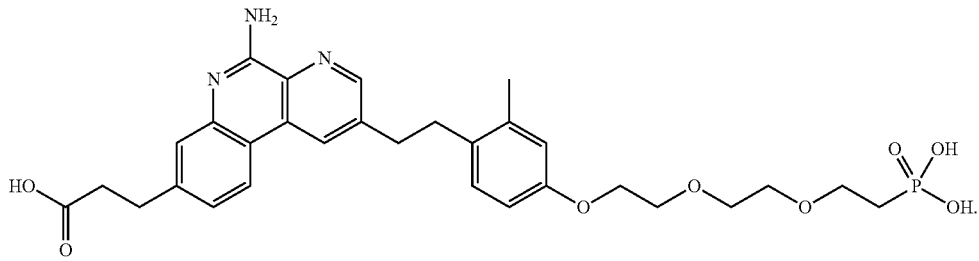

8. The composition of claim 1, wherein the at least one adsorptive moiety is a phosphate or a phosphonate.

9. The composition of claim 1, wherein the TLR agonist has a formula selected from the group consisting of:

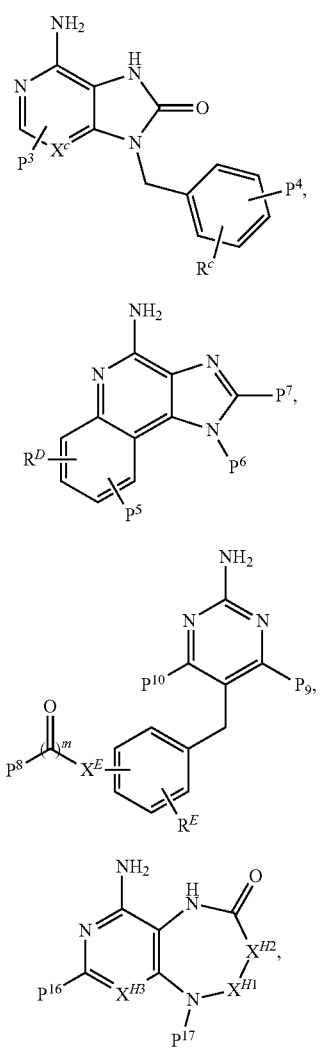

wherein:
(a) $P^3$ is selected from H, $C_1$-$C_6$alkyl, $CF_3$, and —$((CH_2)_pO)_q(CH_2)_pO_s$— and —Y-L-X—P(O) $(OR^X)(OR^Y)$; and $P^4$ is selected from H, $C_1$-$C_6$alkyl, —$C_1$-$C_6$alkylaryl and —Y-L-X—P(O) $(OR^X)(OR^Y)$; with the proviso that at least one of $P^3$ and $P^4$ is —Y-L-X—P(O) $(OR^X)(OR^Y)$;

(b) $P^5$ is selected from H, $C_1$-$C_6$alkyl, and —Y-L-X—P(O) $(OR^X)(OR^Y)$; $P^6$ is selected from H, $C_1$-$C_6$alkyl each optionally substituted with 1 to 3 substituents selected from $C_1$-$C_4$alkyl and OH, and —Y-L-X—P(O)$(OR^X)$ $(OR^Y)$; and $P^7$ is selected from H, $C_1$-$C_6$alkyl, —$((CH_2)_pO)_q(CH_2)_pO_s$—, —NH$C_1$-$C_6$alkyl and —Y-L-X—P(O)$(OR^X)(OR^Y)$; with the proviso that at least one of $P^5$, $P^6$ and $P^7$ is —Y-L-X—P(O)$(OR^X)(OR^Y)$;

(c) $P^8$ is selected from H, $C_1$-$C_6$alkyl, $C_1$-$C_6$alkoxy, —NH$C_1$-$C_6$alkyl each optionally substituted with OH, and —Y-L-X—P(O)$(OR^X)(OR^Y)$; and $P^9$ and $P^{10}$ are each independently selected from H, $C_1$-$C_6$alkyl, $C_1$-$C_6$alkoxy, —NH$C_1$-$C_6$alkyl each optionally substituted with OH and $C_1$-$C_6$alkyl, and —Y-L-X—P(O) $(OR^X)(OR^Y)$; with the proviso that at least one of $P^8$, $P^9$ or $P^{10}$ is —Y-L-X—P(O)$(OR^X)(OR^Y)$;

(d) $P^{16}$ and each $P^{18}$ are each independently selected from H, $C_1$-$C_6$alkyl, and —Y-L-X—P(O)$(OR^X)(OR^Y)$; $P^{17}$ is selected from H, $C_1$-$C_6$alkyl, aryl, heteroaryl, $C_1$-$C_6$alkylaryl, $C_1$-$C_6$alkyl heteroaryl, $C_1$-$C_6$alkylaryl-Y-L-X—P(O)$(OR^X)(OR^Y)$ and —Y-L-X—P(O) $(OR^X)(OR^Y)$, each optionally substituted with 1 to 2 substituents selected from $C_1$-$C_6$alkyl or heterocyclyl with the proviso that at least one of $P^{16}$, $P^{17}$ or a $P^{18}$ contains a —Y-L-X—P(O)$(OR^X)(OR^Y)$ moiety;

$R^X$ and $R^Y$ are independently selected from H and $C_1$-$C_6$alkyl;

$R^C$, $R^D$ and $R^H$ are each independently selected from H and $C_1$-$C_6$alkyl;

$X^C$ is selected from CH and N;

$R^E$ is selected from H, $C_1$-$C_6$alkyl, $C_1$-$C_6$alkoxy, C(O)$C_1$-$C_6$alkyl, halogen and —$((CH_2)_pO)_q(CH_2)_p$—;

$X^E$ is selected from a covalent bond, $CR^{E2}R^{E3}$ and $NR^{E4}$;

$R^{E2}$, $R^{E3}$ and $R^{E4}$ are independently selected from H and $C_1$-$C_6$alkyl;

$X^{H1}$-$X^{H2}$ is selected from —$CR^{H2}R^{H3}$—, —$CR^{H2}R^{H3}$—$CR^{H2}R^{H3}$—, —$C(O)CR^{H2}R^{H3}$—, —$C(O)CR^{H2}R^{H3}$—, —$CR^{H2}R^{H3}C(O)$—, —$NR^{H4}C(O)$—, $C(O)NR^{H4}$—, $CR^{H2}R^{H3}S(O)_2$ and —$CR^{H2}$=$CR^{H2}$—;

$R^{H2}$, $R^{H3}$ and $R^{H4}$ are each independently selected from H, $C_1$-$C_6$alkyl and $P^{18}$;

$X^{H3}$ is selected from N and CN;

X is selected from a covalent bond, O and NH;

Y is selected from a covalent bond, O, C(O), S and NH;

L is selected from, a covalent bond $C_1$-$C_6$alkylene, $C_1$-$C_6$alkenylene, arylene, heteroarylene, $C_1$-$C_6$alkyleneoxy and —$((CH_2)_pO)_q(CH_2)_p$— each optionally substituted with 1 to 4 substituents independently selected from halo, OH, $C_1$-$C_4$alkyl, —OP(O)$(OH)_2$ and —P(O)$(OH)_2$;

m is selected from 0 or 1;

each p is independently selected from 1, 2, 3, 4, 5 and 6;

q is selected from 1, 2, 3 and 4; and s is selected from 0 and 1,

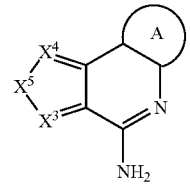

wherein:
$X^3$ is N;
$X^4$ is N or $CR^3$
$X^5$ is —$CR^4$=$CR^5$—;
$R^1$ and $R^2$ are H;
$R^3$ is H;
$R^4$ and $R^5$ are each independently selected from H, halogen, —C(O)$OR^7$, —C(O)$R^7$, —C(O)N($R^{11}R^{12}$), —N($R^{11}R^{12}$), —N($R^9$)2, —NHN($R^9$)2, —S$R^7$, —(CH2)n0$R^7$, —(CH2)n$R^7$, -L$R^8$, -L$R^{10}$, -OL$R^8$, -OL$R^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the C₁-C₆alkyl, C₁-C₆heteroalkyl, C₁-C₆haloalkyl, C₂-C₈alkene, C₂-C₈alkyne, C₁-C₆alkoxy, C₁-C₆haloalkoxy, aryl, heteroaryl, C₃-C₈cycloalkyl, and C₃-C₈heterocycloalkyl groups of $R^4$ and $R^5$ are each optionally substituted with 1 to 3 substituents independently selected from halogen, —CN, —NO₂, —$R^7$, —$OR^8$, —C(O)$R^8$, —OC(O)$R^8$, —C(O)$OR^8$, —N($R^9$)₂, —P(O)($OR^8$)₂, —OP(O)($OR^8$)₂, —P(O)($OR^{10}$)₂, —OP(O)($OR^{10}$)₂, —C(O)N($R^9$)₂, —S(O)₂$R^8$, —S(O)$R^8$, —S(O)₂N($R^9$)2, and —N$R^9$S(O)₂$R^8$;

or, $R^3$ and $R^4$, or $R^4$ and $R^{5'}$ or $R^5$ and $R^6$, when present on adjacent ring atoms, can optionally be linked together to form a 5-6 membered ring, wherein the 5-6 membered ring is optionally substituted with $R^7$;

each L is independently selected from a bond, —(O(CH₂)$_m$)$_t$—, C₁-C₆alkyl, C₂-C₆alkenylene and C₂-C₆alkynylene, wherein the C₁-C₆alkyl, C₂-C₆alkenylene and C₂-C₆alkynylene of L are each optionally substituted with 1 to 4 substituents independently selected from halogen, —$R^8$, —$OR^8$, —N($R^9$)₂, —P(O)($OR^8$)₂, —OP(O)($OR^8$)₂, —P(O)($OR^{10}$)₂, and —OP(O)($OR^{10}$)₂;

$R^7$ is selected from H, C₁-C₆alkyl, aryl, heteroaryl, C₃-C₈cycloalkyl, C₁-C₆heteroalkyl, C₁-C₆haloalkyl, C₂-C₈alkene, C₂-C₈alkyne, C₁-C₆alkoxy, C₁-C₆haloalkoxy, and C₃-C₈heterocycloalkyl, wherein the C₁-C₆alkyl, aryl, heteroaryl, C₃-C₈cycloalkyl, C₁-C₆heteroalkyl, C₁-C₆haloalkyl, C₂-C₈alkene, C₂-C₈alkyne, C₁-C₆alkoxy, C₁-C₆haloalkoxy, and C₃-C₈heterocycloalkyl groups of $R^7$ are each optionally substituted with 1 to 3 $R^{13}$ groups, and each $R^{13}$ is independently selected from halogen, —CN, -L$R^9$, -LO$R^9$, -OL$R^9$, -L$R^{10}$, -LO$R^{10}$, —OL$R^{10}$, -L$R^8$, -LO$R^8$, -OL$R^8$, -LS$R^8$, -LS$R^{10}$, -LC(O)$R^8$, -OLC(O)$R^8$, -LC(O)$R^8$, -LC(O)$R^{10}$, -LOC(O)$R^8$, -LC(O)N$R^9R^{11}$, -LC(O)N$R^9R^8$, -LN($R^9$)₂, -LN$R^9R^8$, -LN$R^9R^{10}$, -LC(O)N($R^9$)₂, -LS(O)₂$R^8$, -LS(O)$R^8$, -LC(O)N$R^8$OH, -LN$R^9$C(O)$R^8$, -LN$R^9$C(O)$OR^8$, -LS(O)₂N($R^9$)₂, —OLS(O)₂N($R^9$)₂, -LN$R^9$S(O)₂$R^8$, -LC(O)N$R^9$LN($R^9$)₂, -LP(O)($OR^8$)₂, -LOP(O)($OR^8$)₂, -LP(O)($OR^{10}$)₂ and -OLP(O)($OR^{10}$)₂;

each $R^8$ is independently selected from H, —CH($R^{10}$)2, C₁-C₈alkyl, C₂-C₈alkene, C₂-C₈alkyne, C₁-C₆haloalkyl, C₁-C₆alkoxy, C₁-C₆heteroalkyl, C₃-C₈cycloalkyl, C₂-C₈heterocycloalkyl, C₁-C₆hydroxyalkyl and C₁-C₆haloalkoxy, wherein the C₁-C₆alkyl, C₂-C₈alkene, C₂-C₈alkyne, C₁-C₆haloalkyl, C₁-C₆alkoxy, C₁-C₆heteroalkyl, C₃-C₈cycloalkyl, C₂-C₈heterocycloalkyl, C₁-C₆hydroxyalkyl and C₁-C₆haloalkoxy groups of $R^8$ are each optionally substituted with 1 to 3 substituents independently selected from —CN, $R^{11}$, —$OR^{11}$, —$SR^{11}$, —C(O)$R^{11}$, —OC(O)$R^{11}$, —C(O)N($R^9$)₂, —C(O)$OR^{11}$, —N$R^9$C(O)$R^{11}$, —N$R^9R^{10}$, —N$R^{11}R^{12}$, —N($R^9$)₂, —$OR^9$, —$OR^{10}$, —C(O)N$R^{11}R^{12}$, —C(O)N$R^{11}$OH, —S(O)₂$R^{11}$, —S(O)$R^{11}$, —S(O)₂N$R^{11}R^{12}$, —N$R^{11}$S(O)₂$R^{11}$, —P(O)($OR^{11}$)₂, and —OP(O)($OR^{11}$)₂;

each $R^9$ is independently selected from H, —C(O)$R^8$, —C(O)$OR^8$, —C(O)$R^{10}$, —C(O)$OR^{10}$, —S(O)₂$R^{10}$, —C₁-C₆ alkyl, C₁-C₆ heteroalkyl and C₃-C₆ cycloalkyl, or each $R^9$ is independently a C₁-C₆alkyl that together with N they are attached to form a C₃-C₈heterocycloalkyl, wherein the C₃-C₈heterocycloalkyl ring optionally contains an additional heteroatom selected from N, O and S, and wherein the C₁-C₆ alkyl, C₁-C₆ heteroalkyl, C₃-C₆ cycloalkyl, or C₃-C₈heterocycloalkyl groups of $R^9$ are each optionally substituted with 1 to 3 substituents independently selected from —CN, $R^{11}$, —$OR^{11}$, —$SR^{11}$, —C(O)$R^{11}$, OC(O)$R^{11}$, —C(O)$OR^{11}$, —N$R^{11}R^{12}$, —C(O)N$R^{11}R^{12}$, —C(O)N$R^{11}$OH, —S(O)₂$R^{11}$, —S(O)$R^{11}$, —S(O)₂N$R^{11}R^{12}$, —N$R^{11}$S(O)₂$R^{11}$, —P(O)($OR^{11}$)₂ and —OP(O)($OR^{11}$)₂;

each $R^{10}$ is independently selected from aryl, C₃-C₈cycloalkyl, C₃-C₈heterocycloalkyl and heteroaryl, wherein the aryl, C₃-C₈cycloalkyl, C₃-C₈heterocycloalkyl and heteroaryl groups are optionally substituted with 1 to 3 substituents selected from halogen, —$R^8$, —$OR^8$, -L$R^9$, -LO$R^9$, —N($R^9$)₂, —N$R^9$C(O)$R^8$, —N$R^9$CO₂$R^8$. —CO₂$R^8$, —C(O)$R^8$ and —C(O)N($R^9$)₂;

$R^{11}$ and $R^{12}$ are independently selected from H, C₁-C₆alkyl, C₁-C₆heteroalkyl, C₁-C₆haloalkyl, aryl, heteroaryl, C₃-C₈cycloalkyl, and C₃-C₈heterocycloalkyl, wherein the C₁-C₆alkyl, C₁-C₆heteroalkyl, C₁-C₆haloalkyl, aryl, heteroaryl, C₃-C₈cycloalkyl, and C₃-C₈heterocycloalkyl groups of $R^{11}$ and $R^{12}$ are each optionally substituted with 1 to 3 substituents independently selected from halogen, —CN, $R^8$, —$OR^8$, C(O)$R^8$, OC(O)$R^8$, —C(O)$OR^8$, —N($R^9$)₂, —N$R^8$C(O)$R^8$, —N$R^8$C(O)$OR^8$, —C(O)N($R^9$)₂, C³-C⁸heterocycloalkyl, —S(O)₂$R^8$, —S(O)₂N($R^9$)₂, —N$R^9$S(O)₂$R^8$, C₁-C₆haloalkyl and C₁-C₆haloalkoxy;

or $R^{11}$ and $R^{12}$ are each independently C₁-C₆alkyl and taken together with the N atom to which they are attached form an optionally substituted C₃-C₈heterocycloalkyl ring optionally containing an additional heteroatom selected from N, O and S;

ring A is an aryl or a heteroaryl, wherein the aryl and heteroaryl groups of Ring A are optionally substituted with 1 to 3 $R^A$ groups, wherein each $R^A$ is independently selected from —$R^8$, —$R^7$, —$OR^7$, —$OR^8$, —$R^{10}$, —$OR^{10}$, —$SR^8$, —NO₂, —CN, —N($R^9$)₂, —N$R^9$C(O)$R^8$, —N$R^9$C(S)$R^8$, —N$R^9$C(O)N($R^9$)₂, —N$R^9$C(S)N($R^9$)₂, —N$R^9$CO₂$R^8$, —N$R^9$N$R^9$C(O)$R^8$, —N$R^9$N$R^9$C(O)N($R^9$)₂, —N$R^9$N$R^9$CO₂$R^8$, —C(O)C(O)$R^8$, —C(O)CH₂C(O)$R^8$, —CO2$R^8$, —(CH2)$_n$CO₂$R^8$, —C(O)$R^8$, —C(S)$R^8$, —C(O)N($R^9$)₂, —C(S)N($R^9$)₂, —OC(O)N($R^9$)₂, —OC(O)$R^8$, —C(O)N(O$R^8$)$R^8$, —C(NO$R^8$)$R^8$, —S(O)₂$R^8$, S(O)₃$R^8$, —SO₂N($R^9$)₂, —S(O)$R^8$, —N$R^9$SO₂N($R^9$)₂, —N$R^9$SO₂$R^8$, —P(O)($OR^8$)₂, —OP(O)($OR^8$)₂, —P(O)($OR^{10}$)₂, —OP(O)($OR^{10}$)₂, —N(O$R^8$)$R^8$, —CH=CHCO₂$R^8$, —C(=NH)—N($R^9$)₂, and (CH₂)$_n$NHC(O)$R^8$ or two adjacent $R^A$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8,

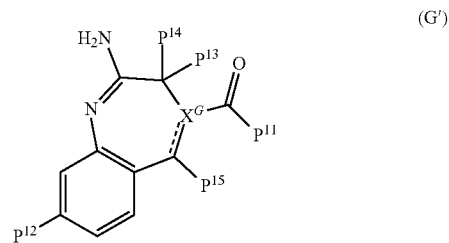

(G')

wherein:
P¹¹ is selected from H, C₁-C₆alkyl, C₁-C₆alkoxy, N$^V$R$^W$ and —Y-L-X—P(O) (OR$^X$)(OR$^Y$);
P¹² is selected from H, C₁-C₆alkyl, aryl optionally substituted by —C(O)NR$^V$R$^W$, and —Y-L-X—P(O)(OR$^X$) (OR$^Y$);
P¹³, P¹⁴ and P¹⁵ are independently selected from H, C₁-C₆alkyl, C₁-C₆alkoxy and —Y-L-X—P(O)(OR$^X$) (OR$^Y$); with the proviso that at least one of P¹¹, P¹², P¹³, P¹⁴ or P¹⁵ is —Y-L-X—P(O)(OR$^X$)(OR$^Y$);
R$^V$ and R$^W$ are independently selected from H, C₁-C₆alkyl or together with the nitrogen atom to which they are attached form a 4 to 7 remembered heterocyclic ring;
X$^G$ is selected from C, CH and N;
=== represents an optional double bond, wherein X$^G$ is C if === is a double bond; and R$^G$ is selected from H and C₁-C₆alkyl;
X is selected from a covalent bond, O and NH;
Y is selected from a covalent bond, O, C(O), S and NH;
L is selected from, a covalent bond C₁-C₆alkylene, C₁-C₆alkenylene, arylene, heteroarylene, C₁-C₆alkyleneoxy and —((CH₂)$_p$O)$_q$(CH₂)$_p$— each optionally substituted with 1 to 4 substituents independently selected from halo, OH, C₁-C₄alkyl, —OP(O)(OH)₂ and —P(O)(OH)₂;
each p is independently selected from 1, 2, 3, 4, 5 and 6 and q is selected from 1, 2, 3 and 4,

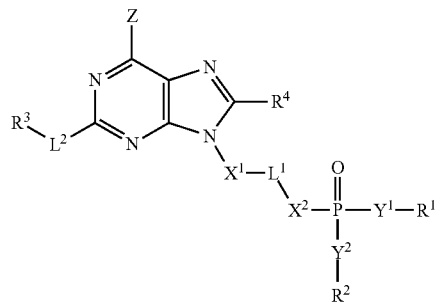

I

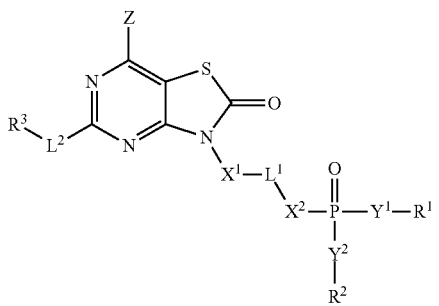

II wherein:
Z is —NH₂ or —OH;
X¹ is alkylene, substituted alkylene, alkenylene, substituted alkenylene, alkynylene, substituted alkynylene, carbocyclylene, substituted carbocyclylene, heterocyclylene, or substituted heterocyclylene;
L¹ is a covalent bond, arylene, substituted arylene, heterocyclylene, substituted heterocyclylene, carbocyclylene, substituted carbocyclylene, —S—, —S(O)—, S(O)₂, —NR⁵—, or —O—
X² is a covalent bond, alkylene, or substituted alkylene;

L² is NR⁵—, —N(R⁵)C(O)—, —O—, —S—, —S(O)—, S(O)₂, or a covalent bond;
R³ is H, alkyl, substituted alkyl, heteroalkyl, substituted heteroalkyl, alkenyl, substituted alkenyl, aryl, substituted aryl, arylalkyl, substituted arylalkyl, heterocyclyl, substituted heterocyclyl, heterocyclylalkyl, or substituted heterocyclylalkyl;
Y¹ and Y² are each independently a covalent bond, —O— or —NR⁵—; or —Y¹—R¹ and —Y²—R² are each independently —O—N=C(R⁶R⁷);
R¹ and R² are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—R⁵, -(substituted alkylene)-C(O)—O—R⁵, -alkylene-O—C(O)R⁵, -(substituted alkylene)-O—C(O)—R⁵, -alkylene-O—C(O)—O—R⁵, or -(substituted alkylene)-O—C(O)—O—R⁵
R⁴ is H, halogen, —OH, —O-alkyl, —O-alkylene-O—C(O)—O—R⁵, —O—C(O)—O—R⁵, —SH, or —NH(R⁵);
each R⁵, R⁶, and R⁷ are independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl; and

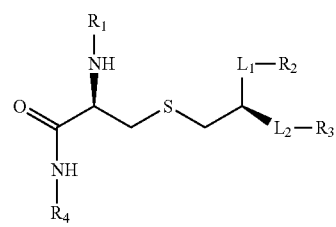

(J)

wherein:
R¹ is H, —C(O)—C₇-C₁₈alkyl or —C(O)—C₁-C₆alkyl;
R² is C₇-C₁₈alkyl;
R³ is C₇-C₁₈alkyl;
L₁ is —CH₂OC(O)—, —CH₂O—, —CH₂NR⁷C(O)— or —CH₂OC(O)NR⁷—;
L₂ is —OC(O)—, —O—, —NR⁷C(O)— or —OC(O)NR⁷—;
R⁴ is -L₃R⁵ or -L₄R⁵;
R⁵ is —N(R⁷)₂, —OR⁷, —P(O)(OR⁷)₂, —C(O)OR⁷, —NR⁷C(O)L₃R⁸, —NR⁷C(O)L₄R⁸, —OL₃R⁶, —C(O)NR⁷L₃R⁸, —C(O)NR⁷L₄R⁸, —S(O)₂OR⁷, —OS(O)₂OR⁷, C₁-C₆alkyl, a C₆aryl, a C₁₀aryl, a C₁₄aryl, 5 to 14 ring membered heteroaryl containing 1 to 3 heteroatoms selected from O, S and N, C₃-C₈cycloalkyl or a 5 to 6 ring membered heterocycloalkyl containing 1 to 3 heteroatoms selected from O, S and N, wherein the aryl, heteroaryl, cycloalkyl and heterocycloalkyl of R⁵ are each unsubstituted or the aryl, heteroaryl, cycloalkyl and heterocycloalkyl of R⁵ are each substituted with 1 to 3 substituents independently selected from —OR⁹, —OL₃R⁶, —OL₄R⁶, —OR⁷, and —C(O)OR⁷;
L₃ is a C₁-C₁₀alkylene, wherein the C₁-C₁₀alkylene of L₃ is unsubstituted, or the C₁-C₁₀alkylene of L₃ is substituted with 1 to 4 R⁶ groups, or the C₁-C₁₀alkylene of L₃ is substituted with 2 C$_1$-C$_6$alkyl groups on the same carbon atom which together, along with the carbon atom they are attached to, form a C$_3$-C$_8$cycloakyl;

L$_4$ is —((CR$^7$R$^7$)$_p$O)$_q$(CR$^{10}$R$^{10}$)$_p$— or —(CR$^{11}$R$^{11}$)((CR$^7$R$^7$)$_p$O)$_q$(CR$^{10}$R$^{10}$)$_p$—, wherein each R$^{11}$ is a C$_1$-C$_6$alkyl groups which together, along with the carbon atom they are attached to, form a C$_3$-C$_8$cycloakyl;

each R$^6$ is independently selected from halo, C$_1$-C$_6$alkyl, C$_1$-C$_6$alkyl substituted with 1-2 hydroxyl groups, —OR$^7$, —N(R$^7$)$_2$, —C(O)OH, —C(O)N(R$^7$)$_2$, —P(O)(OR$^7$)$_2$, a C$_6$aryl, a C$_{10}$aryl and a C$_{14}$aryl;

each R$^7$ is independently selected from H and C$_1$-C$_6$alkyl;

R$^8$ is selected from —SR$^7$, —C(O)OH, —P(O)(OR$^7$)$_2$, and a 5 to 6 ring membered heterocycloalkyl containing 1 to 3 heteroatoms selected from O and N;

R$^9$ is phenyl;

each R$^{19}$ is independently selected from H and halo;

each p is independently selected from 1, 2, 3, 4, 5 and 6, and q is 1, 2, 3 or 4, or is a 3d-monophosphoryl lipid A (MPL).

10. The composition of claim 1, wherein the TLR agonist is one of

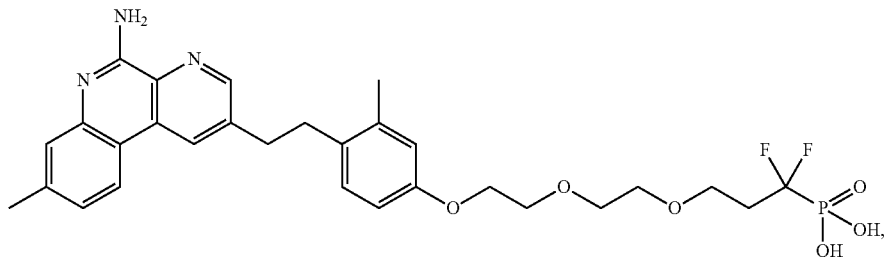

Compound 1 (3-(2-(2-(4-(2-(5-amino-8-methylbenzo[f][1,7]naphthyridin-2-yl)ethyl)-3-methylphenoxy)ethoxy)ethoxy)-1,1-difluoropropyl)phosphonic acid

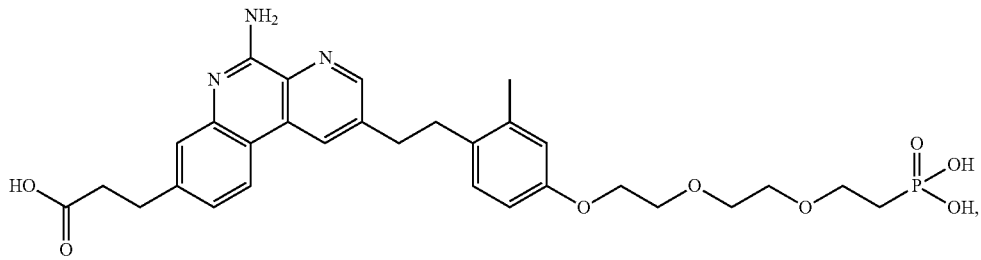

Compound 2 3-(5-amino-2-(2-methyl-4-(2-(2-(2-phosphonoethoxy)ethoxy)ethoxy)phenethyl)benzo[f][1,7]naphthyridin-8-yl)propanoic acid

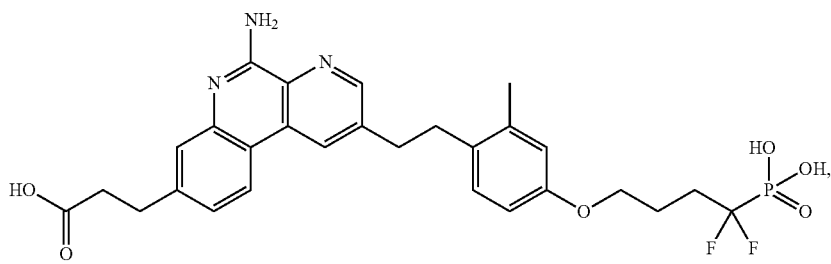

Compound 3 3-(5-amino-2-(4-(4,4-difluoro-4-phosphonobutoxy)-2-methylphenethyl)benzo[f][1,7]naphthyridin-8-yl)propanoic acid

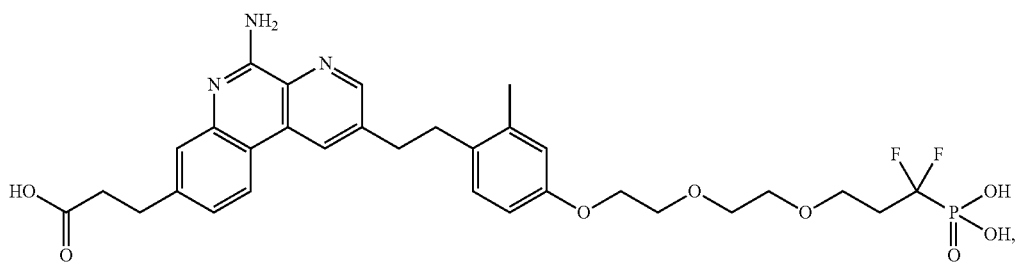

Compound 4 3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid

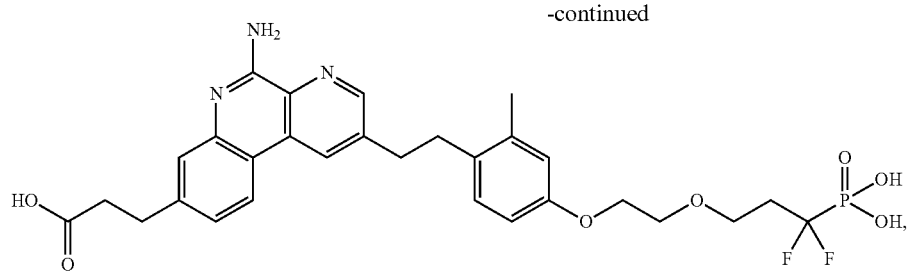

Compound 5 3-(5-amino-2-(4-(2-(3,3-difluoro-3-phosphonopropoxy)ethoxy)-2-methylphenethyl)benzo[f][1,7]naphthyridin-8-yl)propanoic acid

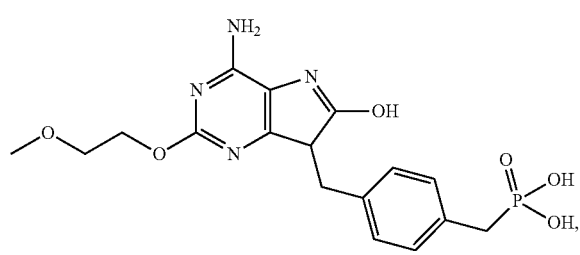

Compound 6 (4-((6-amino-8-hydroxy-2-(2-methoxyethoxy)-9H-purin-9-yl)methyl)benzyl)phosphonic acid

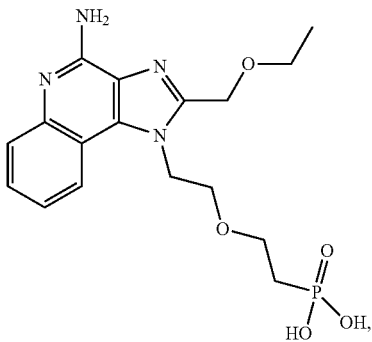

Compound 7 (2-(2-(4-amino-2-(ethoxymethyl)-1H-imidazo[4,5-c]quinolin-1-yl)ethoxy)ethyl) phosphonic acid

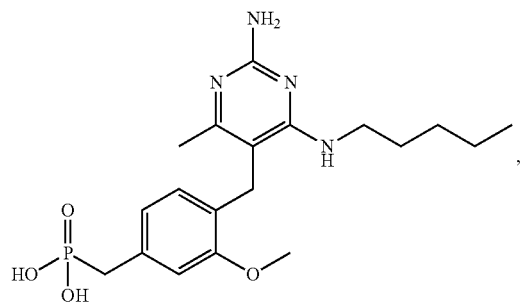

Compound 8 (4-((2-amino-4-methyl-6-(pentylamino)pyrimidin-5-yl)methyl)-3-methoxybenzyl)phosphonic acid

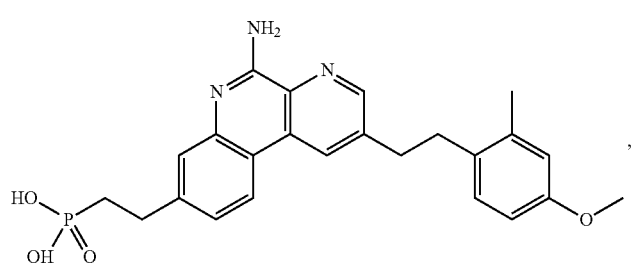

Compound 9 (2-(5-amino-2-(4-methoxy-2-methylphenethyl)benzo[f][1,7]naphthyridin-8-yl)ethyl)phosphonic acid

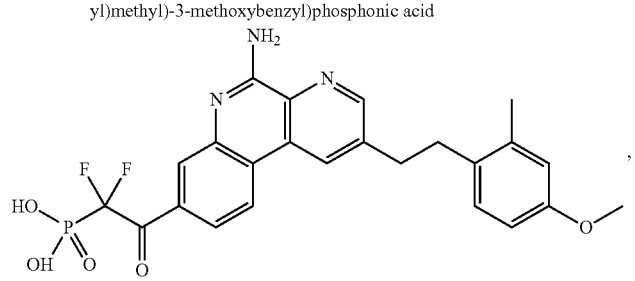

Compound 10 (2-(5-amino-2-(4-methoxy-2-methylphenethyl)benzo[f][1,7]naphthyridin-8-yl)-1,1-difluoro-2-oxoethyl)phosphonic acid

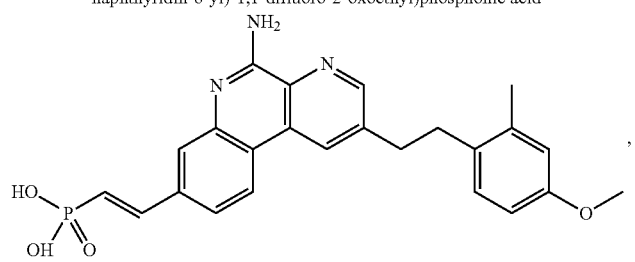

Compound 11 (E)-(2-(5-amino-2-(4-methoxy-2-methylphenethyl)benzo[f][1,7]naphthyridin-8-yl)vinyl)phosphonic acid

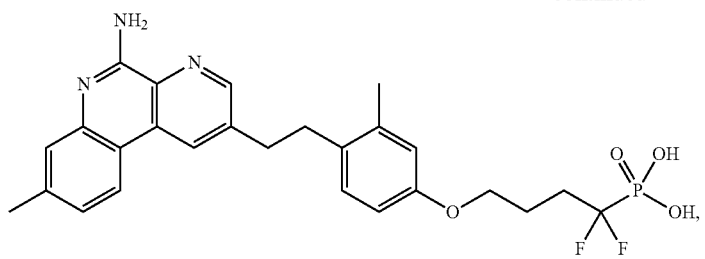

Compound 12 (4-(4-(2-(5-amino-8-methylbenzo[f][1,7]naphthyridin-2-yl)ethyl)-3-methylphenoxy)-1,1-difluorobutyl)phosphonic acid

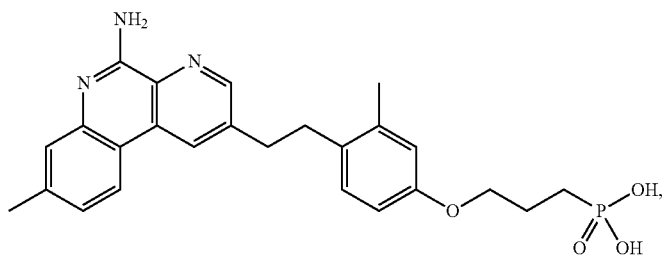

Compound 13 (3-(4-(2-(5-amino-8-methylbenzo[f][1,7]naphthyridin-2-yl)ethyl)-3-methylphenoxy)propyl)phosphonic acid

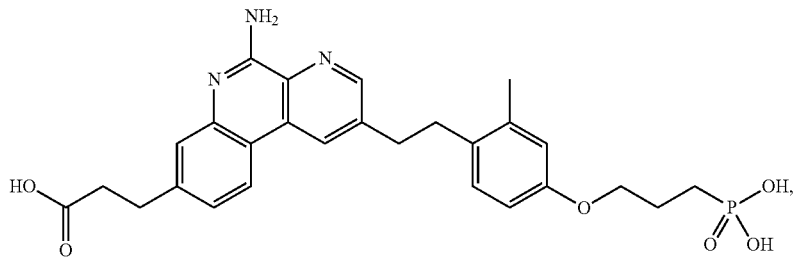

Compound 14 3-(5-amino-2-(2-methyl-4-(3-phosphonopropoxy)phenethyl)benzo[f][1,7]naphthyridin-8-yl)propanoic acid

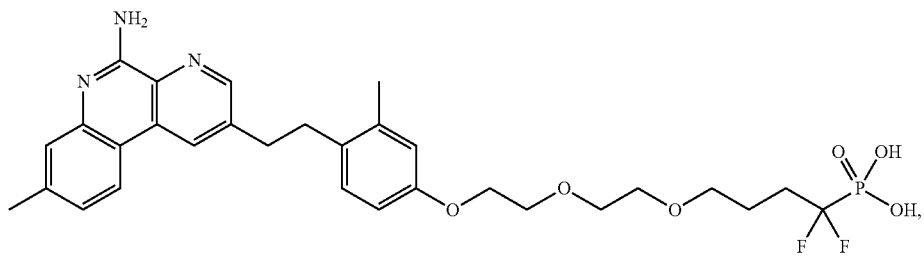

Compound 15 (4-(2-(2-(4-(2-(5-amino-8-methylbenzo[f][1,7]naphthyridin-2-yl)ethyl)-3-methylphenoxy)ethoxy)ethoxy)-1,1-difluorobutyl)phosphonic acid

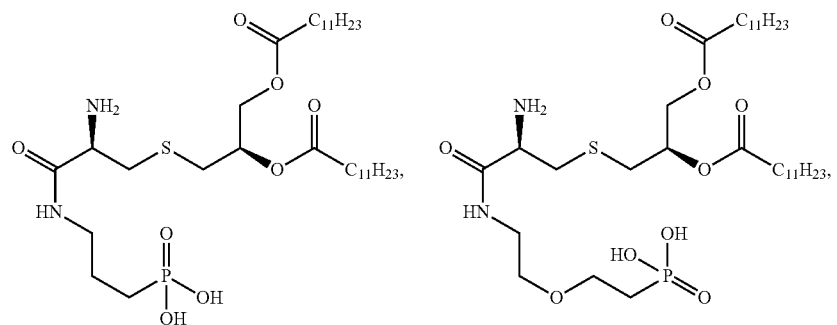

Compound 16 (3-((R)-2-amino-3-(((R)-2,3-bis(dodecanoyloxy)propyl)thio)propanamido)propyl)phosphonic acid Compound 17 ((8R,12R)-8-amino-12-(dodecanoyloxy)-7,15-dioxo-3,14-dioxa-10-thia-6-azahexacosyl)phosphonic acid

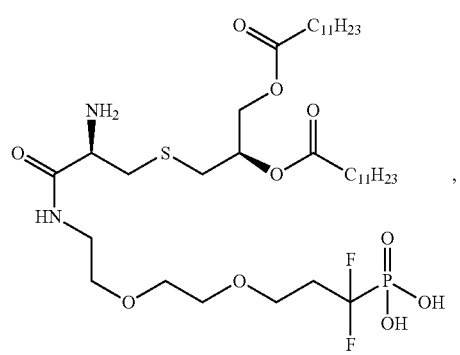

Compound 18 ((12R,16R)-12-amino-16-(dodecanoyloxy)-1,1-difluoro-11,19-dioxo-4,7,18-trioxa-14-thia-10-azatriacontyl)phosphonic acid

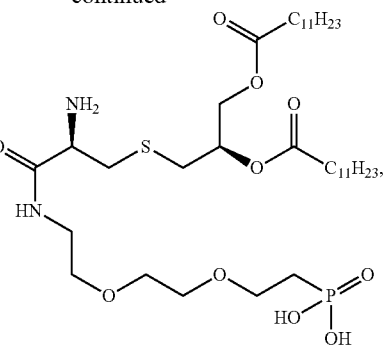

Compound 19 ((11R,15R)-11-amino-15-(dodecanoyloxy)-10,18-dioxo-3,6,17-trioxa-13-thia-9-azanonacosyl)phosphonic acid

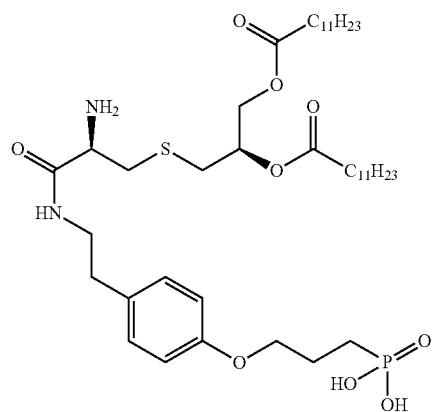

Compound 20 (3-(4-(2-((R)-2-amino-3-(((R)-2,3-bis(dodecanoyloxy)propyl)thio)propanamido)ethyl)phenoxy)propyl)phosphonic acid

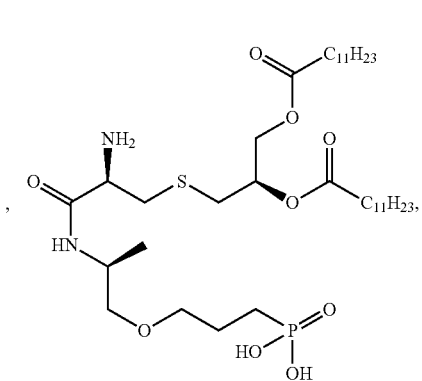

Compound 21 ((6S,9R,13R)-9-amino-13-(dodecanoyloxy)-6-methyl-8,16-dioxo-4,15-dioxa-11-thia-7-azaheptacosyl)phosphonic acid

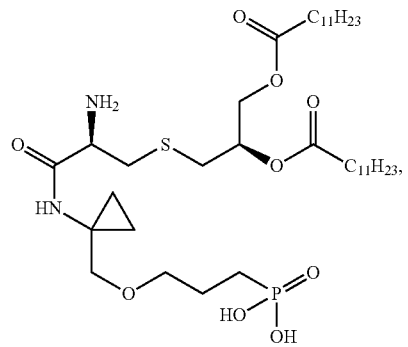

Compound 22 (3-((1-((R)-2-amino-3-(((R)-2,3-bis(dodecanoyloxy)propyl)thio)propanamido)cyclopropyl)methoxy)propyl)phosphonic acid

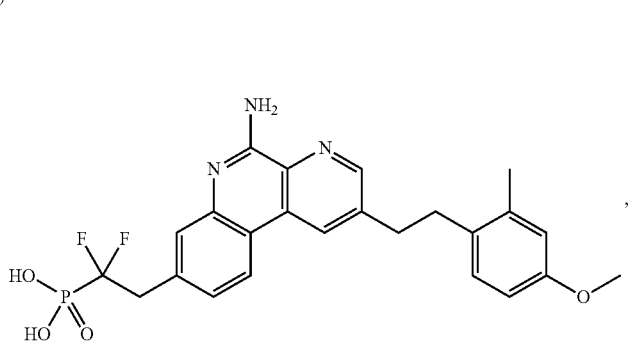

Compound 23 (2-(5-amino-2-(4-methoxy-2-methylphenethyl)benzo[f][1,7]naphthyridin-8-yl)-1,1-difluoroethyl)phosphonic acid

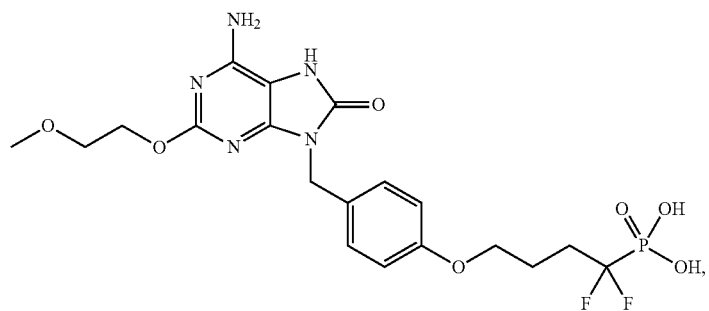

Compound 24 (4-(4-((6-amino-2-(2-methoxyethoxy)-8-oxo-7H-purin-9(8H)-yl)methyl)phenoxy)-1,1-difluorobutyl)phosphonic acid

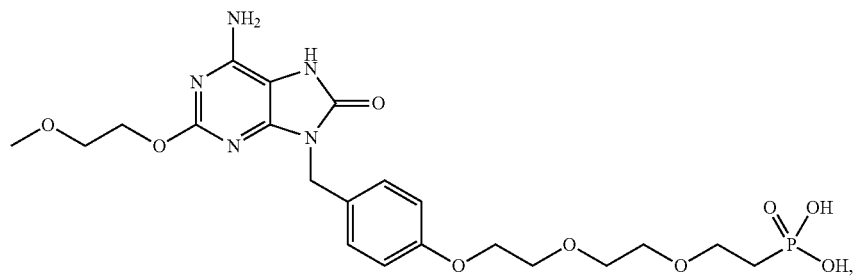

Compound 25 (2-(2-(2-(4-((6-amino-2-(2-methoxyethoxy)-8-oxo-7H-purin-9(8H)-yl)methyl)phenoxy)ethoxy)ethoxy)ethyl)phosphonic acid

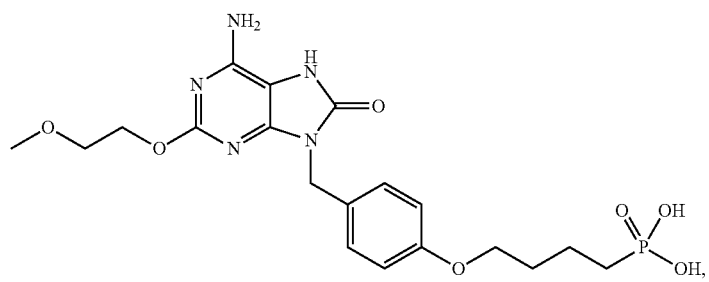

Compound 26 (4-(4-((4-amino-6-(2-methoxyethoxy)-2-oxo-2,3-dihydro-1H-imidazo[4,5-c]pyridin-1-yl)methyl)phenoxy)butyl)phosphonic acid

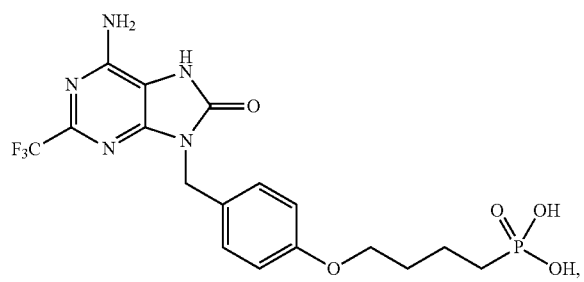

Compound 27 (4-(4-((4-amino-2-oxo-6-(trifluoromethyl)-2,3-dihydro-1H-imidazo[4,5-c]pyridin-1-yl)methyl)phenoxy)butyl)phosphonic acid

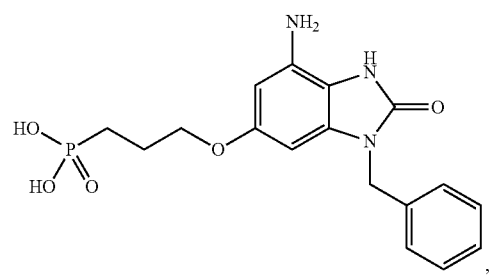

Compound 28 (3-((6-amino-9-benzyl-8-oxo-8,9-dihydro-7H-purin-2-yl)oxy)propyl)phosphonic acid

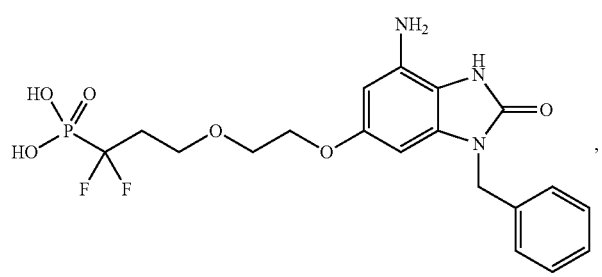

Compound 29 (3-(2-((6-amino-9-benzyl-8-oxo-8,9-dihydro-7H-purin-2-yl)oxy)ethoxy)-1,1-difluoropropyl)phosphonic acid

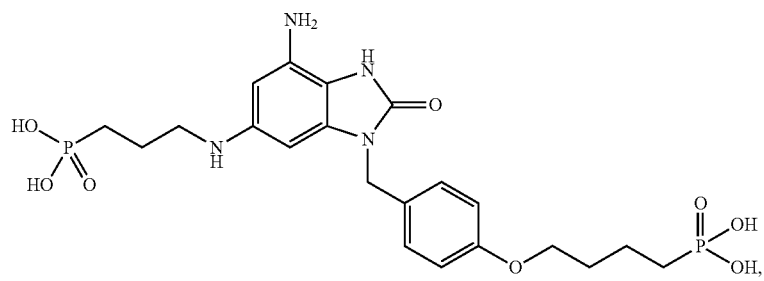

Compound 30 (3-((4-amino-1-(4-(butyloxyphosphonate)benzyl)-2-oxo-2,3-dihydro-1H-imidazo[4,5-c]pyridin-6-yl)amino)propyl)phosphonic acid

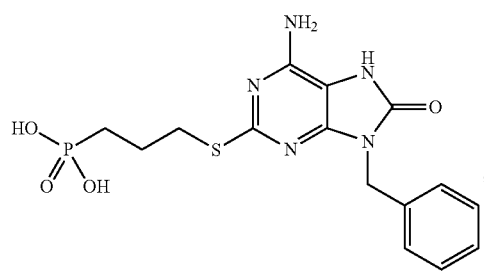

Compound 31 (3-((4-amino-1-benzyl-2-oxo-2,3-dihydro-1H-imidazo[4,5-c]pyridin-6-yl)thio)propyl) phosphonic acid

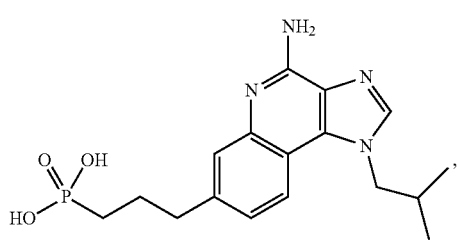

Compound 32 (3-(4-amino-1-isobutyl-1H-imidazo[4,5-c]quinolin-7-yl)propyl)phosphonic acid

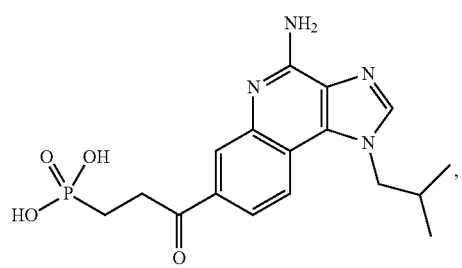

Compound 33 (3-(4-amino-1-isobutyl-1H-imidazo[4,5-c]quinolin-7-yl-3-oxopropyl)phosphonic acid

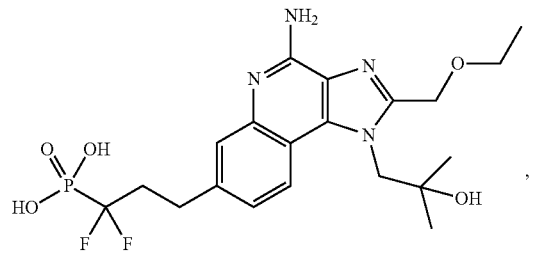

Compound 34 (3-(4-amino-2-(ethoxymethyl)-1-(2-hydroxy-2-methylpropyl)-1H-imidazo[4,5-c]quinolin-7-yl)-1,1-difluoropropyl) phosphonic acid

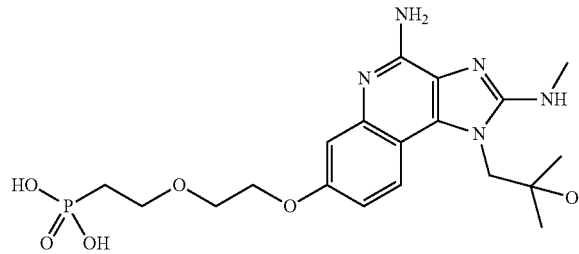

Compound 35 (2-(2-((4-amino-1-(2-hydroxy-2-methylpropyl)-2-(methylamino)-1H-imidazo[4,5-c]quinolin-7-yl)oxy)ethoxy)ethyl) phosphonic acid

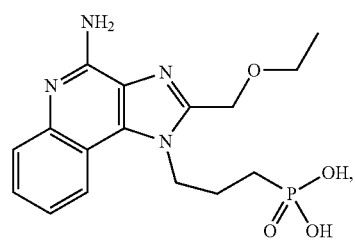

Compound 36 (3-(4-amino-2-(ethoxymethyl)-1H-imidazo[4,5-c]quinolin-1-yl)propyl) phosphonic acid

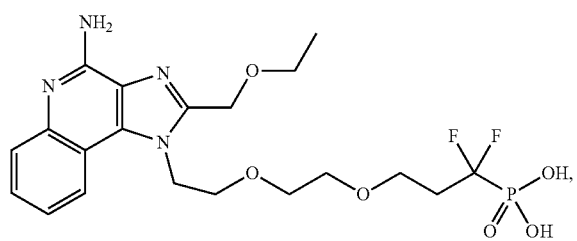

Compound 37 (3-(2-(2-(4-amino-2-(ethoxymethyl)-1H-imidazo[4,5-c]quinolin-1-yl)ethoxy)ethoxy)-1,1-difluoropropyl)phosphonic acid

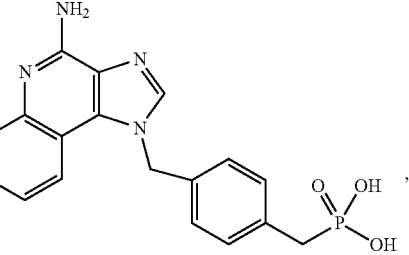

Compound 38 (4-((4-amino-1H-imidazo[4,5-c]quinolin-1-yl)methyl)benzyl)phosphonic acid

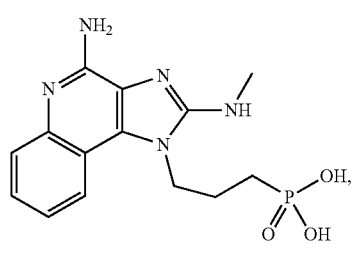

Compound 39 (3-(4-amino-2-(methylamino)-1H-imidazo[4,5-c]quinolin-1-yl)propyl) phosphonic acid

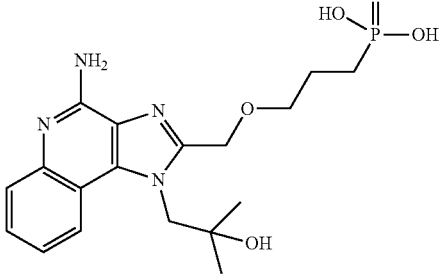

Compound 40 (3-((4-amino-1-(2-hydroxy-2-methylpropyl)-1H-imidazo[4,5-c]quinolin-2-yl)methoxy)propyl)phosphonic acid -continued

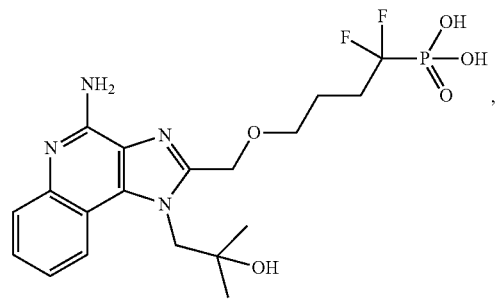

Compound 41 (4-((4-amino-1-(2-hydroxy-2-methylpropyl)-1H-imidazo[4,5-c]quinolin-2-yl)methoxy)-1,1-difluorobutyl) phosphonic acid

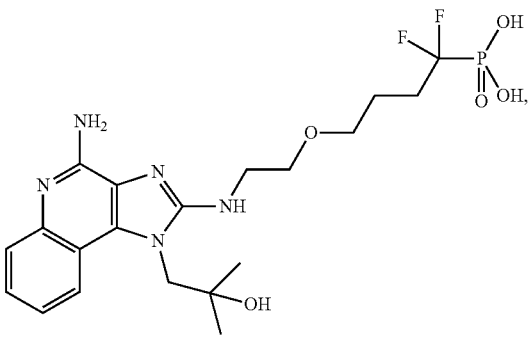

Compound 42 (4-(2-((4-amino-1-(2-hydroxy-2-methylpropyl)-1H-imidazo[4,5-c]quinolin-2-yl)amino)ethoxy)-1,1-difluorobutyl)phosphonic acid

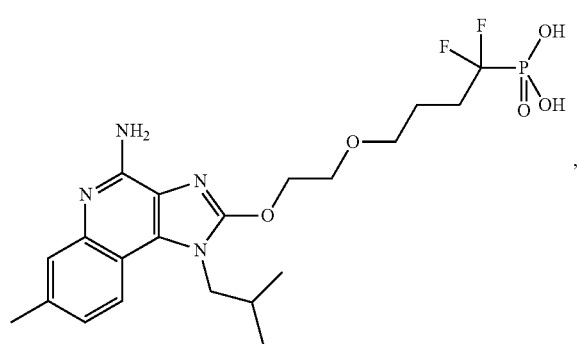

Compound 43 (4-(2-((4-amino-1-isobutyl-7-methyl-1H-imidazo[4,5-c]quinolin-2-yl)oxy)ethoxy)-1,1-difluorobutyl)phosphonic acid

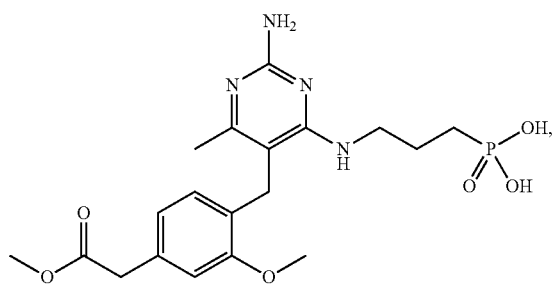

Compound 44 (3-((2-amino-5-(2-methoxy-4-(2-methoxy-2-oxoethyl)benzyl)-6-methylpyrimidin-4-yl)amino)propyl)phosphonic acid

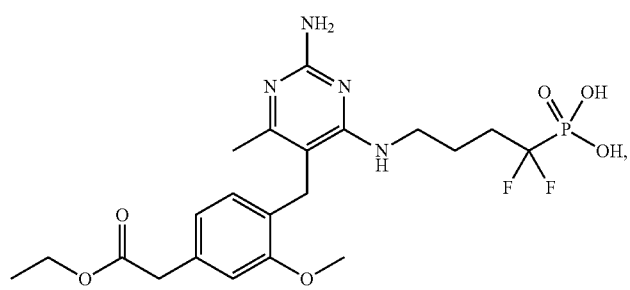

Compound 45 (4-((2-amino-5-(4-(2-ethoxy-2-oxoethyl)-2-methoxybenzyl)-6-methylpyrimidin-4-yl)amino)-1,1-difluorobutyl)phosphonic acid

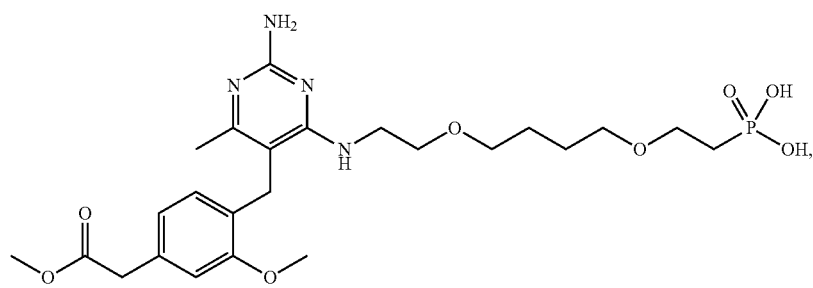

Compound 46 (2-(2-(2-((2-amino-5-(2-methoxy-4-(2-methoxy-2-oxoethyl)benzyl)-6-methylpyrimidin-4-yl)amino)ethoxy)ethoxy)ethyl)phosphonic acid

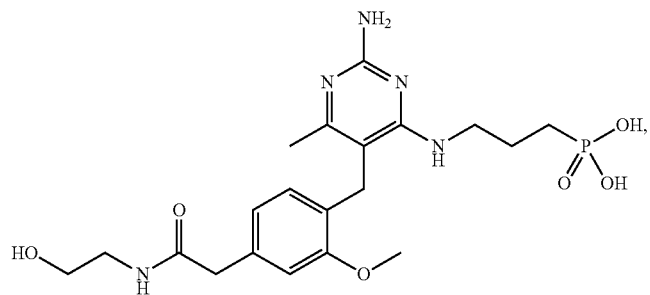

Compound 47 (3-((2-amino-5-(4-(2-((2-hydroxyethyl)amino)-2-oxoethyl)-2-methoxybenzyl)-6-methylpyrimidin-4-yl)amino)propyl)phosphonic acid

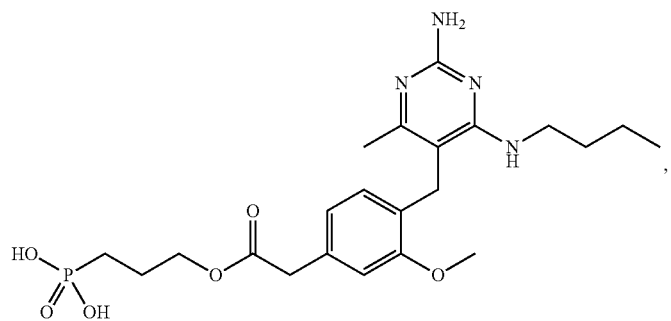

Compound 48 (3-(2-(4-((2-amino-4-(butylamino)-6-methylpyrimidin-5-yl)methyl)-3-methoxyphenyl)acetoxy)propyl)phosphonic acid

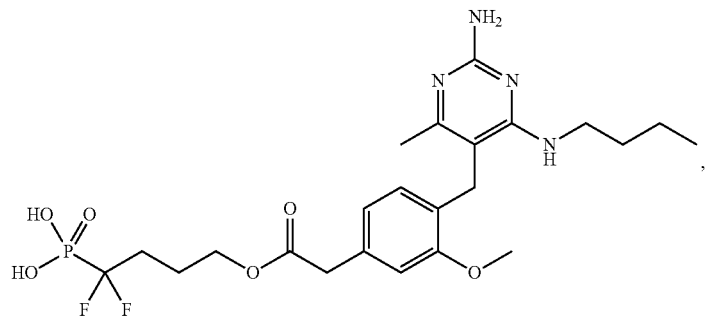

Compound 49 (4-(2-(4-((2-amino-4-(butylamino)-6-methylpyrimidin-5-yl)methyl)-3-methoxyphenyl)acetoxy)-1,1-difluorobutyl)phosphonic acid

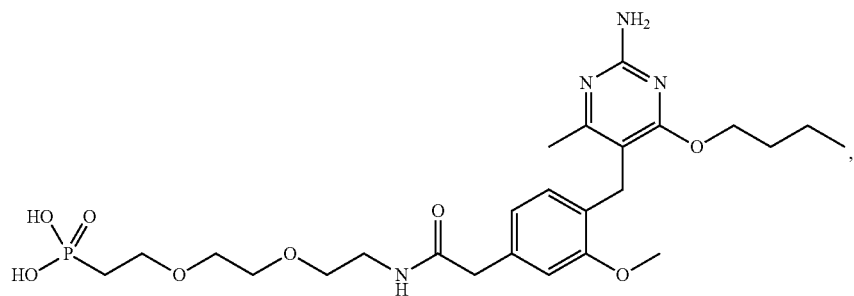

Compound 50 (2-(2-(2-(2-(4-((2-amino-4-butoxy-6-methylpyrimidin-5-yl)methyl)-3-methoxyphenyl)acetamido)ethoxy)ethoxy)ethyl)phosphonic acid

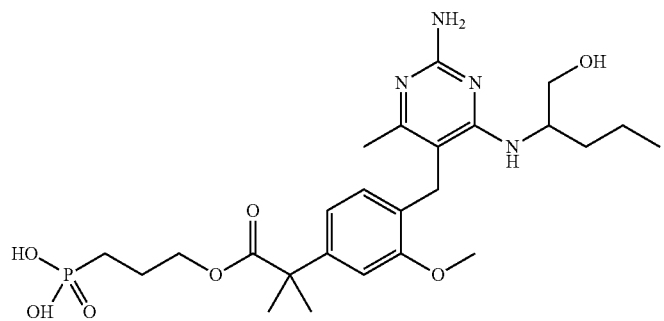

Compound 51 (3-((2-(4-((2-amino-4-((1-hydroxypentan-2-yl)amino)-6-methylpyrimidin-5-yl)methyl)-3-methoxyphenyl)-2-methylpropanoyl)oxy)propyl)phosphonic acid

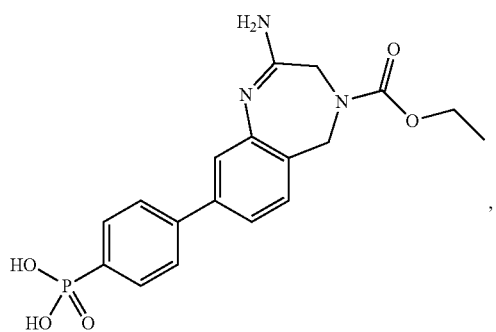

Compound 52 (4-(2-amino-4-(ethoxycarbonyl)-4,5-dihydro-3H-benzo[e][1,4]diazepin-8-yl)phenyl)phosphonic acid

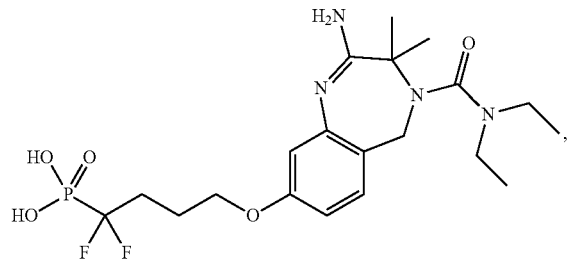

Compound 53 (4-((2-amino-4-(diethylcarbamoyl)-3,3-dimethyl-4,5-dihydro-3H-benzo[e][1,4]diazepin-8-yl)oxy)-1,1-difluorobutyl)phosphonic acid

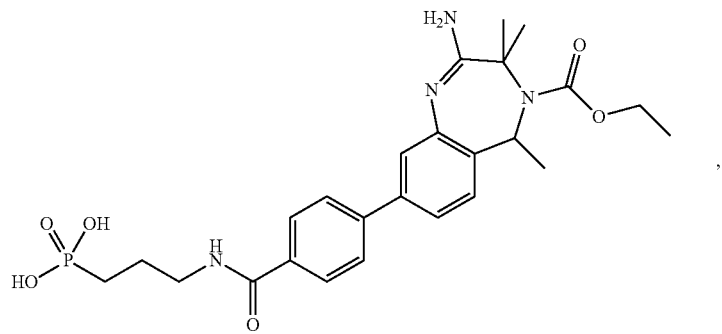

Compound 54 (3-(4-(2-amino-4-(ethoxycarbonyl)-5-methyl-4,5-dihydro-3H-benzo[e][1,4]diazepin-8-yl)benzamido)propyl)phosphonic acid

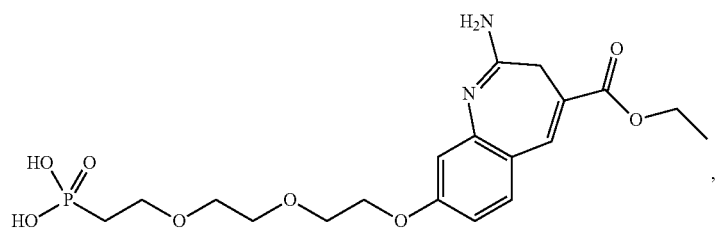

Compound 55 (2-(2-(2-((2-amino-4-(ethoxycarbonyl)-3H-benzo[b]azepin-8-yl)oxy)ethoxy)ethoxy)ethyl)phosphonic acid

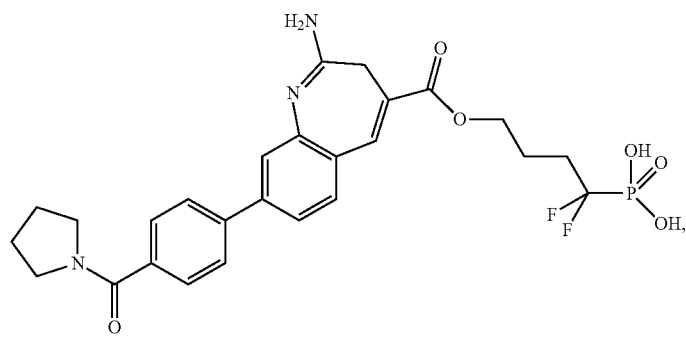

Compound 56 (4-((2-amino-8-(4-(pyrrolidine-1-carbonyl)phenyl)-3H-benzo[b]azepine-4-carbonyl)oxy)-1,1-difluorobutyl)phosphonic acid

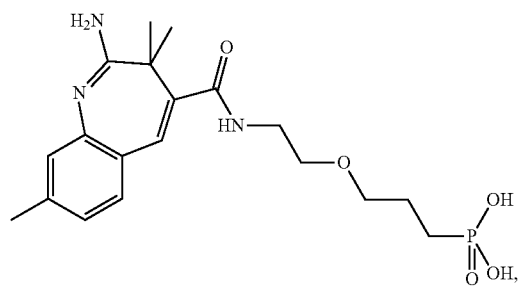

Compound 57 (3-(2-(2-amino-3,3,8-trimethyl-4,5-dihydro-3H-benzo[e][1,4]diazepine-4-carboxamido)ethoxy)propyl)phosphonic acid

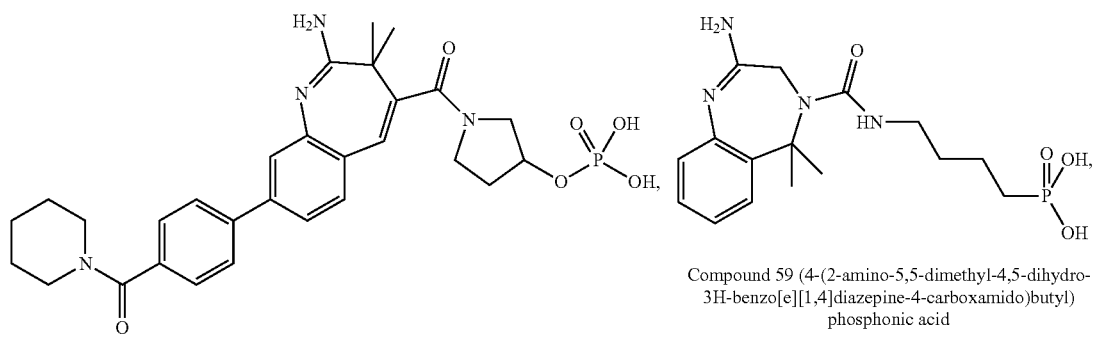

Compound 58 1-(2-amino-3,3-dimethyl-8-(4-(piperidine-1-carbonyl)phenyl)3H-benzo[b]azepine-4-carbonyl)pyrrolidin-3-yl dihydrogen phosphate Compound 59 (4-(2-amino-5,5-dimethyl-4,5-dihydro-3H-benzo[e][1,4]diazepine-4-carboxamido)butyl)phosphonic acid

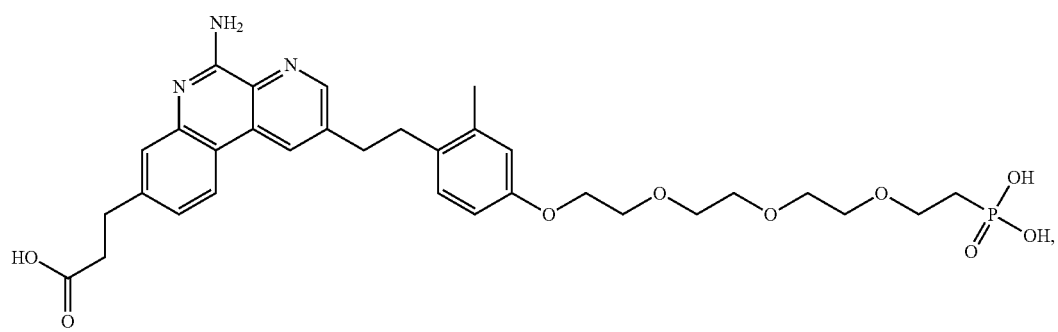

Compound 60 3-(5-amino-2-(2-methyl-4-(2-(2-(2-(2-phosphonoethoxy)ethoxy)ethoxy)ethoxy)phenethyl)benzo[f][1,7]naphthyridin-8-yl)propanoic acid

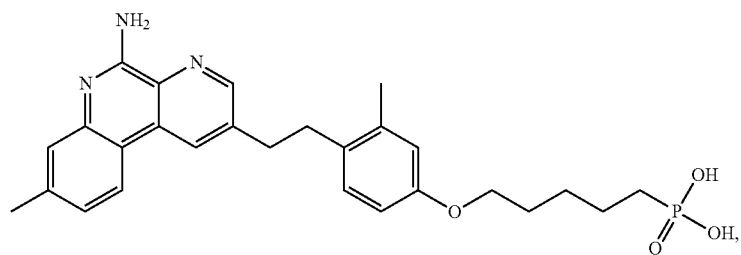

Compound 61 (5-(4-(2-(5-amino-8-methylbenzo[f][1,7]naphthyridin-2-yl)ethyl)-3-methylphenoxy)pentyl)phosphonic acid

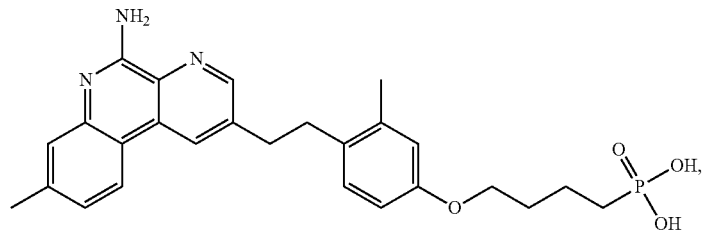

Compound 62 (4-(4-(2-(5-amino-8-methylbenzo[f][1,7]naphthyridin-2-yl)ethyl)-3-methylphenoxy)butyl)phosphonic acid

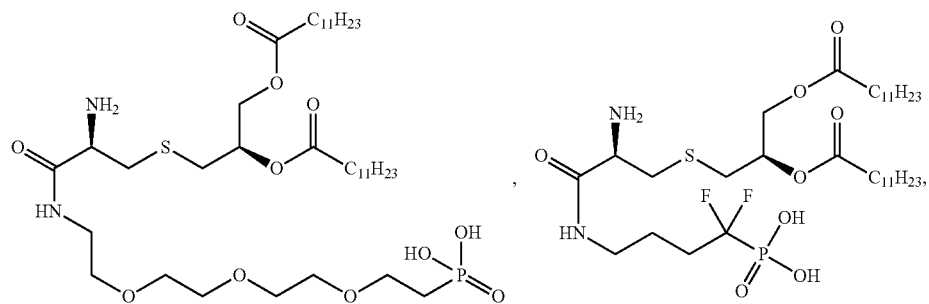

Compound 63 (14R,18R)-14-amino-18-(dodecanoyloxy)-13,21-dioxo-3,6,9,20-tetraoxa-16-thia-12-azadotriacontylphosphonic acid Compound 64 4-((R)-2-amino-3-((R)-2,3-bis(dodecanoyloxy)propylthio)propanamido)-1,1-difluorobutylphosphonic acid

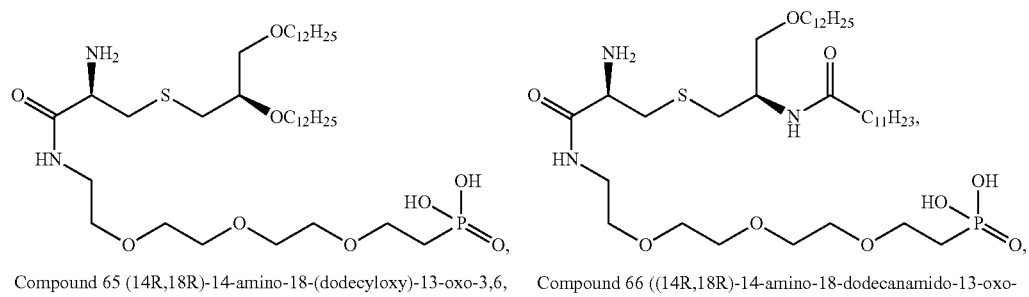

Compound 65 (14R,18R)-14-amino-18-(dodecyloxy)-13-oxo-3,6,9,20-tetraoxa-16-thia-12-azadotriacontylphosphonic acid Compound 66 ((14R,18R)-14-amino-18-dodecanamido-13-oxo-3,6,9,20-tetraoxa-16-thia-12-azadotriacontyl)phosphonic acid

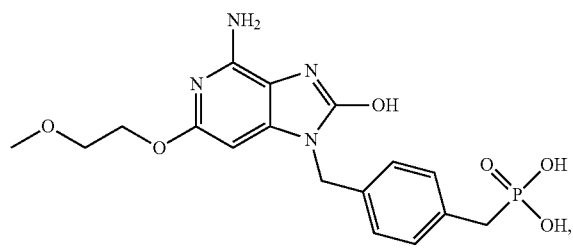

Compound 67 (4-((4-amino-6-(2-methoxyethoxy)-2-oxo-2,3-dihydro-1H-imidazo[4,5-c]pyridin-1-yl)methyl)benzyl)phosphonic acid

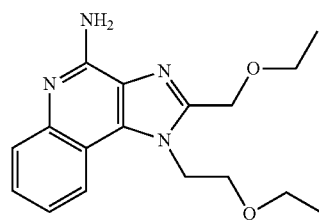

Compound 68 (2-(2-(2-(2-(4-amino-2-(ethoxymethyl)-1H-imidazo[4,5-c]quinolin-1-yl)ethoxy)ethoxy)ethoxy)ethyl)phosphonic acid

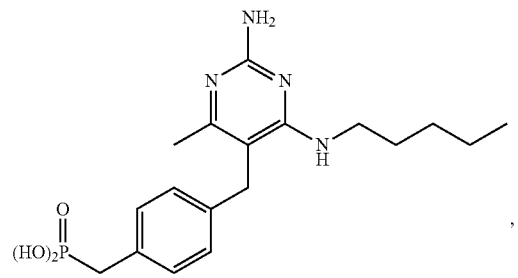

Compound 69 (4-((2-amino-4-methyl-6-(pentylamino)pyrimidin-5-yl)methyl)benzyl)phosphonic acid

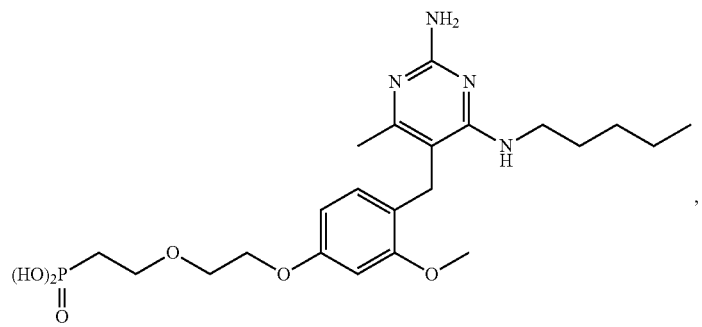

Compound 70 (2-(2-(4-((2-amino-4-methyl-6-(pentylamino)pyrimidin-5-yl)methyl)-3-methoxphenoxy)ethoxy)ethyl) phosphonic acid

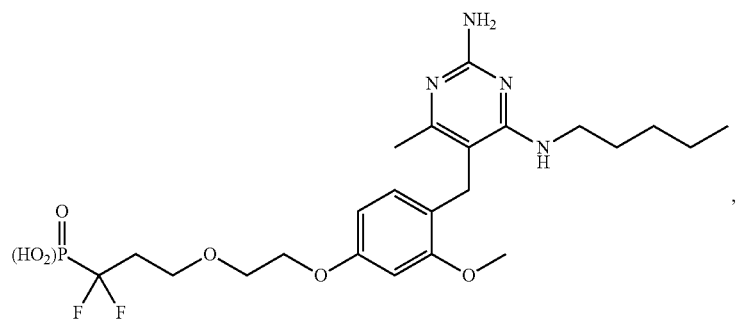

Compound 71 (3-(2-(4-((2-amino-4-methyl-6-(pentylamino)pyrimidin-5-yl)methyl)-3-methoxyphenoxy)ethoxy)-1,1-difluoropropyl)phosphonic acid

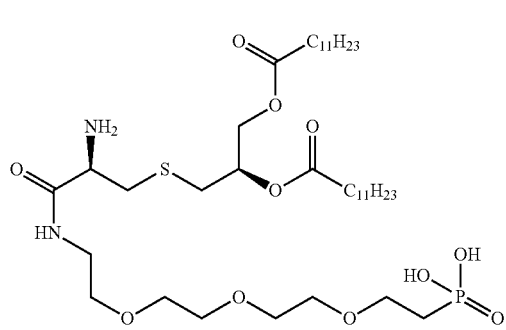

Compound 72 ((14R,18R)-14-amino-18-(dodecanoyloxy)-13,21-dioxo-3,6,9,20-tetraoxa-16-thia-12-azadotriacontyl)phosphonic acid

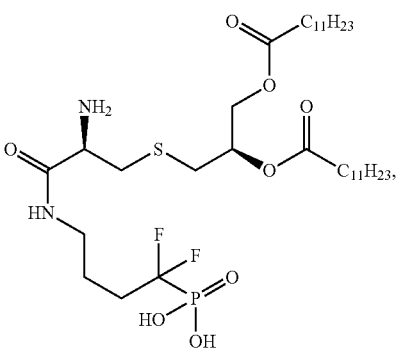

Compound 73 (4-((R)-2-amino-3-(((R)-2,3-bis(dodecanoyloxy)propyl)thio)propanamido)-1,1-difluorobutyl)phosphonic acid;

-continued

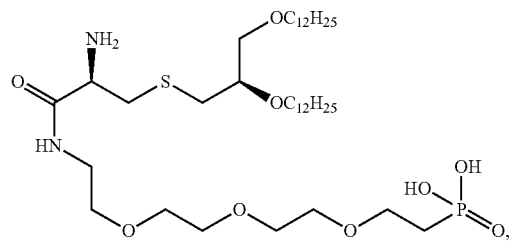

Compound 74 ((14R,18R)-14-amino-18-(dodecyloxy)-13-oxo-3,6,9,20-tetraoxa-16-thia-12-azadotriacontyl)phosphonic acid

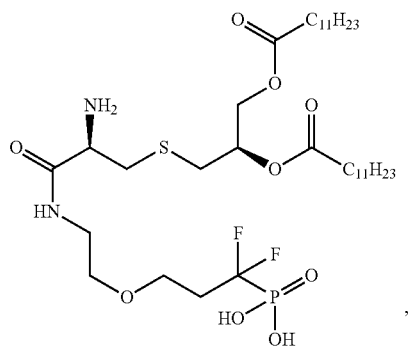

Compound 75 ((9R,13R)-9-amino-13-(dodecanoyloxy)-1,1-difluoro-8,16-dioxo-4-,15-dioxa-11-thia-7-azaheptacosyl) phosphonic acid

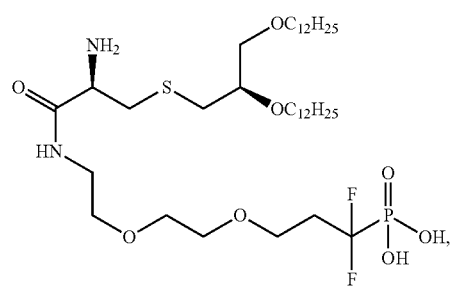

Compound 76 ((12R,16R)-12-amino-16-(dodecyloxy)-1,1-difluoro-11-oxo-4,7,18-trioxa-14-thia-10-azatriacontyl) phosphonic acid

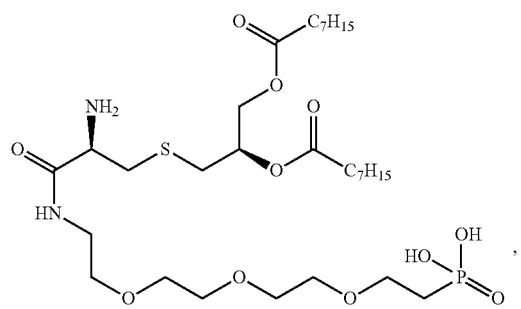

Compound 77 ((14R,18R)-14-amino-18-(octanoyloxy)-13,21-dioxo-3,6,9,20-tetraoxa-16-thia-12-azaoctacosyl) phosphonic acid

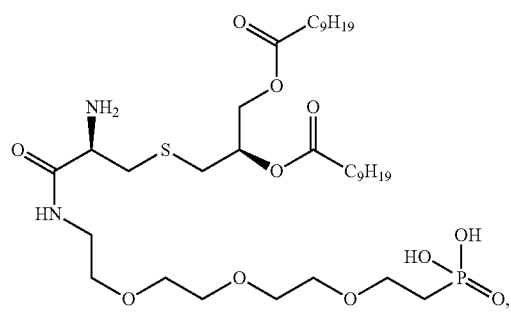

Compound 78 ((14R,18R)-14-amino-18-(decanoyloxy)-13,21-dioxo-3,6,9,20-tetraoxa-16-thia-12-azatriacontyl) phosphonic acid

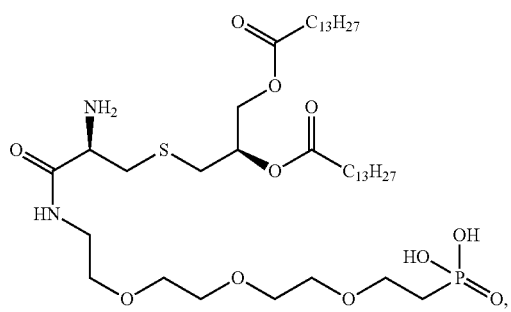

Compound 79 ((14R,18R)-14-amino-13,21-dioxo-18-(tetradecanoyloxy)-3,6,9,20-tetraoxa-16-thia-12-azatetratriacontyl)phosphonic acid

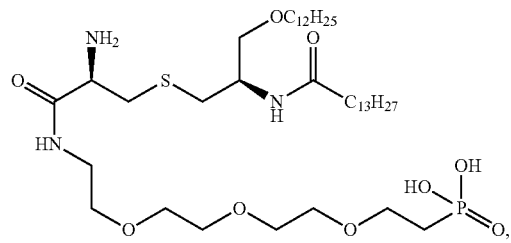

Compound 80 ((14R,18R)-14-amino-18-dodecanamido-13-oxo-3,6,9,20-tetraoxa-16-thia-12-azadotriacontyl)phosphonic acid

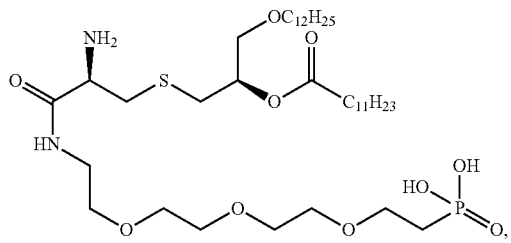

Compound 81 ((14R,18R)-14-amino-18-(dodecanoyloxy)-13-oxo-3,6,9,20-tetraoxa-16-thia-12-azadotriacontyl)phosphonic acid

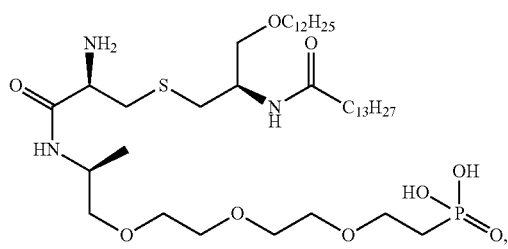

Compound 82 ((11S,14R,18R)-14-amino-18-dodecanamido-11-methyl-13-oxo-3,6,9,20-tetraoxa-16-thia-12-azadotriacontyl) phosphonic acid

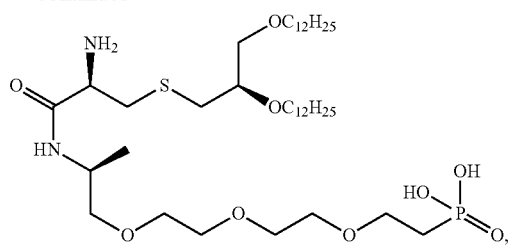

Compound 83 ((11S,14R,18R)-14-amino-18-(dodecyloxy)-11-methyl-13-oxo-3,6,9,20-tetraoxa-16-thia-12-azadotriacontyl) phosphonic acid

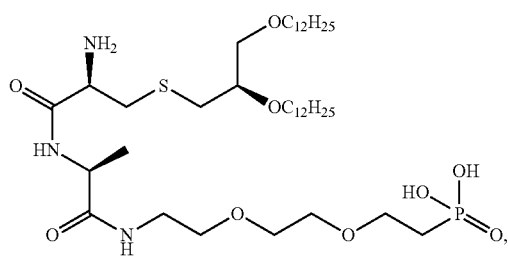

Compound 84 ((11S,14R,18R)-14-amino-18-(dodecyloxy)-11-methyl-10,13-dioxo-3,6,20-trioxa-16-thia-9,12-diazadotriacontyl)phosphonic acid

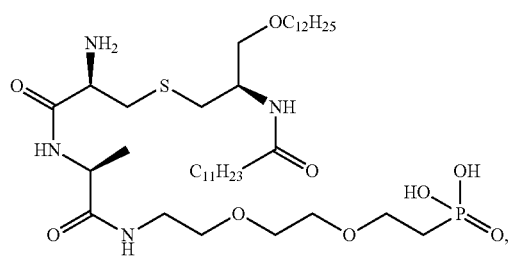

Compound 85 ((11S,14R,18R)-14-amino-18-dodecanamido-11-methyl-10,13-dioxo-3,6,20-trioxa-16-thia-9,12-diazadotriacontyl)phosphonic acid

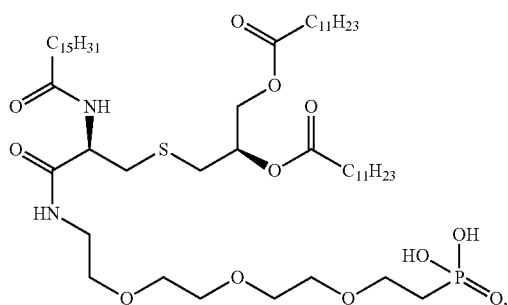

Compound 86 ((14R,18R)-18-(dodecanoyloxy)-13,21-dioxo-14-palmitamido-3,6,9,20-tetraoxa-16-thia-12-azadotriacontyl) phosphonic acid

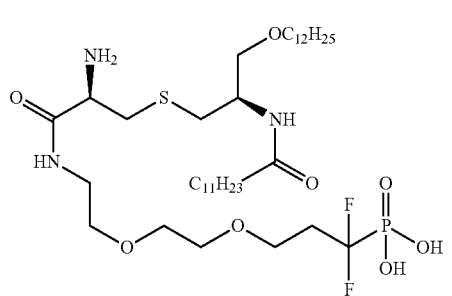

Compound 87 ((12R,16R)-12-amino-16-dodecanamido-1,1-difluoro-11-oxo-4,7,18-trioxa-14-thia-10-azatriacontyl)phosphonic acid

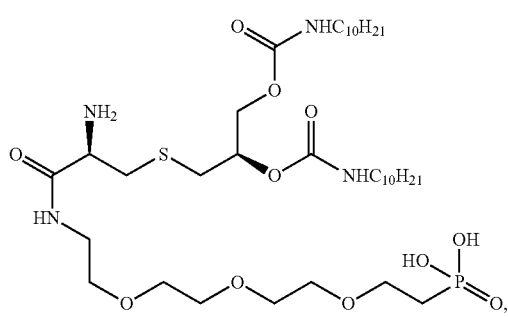

Compound 88 ((14R,18R)-14-amino-18-((decylcarbamoyl)oxy)-13,21-dioxo-3,6,9,20-tetraoxa-16-thia-12,22-diazadotriacontyl) phosphonic acid

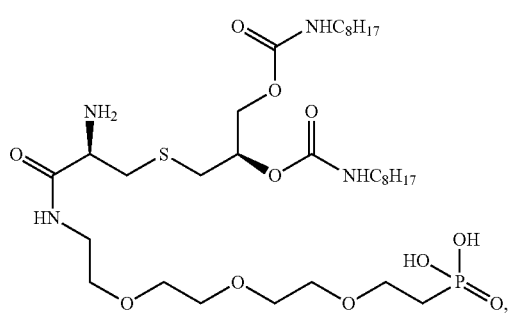

Compound 89 ((14R,18R)-14-amino-18-((octylcarbamoyl)oxy)-13,21-dioxo-3,6,9,20-tetraoxa-16-thia-12,22-diazatriacontyl) phosphonic acid -continued

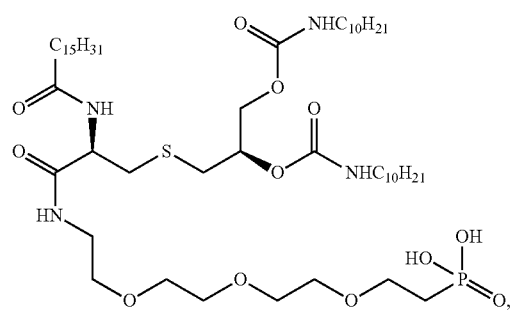

Compound 90 ((14R,18R)-18-((decylcarbamoyl)oxy)-13,21-dioxo-14-palmitamido-3,6,9,20-tetraoxa-16-thia-12,22-diazadotriacontyl)phosphonic acid

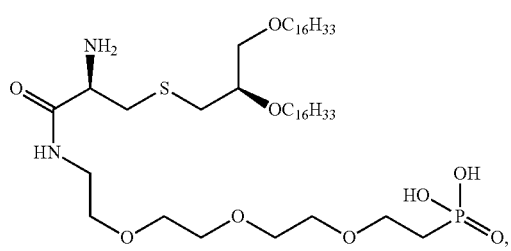

Compound 91 ((14R,18R)-14-amino-18-(hexadecyloxy)-13-oxo-3,6,9,20-tetraoxa-16-thia-12-azahexatriacontyl) phosphonic acid

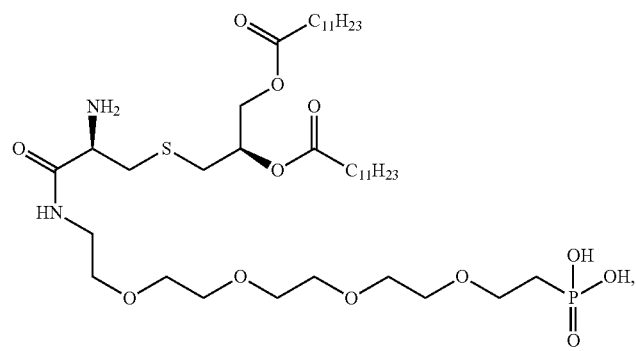

Compound 92 ((17R,21R)-17-amino-21-(dodecanoyloxy)-16,24-dioxo-3,6,9,12,23-pentaoxa-19-thia-15-azapentatriacontyl)phosphonic acid

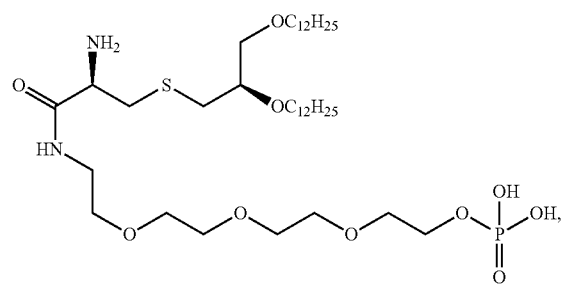

Compound 93 ((17R,21R)-17-amino-21-(dodecyloxy)-16-oxo-3,6,9,12,23-pentaoxa-19-thia-15-azapentatriacontyl)phosphonic acid

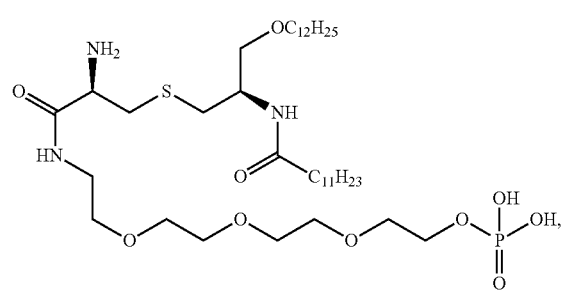

Compound 94 ((17R,21R)-17-amino-21-dodecanamido-16-oxo-3,6,9,12,23-pentaoxa-19-thia-15-azapentatriacontyl)phosphonic acid

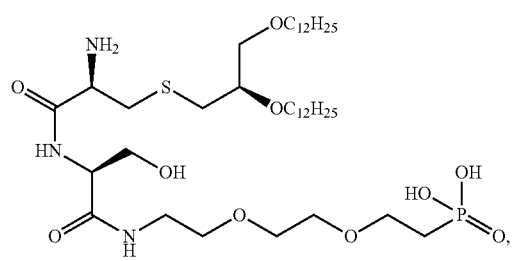

Compound 95 ((11S,14R,18R)-14-amino-18-(dodecyloxy)-11-(hydroxymethyl)-10,13-dioxo-3,6,20-trioxa-16-thia-9,12-diazadotriacontyl)phosphonic acid

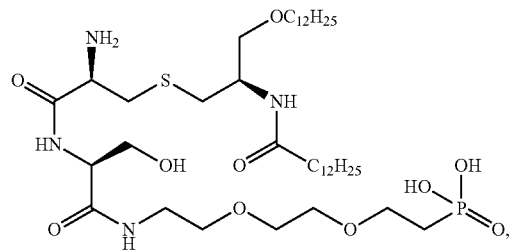

Compound 96 ((11S,14R,18R)-14-amino-18-dodecanamido-11-(hydroxymethyl)-10,13-dioxo-3,6,20-trioxa-16-thia-9,12-diazadotriacontyl)phosphonic acid

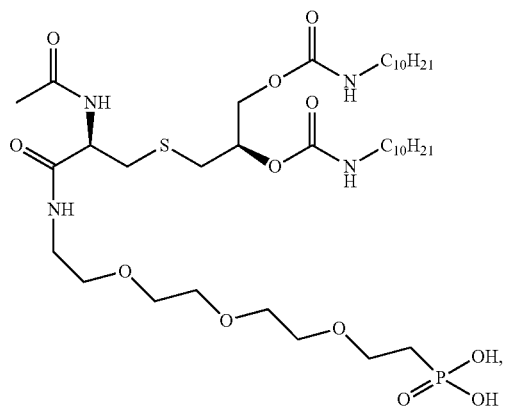

Compound 97 ((14R,18R)-14-acetamido-18-((decylcarbamoyl)oxy)-13,21-dioxo-3,6,9,20-tetraoxa-16-thia-12,22-diazadotriacontyl)phosphonic acid

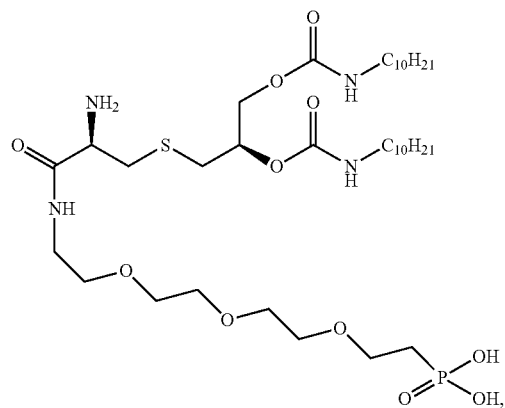

Compound 98 ((14R,18R)-14-amino-18-((decylcarbamoyl)oxy-13,21-dioxo-3,6,9,20-tetraoxa-16-thia-12,22-diazadotriacontyl)phosphonic acid

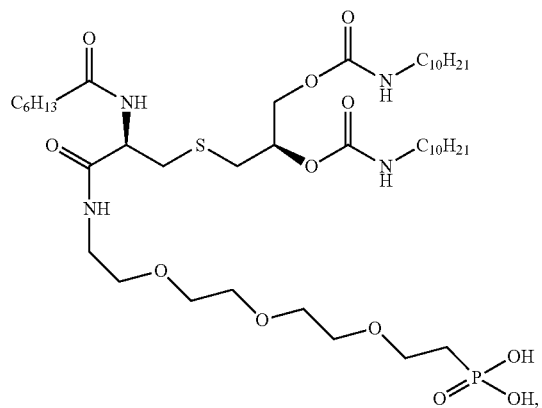

Compound 99 ((14R,18R)-18-((decylcarbamoyl)oxy)-14-heptanamido-13,21-dioxo-3,6,9,20-tetraoxa-16-thia-12,22-diazadotriacontyl)phosphonic acid

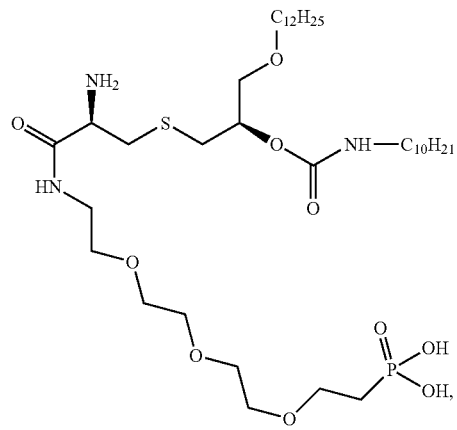

Compound 100 ((14R,18R)-14-amino-18-((dodecyloxy)methyl)-13,20-dioxo-3,6,9,19-tetraoxa-16-thia-12,21-diazahentriacontyl)phosphonic acid

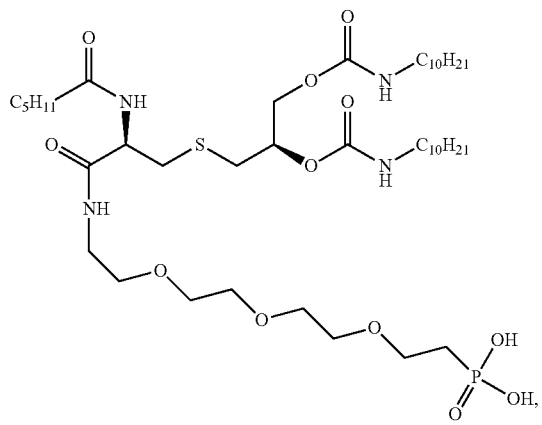

Compound 101 ((14R,18R)-18-((decylcarbamoyl)oxy)-14-hexanamido-13,21-dioxo-3,6,9,20-tetraoxa-16-thia-12,22-diazadotriacontyl)phosphonic acid

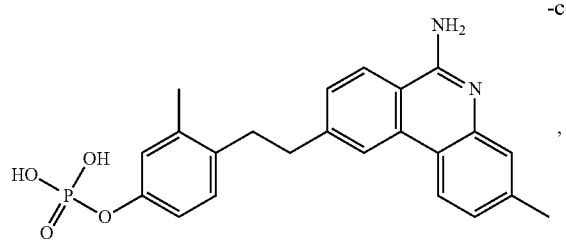

Compound 102 4-(2-(5-amino-8-methylbenzo[f][1,7]naphthyridin-2-yl)ethyl)-3-methylphenyl dihydrogen phosphate or a pharmaceutically acceptable salt thereof.

11. The composition of claim 1, further comprising a histidine buffer.

12. The composition of claim 1, comprising a diphtheria toxoid concentration ≤4 Lf/ml.

13. The composition of claim 1, comprising a tetanus toxoid concentration ≤9 Lf/ml.

14. The composition of claim 1, comprising a pertussis toxoid concentration ≤4 μg/ml.

15. The composition of claim 1, further comprising a trivalent inactivated poliovirus antigen component.

16. The composition of claim 1, wherein the composition has a pH between 6.1 and 7.9.

17. A method of raising an immune response in a subject, comprising the step of administering to the subject the composition of claim 1.

18. The method of claim 17, wherein the subject has previously received a DTP vaccine as a child.

19. The composition of claim 1, wherein at least one of the diphtheria toxoid, the tetanus toxoid, and the pertussis toxoid is adsorbed to the aluminium salt adjuvant.

* * * * *